US010271931B2

(12) United States Patent
Huffman

(10) Patent No.: US 10,271,931 B2
(45) Date of Patent: Apr. 30, 2019

(54) IMPRESSIONLESS DENTAL MODELING SYSTEMS AND METHODS

(71) Applicant: Ronald E. Huffman, Tucson, AZ (US)

(72) Inventor: Ronald E. Huffman, Tucson, AZ (US)

(*) Notice: Subject to any disclaimer, the term of this patent is extended or adjusted under 35 U.S.C. 154(b) by 0 days.

(21) Appl. No.: 15/285,049

(22) Filed: Oct. 4, 2016

(65) Prior Publication Data

US 2017/0020640 A1    Jan. 26, 2017

Related U.S. Application Data

(62) Division of application No. 14/350,765, filed as application No. PCT/US2012/060227 on Oct. 15, 2012, now Pat. No. 9,456,882.

(Continued)

(51) Int. Cl.
*A61C 1/14* (2006.01)
*A61C 13/34* (2006.01)
(Continued)

(52) U.S. Cl.
CPC ............ *A61C 13/34* (2013.01); *A61C 5/77* (2017.02); *A61C 9/002* (2013.01); *A61C 11/00* (2013.01);
(Continued)

(58) Field of Classification Search
CPC ........... A61C 13/34; A61C 5/77; A61C 9/002; A61C 9/004; A61C 11/00; A61C 11/003;
(Continued)

(56) References Cited

U.S. PATENT DOCUMENTS 4,734,033 A    3/1988   Huffman
5,658,143 A    8/1997   Kuperman
(Continued)

FOREIGN PATENT DOCUMENTS

JP    2004283259 A    10/2004
JP    2009100880 A    5/2009
(Continued)

OTHER PUBLICATIONS

PCT International Search Report for PCT International Patent Application No. PCT/US2012/060227, dated Mar. 22, 2013.
(Continued)

*Primary Examiner* — Nicholas Lucchesi
(74) *Attorney, Agent, or Firm* — Holland & Hart LLP

(57) ABSTRACT

Dental systems and methods related to impressionless dental modeling. A dental modeling system includes a dental model base and a mounting plate. The dental model base includes a plate support surface and a plurality of pin receiving apertures formed in the support surface. The mounting plate includes a plate portion positioned on the plate support surface and a plurality of pins extending into the pin receiving apertures to provide removable attachment of the mounting plate to the dental model base. The plate portion includes a model support surface configured to support a model of a person's teeth. The model may be formed directly on the model support surface using an impressionless technique. The model may be formed separately using an impressionless technique and then bonded to the model support surface.

19 Claims, 74 Drawing Sheets

Related U.S. Application Data

(60) Provisional application No. 61/546,909, filed on Oct. 13, 2011.

(51) Int. Cl.
| | | |
|---|---|---|
| *A61C 5/77* | (2017.01) | |
| *A61C 11/00* | (2006.01) | |
| *A61C 9/00* | (2006.01) | |
| *A61C 11/08* | (2006.01) | |
| *G06F 17/50* | (2006.01) | |
| *A61C 13/00* | (2006.01) | |

(52) U.S. Cl.
CPC ............ *A61C 11/003* (2013.01); *A61C 11/08* (2013.01); *A61C 13/0027* (2013.01); *G06F 17/50* (2013.01); *Y10T 29/49567* (2015.01)

(58) Field of Classification Search
CPC .... A61C 11/08; A61C 13/004; A61C 13/0027
See application file for complete search history.

(56) References Cited

U.S. PATENT DOCUMENTS

| | | |
|---|---|---|
| 5,788,490 A | 8/1998 | Huffman |
| 5,800,166 A | 9/1998 | Huffman |
| 5,868,569 A | 2/1999 | Huffman |
| 5,934,901 A | 8/1999 | Huffman |
| D429,815 S | 8/2000 | Huffman |
| D430,672 S | 9/2000 | Huffman |
| D433,136 S | 10/2000 | Huffman |
| D433,754 S | 11/2000 | Huffman |
| D443,363 S | 6/2001 | Huffman |
| D444,559 S | 7/2001 | Huffman |
| D456,902 S | 5/2002 | Huffman |
| D456,903 S | 5/2002 | Huffman |
| D456,904 S | 5/2002 | Huffman |
| D457,243 S | 5/2002 | Huffman |
| D457,636 S | 5/2002 | Huffman |
| D457,637 S | 5/2002 | Huffman |
| D457,963 S | 5/2002 | Huffman |
| D457,964 S | 5/2002 | Huffman |
| D464,431 S | 10/2002 | Huffman |
| D464,432 S | 10/2002 | Huffman |
| D464,732 S | 10/2002 | Huffman |
| D465,027 S | 10/2002 | Huffman |
| 6,471,513 B1 | 10/2002 | Huffman |
| D468,018 S | 12/2002 | Huffman |
| D468,432 S | 1/2003 | Huffman |
| D469,537 S | 1/2003 | Huffman |
| D481,797 S | 11/2003 | Huffman |
| 6,884,068 B2 | 4/2005 | Huffman |
| 7,044,734 B2 | 5/2006 | Huffman |
| 7,108,507 B2 | 9/2006 | Huffman |
| 7,147,465 B2 | 12/2006 | Jung et al. |
| 7,210,931 B1 | 5/2007 | Huffman |
| 7,210,932 B2 | 5/2007 | Honstein et al. |
| 7,690,919 B2 | 4/2010 | Huffman |
| 7,698,014 B2 * | 4/2010 | Dunne ................. A61B 5/4547 433/25 |
| 8,535,580 B2 * | 9/2013 | Puttler ..................... A61C 7/00 264/16 |
| 8,750,590 B2 * | 6/2014 | Greenberg ............... A61B 6/14 382/131 |
| 9,539,062 B2 * | 1/2017 | Rubbert .................. A61C 5/007 |
| 9,539,072 B2 * | 1/2017 | El-Siblani .............. A61C 13/34 |
| 9,687,324 B2 * | 6/2017 | Fisker ................ A61C 13/0004 |
| 9,782,238 B2 * | 10/2017 | Kopelman ........... A61C 9/0053 |
| 2004/0029070 A1 | 2/2004 | Huffman |
| 2006/0281043 A1 | 12/2006 | Huffman |
| 2007/0128579 A1 | 6/2007 | Shima |
| 2009/0208895 A1 | 8/2009 | Lin |

FOREIGN PATENT DOCUMENTS

| | | |
|---|---|---|
| JP | 2011015829 A | 1/2011 |
| WO | 2006135645 A2 | 12/2006 |

OTHER PUBLICATIONS

Supplementary European Search Report for Application No. EP 12839310, dated Aug. 12, 2015.

* cited by examiner

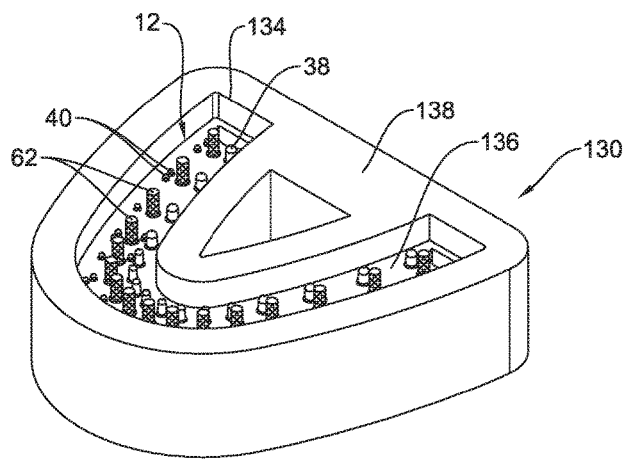
FIG. 41A
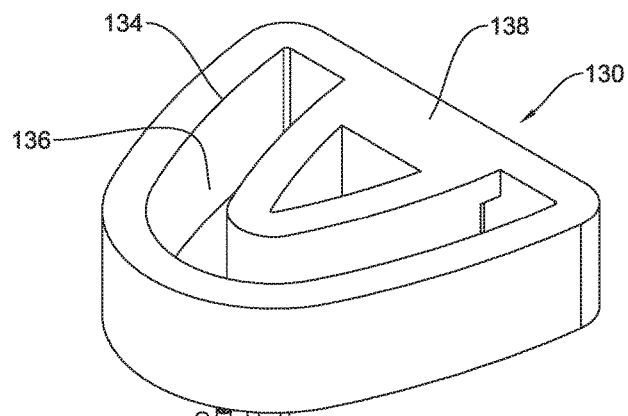
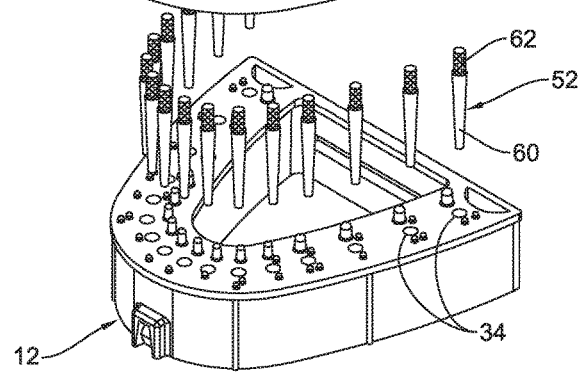
FIG. 41B

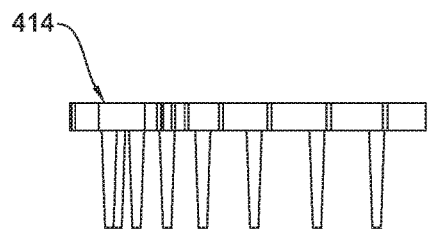
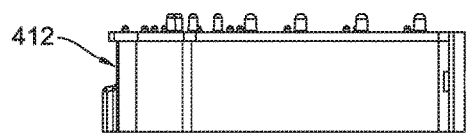
FIG. 51A
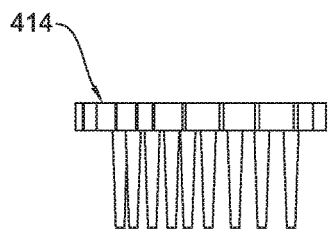
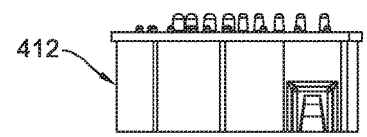
FIG. 51C
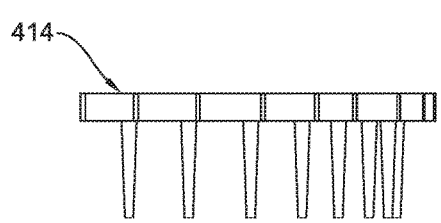
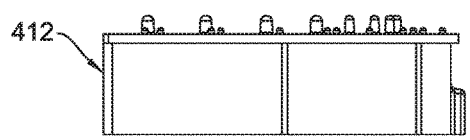
FIG. 51B
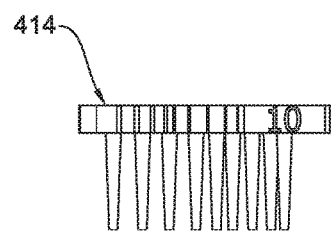
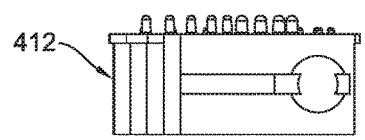
FIG. 51D

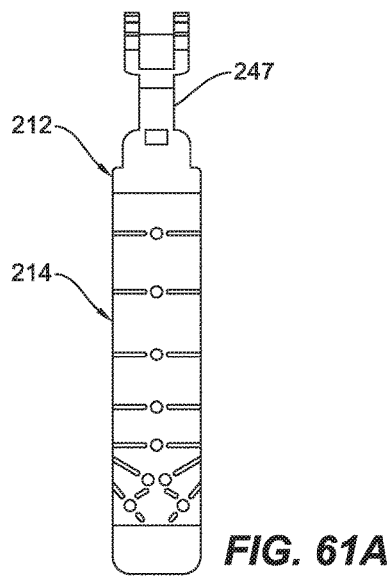
FIG. 61A
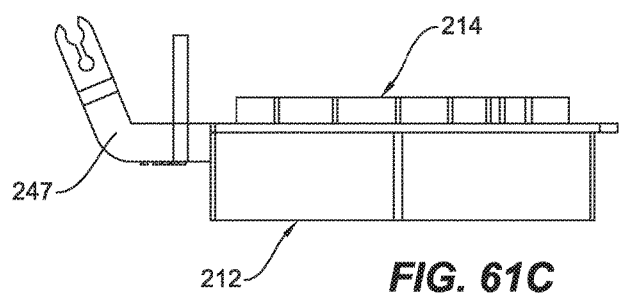
FIG. 61C
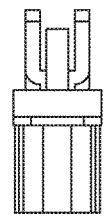 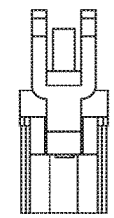
FIG. 61E   FIG. 61F
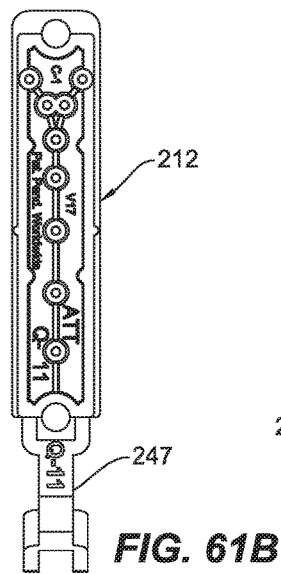
FIG. 61B
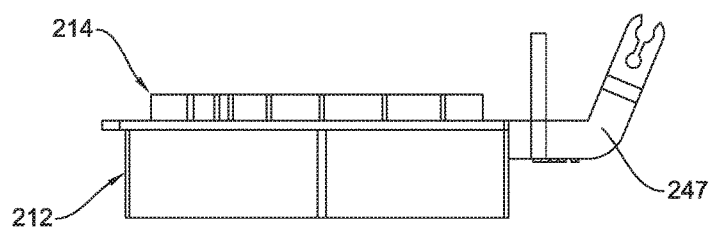
FIG. 61D

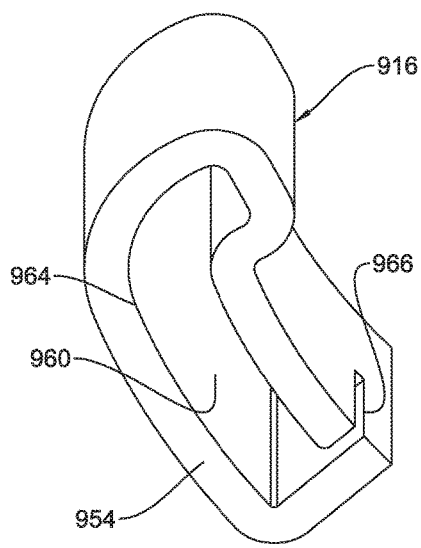
FIG. 89
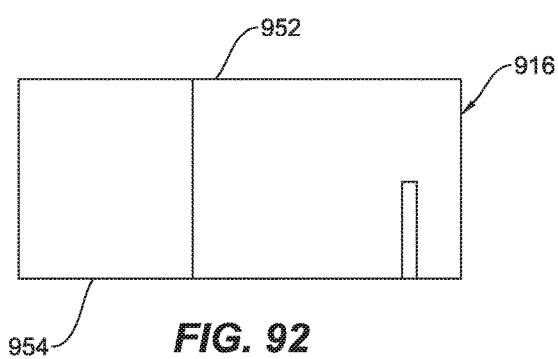
FIG. 92
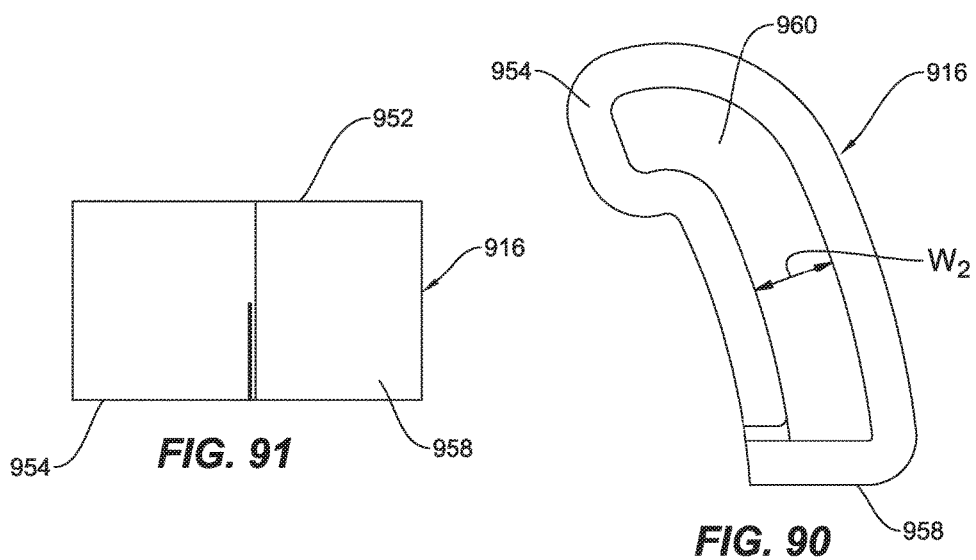
FIG. 91
FIG. 90

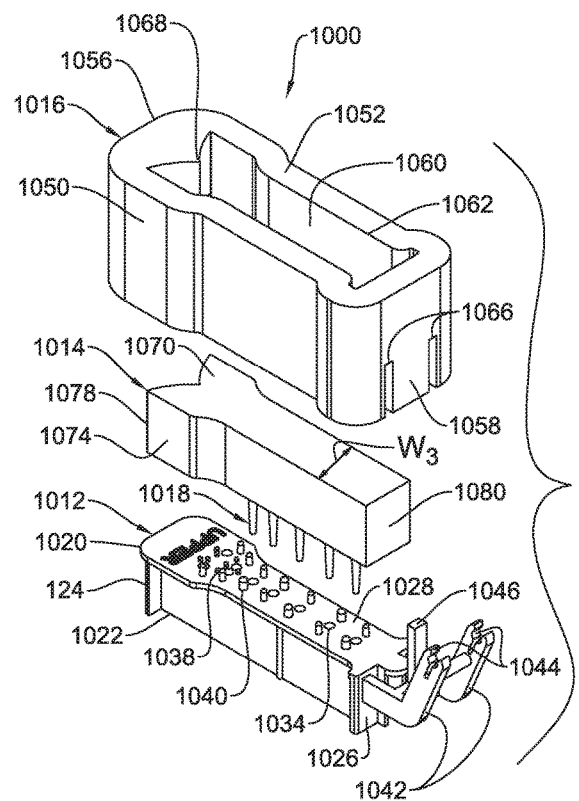
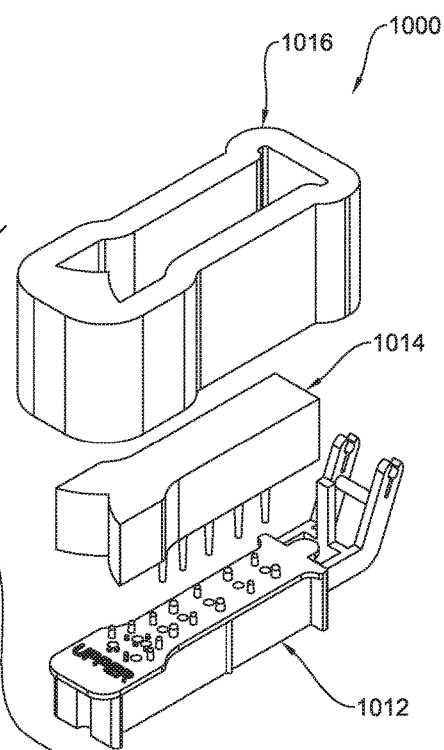
FIG. 97
FIG. 98

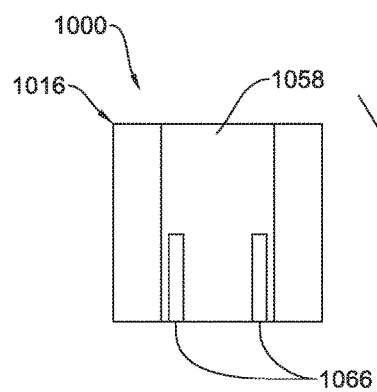
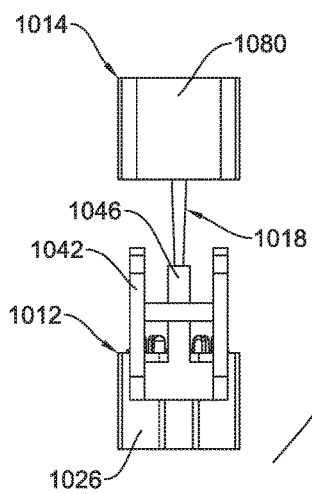
*FIG. 101*
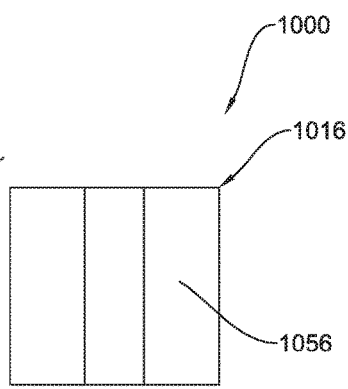
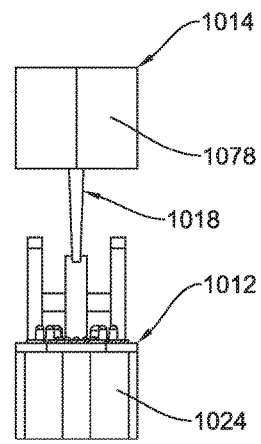
*FIG. 102*

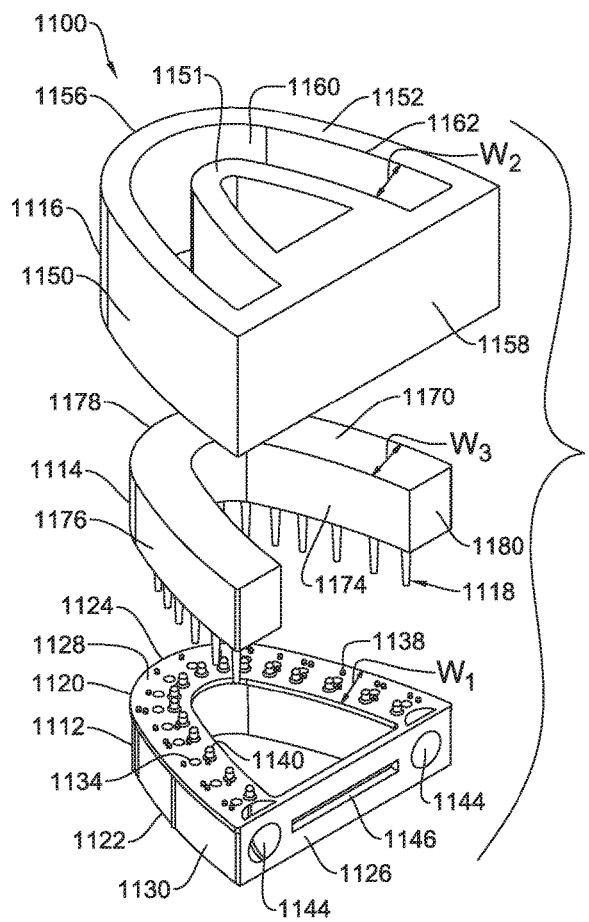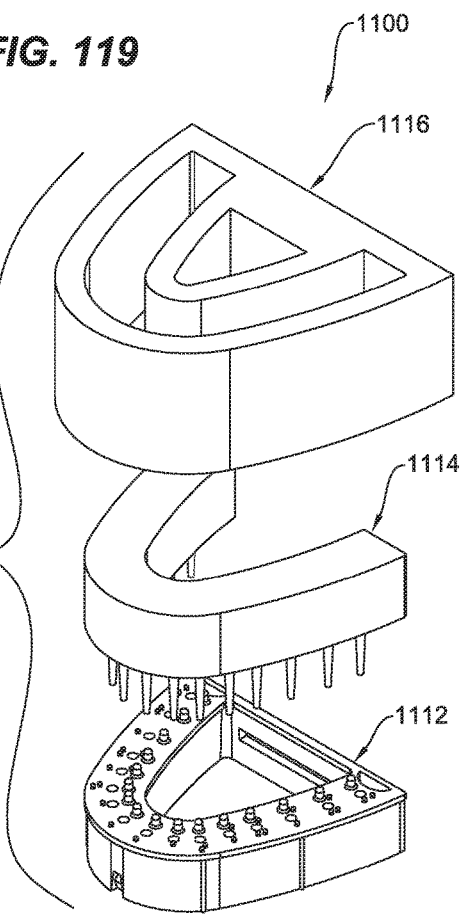

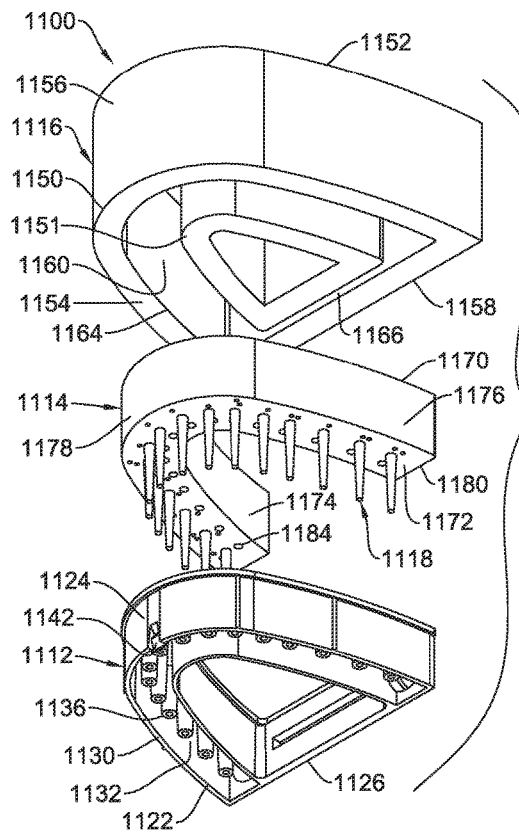
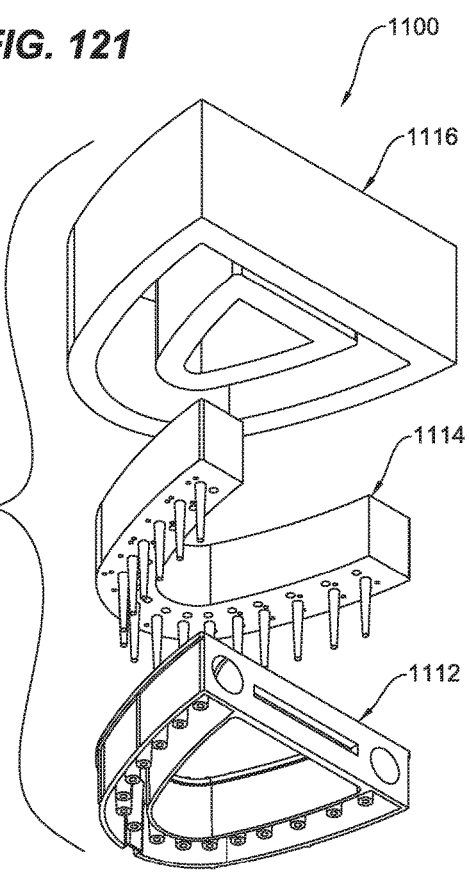

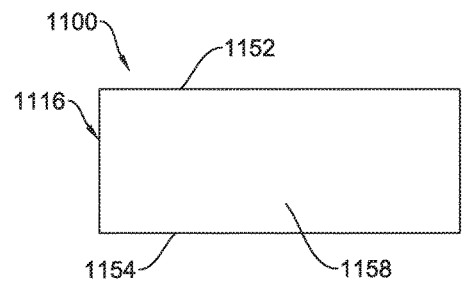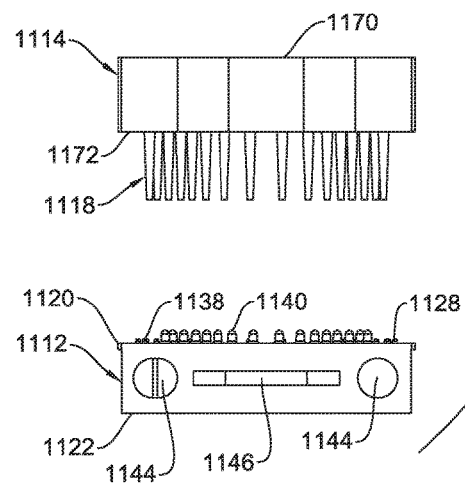
FIG. 123
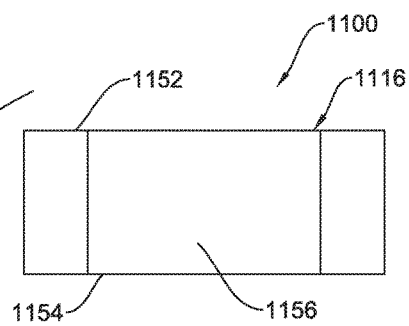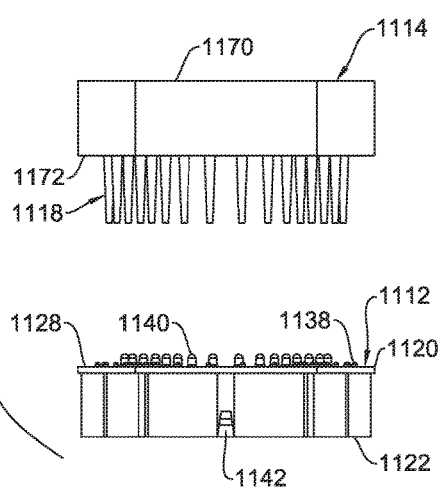
FIG. 124

IMPRESSIONLESS DENTAL MODELING SYSTEMS AND METHODS

RELATED APPLICATIONS

This is a divisional of U.S. patent application Ser. No. 14/350,765, filed 9 Apr. 2014, now U.S. Pat. No. 9,456,882, issued Oct. 4, 2016, which is a 371 of PCT Application No. PCT/US2012/060227, filed Oct. 15, 2012, which claims the benefit of Provisional Application Ser. No. 61/546,909, filed Oct. 13, 2011, the disclosures of which are incorporated, in their entireties, by this reference.

TECHNICAL FIELD

The present disclosure is directed to dental modeling systems and methods, and more particularly relates to dental modeling systems operable without a dental impression.

BACKGROUND

Creating a dental model from a mold of a person's teeth is a well-known practice. Dental models are used for dental work such as, for example, dental prosthesis (e.g., crowns and bridges), and orthodontics. A mold of a person's teeth is typically formed when a patient bites into a pliant casting material that cures to create a mold cavity defining a negative impression of the person's teeth and gums (i.e., a "dental mold" or "teeth impression"). The dental mold can represent all or any portion of the person's teeth and gum line. When forming a dental model, a castable or moldable material is poured into the negative impression of the dental mold and the cured castable material provides a stone replica or dental model of the patient's teeth and gums.

A dental model base may be concurrently connected to the dental model during formation of the dental model from the dental mold. The dental model base typically includes at least one removable pin that is associated with one of the teeth impressions in the dental mold. After formation of the dental model, individual teeth of the dental model (a "tooth model") can be separated from each other by cutting. The removable pin provides a connection between the tooth model and the dental model base and provides structure for the technician to handle the tooth model.

Advances have been made in the area of impressionless tooth modeling. Impressionless tooth modeling includes creating digital images of a person's teeth using digital imaging technology. In one example, data representing the digital image is input electronically into a milling machine that uses lasers or other cutting technology to cut or mill a dental model from a blank of cured model material. The model material may be, for example, porcelain or hardened stone material. In another example, data representing the digital image is input electronically into a rapid prototyping type machine (e.g., a stereo-lithography machine) that deposits small amounts of model material in layers, which layers when accumulated result in the dental model.

Impressionless tooth modeling eliminates the need to create the dental mold (i.e., dental impression) discussed above. Further, the electronic format of the digital images of a person's teeth makes it possible to send the digital images electronically, such as over the Internet, to a dental lab where the dental model is created. Sending the digital images electronically can save cost and time over the processes required when using dental molds.

Improvements in impressionless tooth modeling systems and methods are available.

DISCLOSURE OF THE INVENTION

The present disclosure is directed generally to dental modeling devices, systems and methods. More specifically, the present disclosure relates to dental modeling devices, systems and methods that provide impressionless modeling of a person's tooth or teeth. The term impressionless model may relate to a model that is formed without taking a traditional impression of a person's teeth, which is usually accomplished by filling a tray with plaster or other curable impression material, inserting the tray into a person's mouth, and biting into the plaster to form an impression of the person's teeth. The impression is then filled with a model forming material, which when cured, forms a model of the person's teeth.

One aspect of the present disclosure relates to a dental modeling system that includes a dental model base and a mounting plate. The dental model base includes a plate support surface and a plurality of pin receiving apertures formed in the support surface. The mounting plate includes a plate portion positioned on the plate support surface and a plurality of pins extending into the pin receiving apertures. The plate portion includes a model support surface configured to support a model of a person's teeth.

The mounting plate may include a plurality of markings on the model support surface, wherein the markings represent average teeth positions from at least a portion of an arc of teeth. The plate portion may include polyurethane. The plurality of pins may include a metal material, and the plate portion may include a polymer material. The dental model base may include a first snap-fit feature formed in a first end surface thereof, and a second snap-fit feature formed in a second end surface thereof arranged opposite the first end surface. The snap-fit feature may include a ball-and-socket connection feature. The snap-fit feature may include a latch member, such as a flexible arm having a nipple or protrusion at a distal end thereof.

The dental model base may include a plurality of indexing pins extending from the plate support surface, and the plate portion of the mounting plate includes a plurality of indexing apertures formed in a bottom surface thereof, which are receptive of the plurality of indexing pins. The dental model base and the mounting plate may each comprise an arc-shaped portion. The dental model base may include at least one articulating arm configured to pivotally connect to at least one articulating arm of another dental model base.

Another aspect of the present disclosures relates to a dental modeling assembly that includes a dental model base, a mounting plate, and an alignment jig. The mounting plate may include a plate portion and a plurality of pins, wherein the plate portion is configured to support a model of a person's teeth. The alignment jig includes a support base, a pedestal, a support stand, and a pin locator. The pedestal extends vertically from the support base. The support stand extends vertically from the support base. The support stand extends vertically from the support base and is arranged adjacent to the pedestal. The pin locator is mounted to the support stand and includes a plurality of alignment pins. The dental model base is mounted to the pedestal and the mounting plate is mounted to the dental model base with a plurality of pins extending into the dental model base. The alignment jig is operable to position the alignment pins adjacent to teeth portions of the model to orient the model relative to the dental model base and mounting plate.

The support stand may telescope in a vertical direction. The alignment jig may include a support arm, the pin locator is connected to the support arm, and the support arm is pivotally connected to the support stand. The support stand may include a housing member, a screw member, and an inner slide. The screw member may contact a threaded portion of the inner slide, and the inner slide may be movable vertically relative to the housing by rotating the screw member. The dental modeling assembly may also include an index plate (also referred to as a an attachment plate) interposed between the pedestal and the dental model plate. The index plate may include at least one snap-fit or other quick release connection feature for releasably mounting the dental model base to the pedestal.

A further aspect of the present disclosure relates to a method of forming a dental model assembly. The method includes providing a dental model base, a model of at least a portion of an arc of a person's teeth, a mounting plate, and an alignment jig. The mounting plate includes a plurality of mounting pins, and the alignment jig includes a pin locator having a plurality of alignment pins. The method also includes mounting the mounting plate to the dental model base with a plurality of mounting pins extending into the dental model base, mounting a dental model base to the alignment jig, positioning the model on the mounting plate, adjusting the alignment jig and adjusting a position of the model relative to the mounting plate to position the alignment pins adjacent to teeth of the model, and connecting the model to the mounting plate with the adhesive.

The alignment jig may include a base portion and a pedestal extending vertically from the base portion, and mounting the dental model based to the alignment jig includes mounting to the pedestal. The alignment jig may include a support stand, and adjusting the alignment jig may include operating the support stand to adjust a vertical position of the pin locator. The alignment jig may include a support arm pivotally mounted to the support stand, the pin locator may be mounted to the support arm, and adjusting the alignment jig may include rotating the support arm between a first position removed from the model and a second position arranged adjacent to and vertically above the model. Mounting the dental model base to the alignment jig may include providing a snap-fit connection between the alignment jig and the dental model base.

One aspect of the present disclosure relates to a dental device configured to mount to a dental model base having a model support surface. The dental device includes a sidewall, a first opening, and a second opening. The sidewall defines a mold cavity. The first opening provides access into the cavity and is sized to receive a volume of curable modeling material. The second opening provides access into the cavity and is sized to receive a portion of the dental model base with the model support surface exposed within the cavity. The curable modeling material when cured is mounted to the dental model base and has a shape defined at least in part by the sidewall.

Another aspect of the present disclosure relates to a dental modeling assembly that includes a dental model base, a mold member, and a volume of curable modeling material. The dental model base includes a model support surface and at least one removable pin extending from the model support surface. The mold member is releasably mounted to the dental model base and defines a cavity. The model support surface is positioned in the cavity. The volume of curable modeling material is positioned in the mold member and is mounted to the dental model base. The curable modeling material when cured is configured to be cut into a model of at least one tooth. The dental model base may include a mounting plate having a plate portion and the at least one removable pins connected to the plate portion. The mounting plate may be removable and may define the model support surface.

A further aspect of the present disclosure relates to a dental modeling assembly that includes a dental model base and a mold cavity. The dental model base defines a model support surface and includes at least one pin member extending from the model support surface. The mold member is releasably mounted to the dental model base and defines a mold cavity that is configured to receive a volume of curable modeling material. The model support surface and pin member are exposed in the mold cavity.

Another aspect of the present disclosure relates to a dental modeling assembly that includes an opposing base, a dental model base, and at least one mold member. The opposing base includes a cavity and a plurality of retaining pins positioned in the cavity. The dental model base includes a support surface and a plurality of removable pins extending from the support surface. The at least one mold member is releasably mounted to one of the opposing base and the dental model base. The mold member includes at least one wall structure and a connection feature. The wall structure has an inner surface that defines a cavity, wherein the cavity being configured to retain a curable material. The connection feature is configured to mount the form member to one of the opposing base and the dental model base.

Another aspect of the present disclosure relates to a method of forming a dental modeling assembly. The method includes providing a dental model base and a mold member, the dental model base having a model support surface and at least one removable pin extending from the model support surface, and the mold member defining a cavity. The method also includes mounting the mold member to the dental model base, and filling at least a portion of the cavity with a curable modeling material, wherein the modeling material is in contact with the removable pin and the model support surface. The method further includes curing the modeling material and removing the mold member from the dental model base.

Another aspect of the present disclosure relates to a method of forming a dental model that includes providing a dental model base, a mold member, and a dental model forming machine. The dental model base includes a model support surface and at least one pin member extending from the model support surface, and the mold member defines a cavity. The method includes releasably mounting the mold member to the dental model base with the model support surface and pin member positioned in the cavity, filling the cavity with a curable modeling material, curing the modeling material to form a modeling blank that is mounted to the dental model base, removing the mold member from the dental model base, and forming a dental model from the modeling blank with the model forming machine.

Forming the dental model may include one of milling and laser cutting the dental model blank. The method may include creating a digital image of at least a portion of a person's teeth, and forming the dental model may include creating a replica of the at least a portion of a person's teeth from the digital image. The dental model base may include a removable mounting plate having the at least one pin member extending therefrom, and the modeling blank is mounted to the mounting plate.

Another method of present disclosure relates to a method of forming a dental model that includes providing a dental model base and a digital image of at least one tooth, the dental model base including at least one removable pin, delivering data representing the digital image to a rapid prototyping device, and forming a dental model on the dental model base with the rapid prototyping device.

The dental model base may include a plurality of removable pins arranged at spaced apart locations that represent average spacing of teeth. Forming the dental model may include depositing a plurality of layers of model material with the rapid prototyping device. The dental model base may include a mounting plate, the mounting plate having the at least one removable pin permanently mounted thereto and defining a model mounting surface, and forming the dental model base may include forming directly onto the model mounting surface.

The above summary is not intended to describe each arrangement or every implementation of the present disclosure. The figures and the detailed description that follow more particularly exemplify various aspects of the present disclosure.

BRIEF DESCRIPTION OF THE DRAWINGS

FIG. 20 is a perspective view of the alignment jig of FIG. 19 with the pin locator adjusted vertically relative to the dental model.

FIG. 21 is a perspective view of the alignment jig of FIG. 20 with markings added to the dental model and mounting plate.

FIG. 41A is a perspective view of the dental model base of FIG. 35 having a plurality of mounting pins positioned therein with the dental model base enclosed in a mold.

FIG. 41B is an exploded perspective view of the dental model base, mounting pins, and mold of FIG. 41A.

FIGS. 51A-51D are planned views of the dental model base and mounting plate of FIGS. 48-49.

FIGS. 61A-61F are plan views of the quadrant triple tray articulator of FIGS. 57-58.

FIG. 89 is a bottom perspective view of an example mold member in accordance with the present disclosure.

FIG. 90 is a bottom view of the mold member of FIG. 89.

FIG. 91 is a rear view of the mold member of FIG. 89.

FIG. 92 is a side view of the mold member of FIG. 89.

FIG. 97 is an exploded rear perspective view of another dental modeling assembly that includes the mounted molding block of FIG. 93.

FIG. 98 is an exploded front perspective view of the dental modeling assembly if FIG. 97.

FIG. 101 is an exploded rear view of the dental modeling assembly of FIG. 97.

FIG. 102 is an exploded front view of the dental modeling assembly of FIG. 97.

FIG. 119 is an exploded rear perspective view of another example dental modeling assembly that includes the mounted molding block of FIG. 116 in accordance with the present disclosure.

FIG. 120 is an exploded front perspective view of the dental mounted assembly of FIG. 119.

FIG. 121 is another exploded front perspective view of the dental mounting assembly of FIG. 119.

FIG. 122 is another exploded rear perspective view of the dental mounting assembly of FIG. 119.

FIG. 123 is an exploded rear view of the dental mounting assembly of FIG. 123.

FIG. 124 is an exploded front view of the dental mounting assembly of FIG. 119.

FIG. 129 is another exploded front perspective view of the mold and base assembly of FIG. 126.

FIG. 130 is an exploded side view of the mold and base assembly of FIG. 126.

FIG. 131 is a top view of the mold and base assembly of FIG. 126.

FIG. 132 is a front perspective view of another example mold member in accordance with the present disclosure.

FIG. 133 is a bottom view of the mold member of FIG. 132.

FIG. 134 is a front view of the mold member of FIG. 132.

FIG. 135 is a rear view of the mold member of FIG. 132.

FIG. 136 is a top view of the mold member of FIG. 132.

FIG. 137 is a pin hole layout for upper and lower arc teeth arrangements.

FIG. 138 is a pin hole layout with a linear array of pin holes determined by overlaying one of the pin hole layouts of FIG. 137.

Throughout the drawings, identical reference numbers designate similar, but not necessarily identical, elements.

BEST MODE(S) FOR CARRYING OUT THE INVENTION

Figure 1:
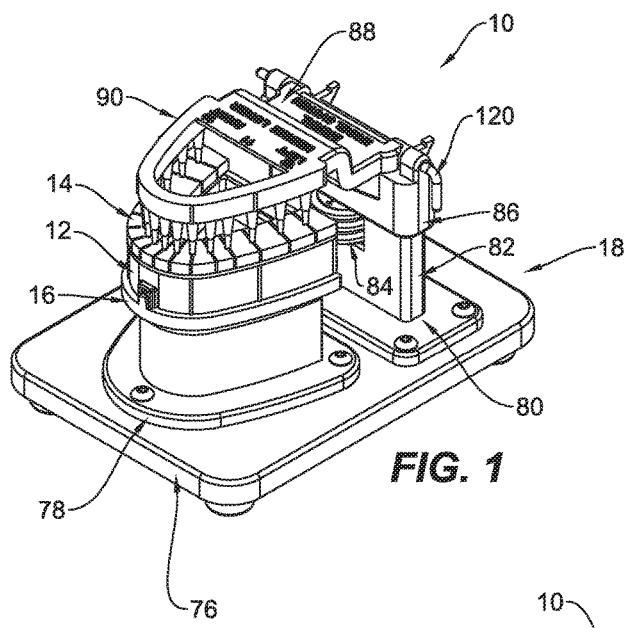
FIG. 1 is a top perspective view of an example dental modeling assembly in accordance with the present disclosure.
Figure 2:
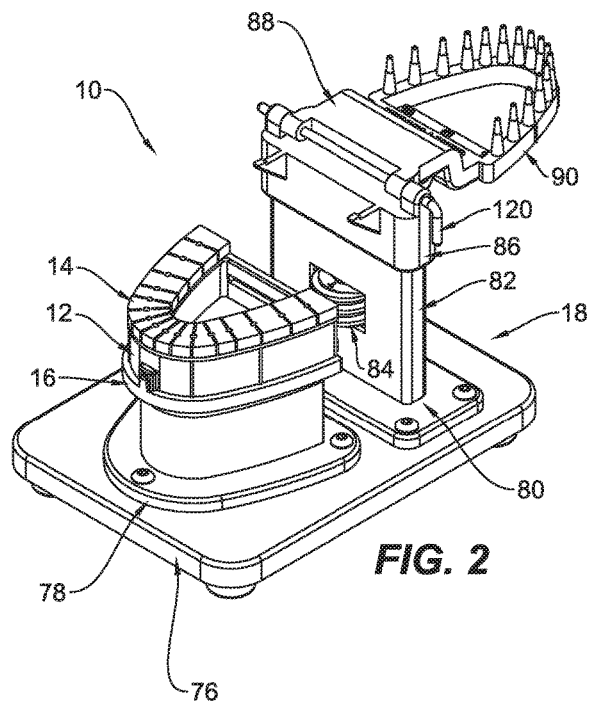
FIG. 2 is a top perspective view of the dental modeling assembly of FIG. 1.
Figure 3:
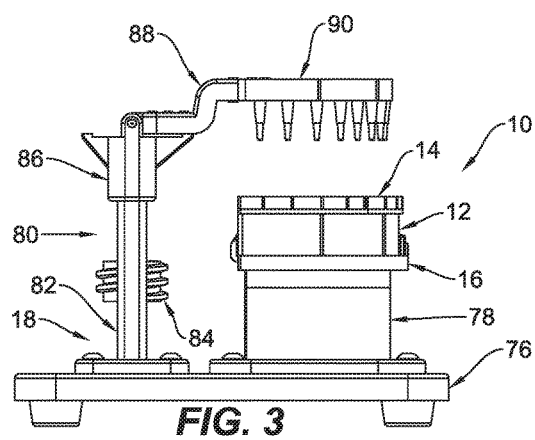
FIG. 3 is a left side view of the dental modeling assembly of FIG. 1.
Figure 5:
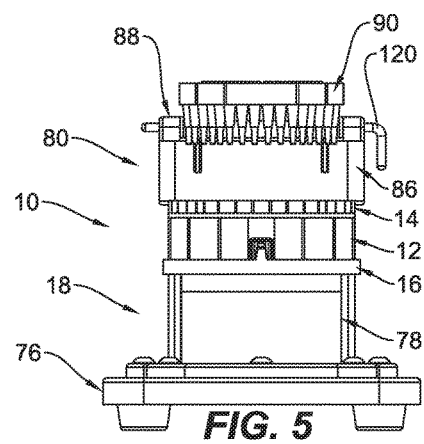
FIG. 5 is a front view of the dental modeling assembly of FIG. 1.
Figure 4:
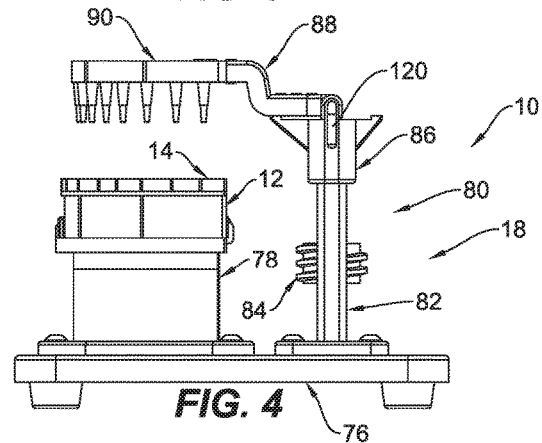
FIG. 4 is a right side view of the dental modeling assembly of FIG. 1.
Figure 6:
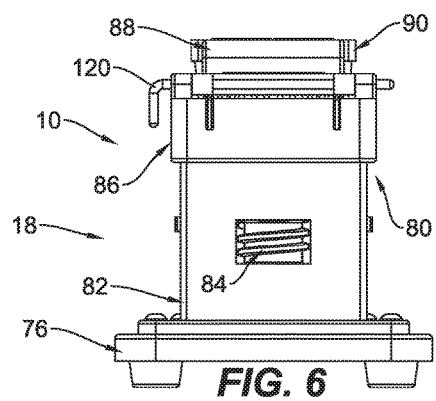
FIG. 6 is a rear view of the dental modeling assembly of FIG. 1.
Figure 8:
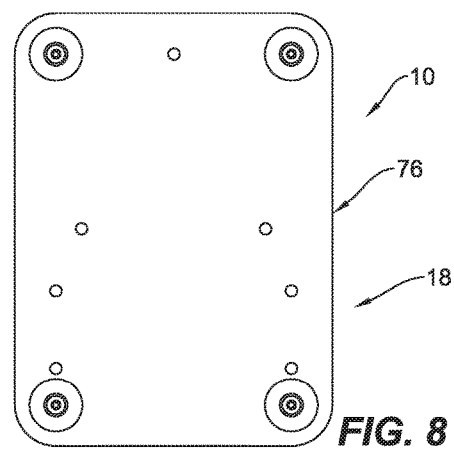
FIG. 8 is a bottom view of the dental modeling assembly of FIG. 1.
Figure 7:
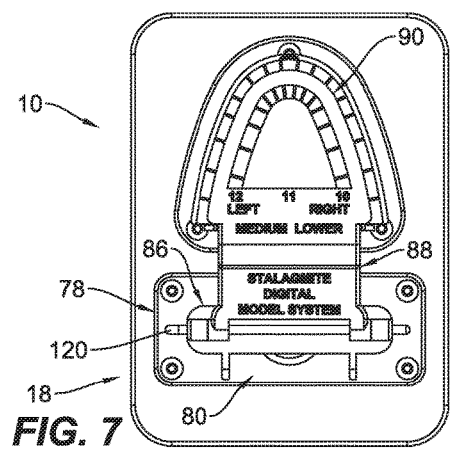
FIG. 7 is a top view of the dental modeling assembly of FIG. 1.

A model of a person's teeth (a "dental model") is commonly used in the dental industry for preparation of, for example, crowns, bridges, etc. The dental model typically has the same shape, size and spacing between teeth as the actual teeth represented by the model. The dental model is often mounted to a dental model base for improved ease in handling the dental model. Some types of dental model bases include apertures along a model support surface that are sized to receive dowel pins (also referred to herein as "dental pins"). The dowel pins, when inserted into the apertures, extend partially into the dental model base and partially into the dental model that is supported on the dental model base. Typically, at least one dowel pin is arranged on the dental model base in alignment with a particular tooth of the dental model. When individual teeth of the dental model are separated from adjacent teeth by, for example, cutting through the dental model, that tooth can be removed from the dental model base. The dowel pin attached to the removed tooth can be used to handle the removed tooth and can be used later to reposition the removed tooth on the dental model base at the same location.

The present disclosure is applicable to dental modeling systems used in the formation of dental models. An example dental modeling system includes an articulator associated with the dental modeling bases that can be used to position upper and lower sets of teeth relative to each other and provide some articulation between the upper and lower teeth. In one example, the dental modeling system includes dental model bases having integral articulator components. The dental modeling system may also include opposing bases.

Dental models can be formed in a variety of ways. One standard way of generating a dental model includes first taking an impression of a person's teeth by inserting a person's teeth into a mass of mold material to form an impression of the person's teeth. The impression is later filled with a curable moldable material, which when cured into a solid state results in the dental model. Methods exist for mounting a dental model formed from an impression of a person's teeth to a dental model base.

Recently, more advanced techniques for creating a dental model have been developed. One such technique includes scanning a person's teeth (or a model of a person's teeth) to create digital images of the person's teeth. The digital images are converted into a digital model. Electronic data representing the digital model is input into a milling machine that cuts the dental model from a block of model material. In another recently developed technique, the digital model of the person's teeth is input into a rapid prototyping or rapid manufacturing device, and the dental model is formed by depositing layers of material with the rapid prototyping device, which when built up over time results in a dental model.

The present disclosure relates in part to dental model bases, cured modeling blocks mounted to dental model bases (referred to herein as mounted modeling blocks), mold members used to create the cured modeling blocks, mold and base assemblies that include mold members and dental model bases, and dental modeling assemblies that include dental model bases, mold members and cured modeling blocks. The present disclosure also relates to the formation of a dental model directly onto a dental model base using rapid prototyping or rapid manufacturing techniques. The present disclosure also relates to formation of a dental model on a dental model base using milling, cutting or related processes to form a dental model in a block of cured modeling material that is mounted to dental model base. Some aspects of the present disclosure generally relate to the formation of dental models on a dental model base without the use of dental impressions. The present disclosure also relates to the formation of dental models on a dental model base using digital images of at least a portion of a person's teeth.

In at least some example, the dental model base includes a plurality of pre-positioned removable pins that are spaced apart based on average spacing of teeth common to large, medium, or small sized mouths. The removable pins may be coupled together as part of a mounting plate that is interposed between the dental model base and the dental model. The mounting plate may include a plate portion, which interconnects the removable pins and provides a mounting surface configured to support the dental model. The dental model may be connected to the mounting surface of the plate portion using, for example, an adhesive or other bonding agent. The removable pins extend from the plate portion in an opposite direction. The removable pins extend into pin apertures of the dental model base as part of releasable mounting the dental model and mounting plate to the dental model base.

The bonding agent may comprise, for example, an adhesive material such as cyanoacrylate, polyurethane, epoxy or any other suitable bonding agent.

In some examples, the modeling blocks mentioned above may be directly formed on the mounting plate, and the dental model is formed from the modeling block. In other examples, the dental model is formed directly on the mounting plate using, for example, rapid prototyping or rapid manufacturing technique.

Although many of the examples disclosed herein relate to the formation of a dental model directly on a dental model base, it may be possible to create the dental model in a separate step using, for example, rapid prototyping or milling based on a digital image of a person's teeth, and later mounting the completed dental model to a dental model base. The dental model base to which the completed dental model is mounted in a separate step may include, for example, a plurality of removable dowel pins that are positioned on the dental model base at average locations for a particular mount size (i.e., small, medium, and large mouth sizes). The dowel pins may be pre-positioned at such average locations by the formation of an array of apertures on the dental model base that represent the average location of teeth. In some cases, the dowel pins may be permanently attached to the dental model base, while in other cases at least some of the dowel pins may be removably mounted to the dental model base. As discussed above, the dowel pins may be connected together with a plate portion of a mounting plate so that the dowel pins can be mounted to and removed from the dental model base concurrently as a single unit. The dowel pins may include a tapered portion that facilitates mounting and dismounting of the dowel pins from the dental model base. The dowel pins may also include an attachment portion, which may include a knurled surface, for connecting the dowel pins directly to the dental model or to the plate portion of the mounting plate. The dental model bases may include at least a portion of an arc shape and the dowel pins are arranged along at least a portion of the arc. In other examples, the dental model base is generally linear shaped and includes a generally linear array of dowel pins and/or apertures sized to receive dowel pins.

The use of dental model bases having pre-positioned dowel pins arranged at average locations for teeth of a given mouth size with the advanced dental modeling techniques available (i.e., rapid prototyping and milling based on a digital image of the person's teeth without the use of an impression) is an advance in the art. The use of adhesives and other bonding agents to connect a pre-formed dental model, which is formed using any of a number of forming techniques, including impressionless forming techniques, to an arrangement of removable pins arranged at average locations for teeth of a given mouth size is also an advance in the art. A still further advance is the use of an alignment jig to orient the pre-formed dental model to the dental model base and/or the mounting plate discussed above is also an advance in the art. The alignment jig may provide consistent placement of dental models on dental model bases to provide improved articulation of mating (i.e., upper and lower) dental models. While the present disclosure should not be so limited, an appreciation of various aspects of the present disclosure will be gained through a discussion of the examples provided below.

Referring now to FIGS. 1-11, an example dental modeling assembly 10 is shown including a dental model base 12, a mounting plate 14, an attachment plate 16 and an alignment jig 18. The mounting plate 14 is receptive of a dental model of a person's teeth such as, for example, a full arc or a portion of an arc of a person's upper or lower teeth. The mounting plate 14 is removably mounted to the dental model base 12. The dental model base 12 is releasably mounted to the alignment jig 18 with the attachment plate 16. The alignment jig 18 may operate to align the dental model relative to the mounting plate 14 to provide consistent placement of the dental model relative to dental model bases using the alignment jig 18. This consistent placement may be helpful in providing proper articulation between two sets of dental models such as, for example, upper and lower dental models from the same person.

The mounting plate may include a plurality of mounting pins, which may also be referred to as tapered pins or removable tapered pins, which extend into the dental model base 12 to provide attachment there between. The mounting pins may be arranged at average locations of teeth for either the upper or lower portion of a person's mouth and based on the size of the person's mouth (e.g., small, medium or large). After mounting the dental model to the mounting plate 14, an operator may cut between individual teeth of the dental model and cut through the mounting plate such that individual teeth, or groups of teeth of the dental model are carried by a portion of the mounting plate 14 and a separate mounting pin is associated with each tooth.

The alignment jig 18 may be especially useful for mounting a dental model to a dental model base when the dental model is formed separately and independent of the dental model base by any of a number of different modeling processes. Some example modeling processes include impressionless modeling, which involve, for example, rapid prototyping and rapid manufacturing buildup of the tooth based on a 3D image of the teeth collected by, for example, a digital scanner. Another example impressionless method includes milling, cutting or otherwise creating a dental model from a block of cured model material also based on a 3D image of a person's teeth collected by, for example, a digital scanner. The model may be formed using traditional methods such as taking an impression of a person's teeth using a tray of curable material that a patient bites into to form a negative impression, and the negative impression is later filled with a curable modeling material to form the dental model. After the dental model is formed using one of these methods, the dental model is mounted to the dental model base or a mounting plate that is pre-mounted to the dental model base.

The dental model base 12 and mounting plate 14 may be used independent from the alignment jig 18 as part of an impressionless modeling system. For example, a rapid prototyping or rapid manufacturing method may be used to build up and create a dental model directly on the mounting plate 14 or directly on the dental model base 12 when the plurality of mounting pins are pre-positioned in the dental model base 12. In another example, a block of cured modeling material is attached to the mounting plate 14 using a bonding agent such as adhesive, or the cured block of modeling material is mounted directly to the dental model base 12, which has mounted thereto the plurality of mounting pins. A method such as milling, cutting or forming device may be used to create the dental model from the block of modeling material.

The dental model base 12 and at least the mounting pins of the mounting plate 14 may provide advantages of the systems and methods disclosed in U.S. Pat. No. 7,108,507 and U.S. Patent Publication No. 2006/0281043, which are incorporated herein in their entireties by this reference. In some examples, the combination of the dental model base 12 and the mounting plate 14 is referred to as a dental model base or a dental model base assembly.

Figure 37:
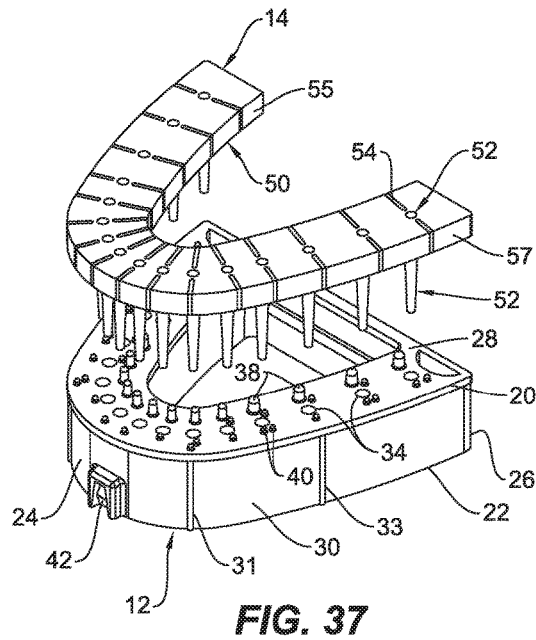
FIGS. 37-38 are exploded perspective views of the dental model base and mounting plate of FIGS. 35-36.
Figure 38:
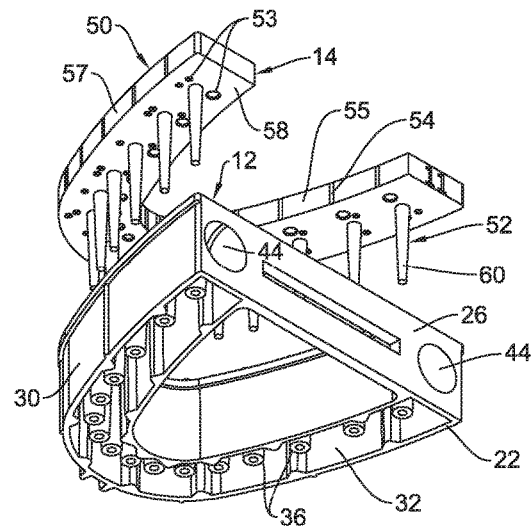
Figure 39A:
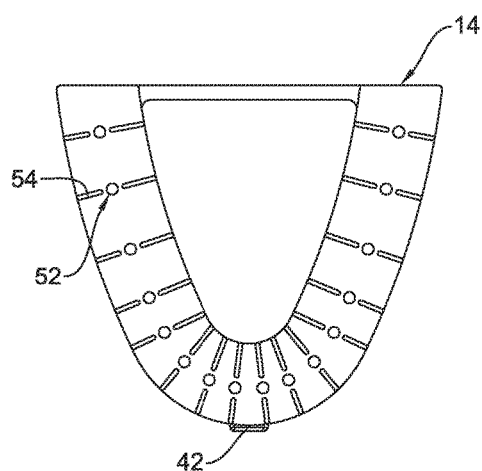
FIGS. 39A-39F show plan views of the assembled dental model base and mounting plate of FIGS. 35-36.
Figure 39B:
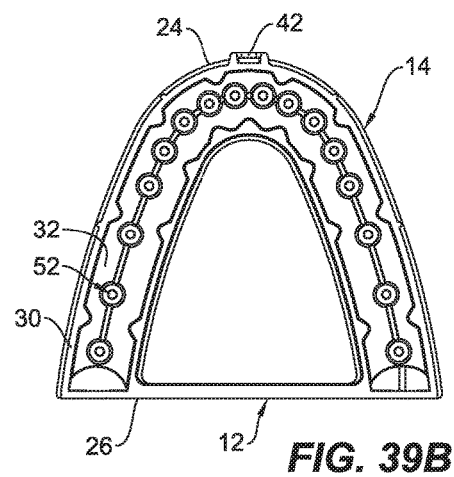
Figure 39C:
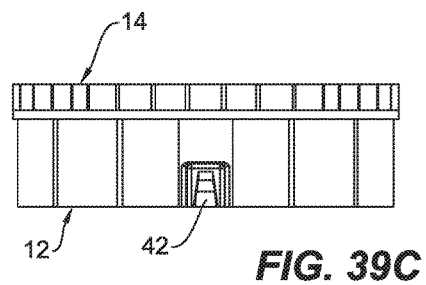
Figure 39D:
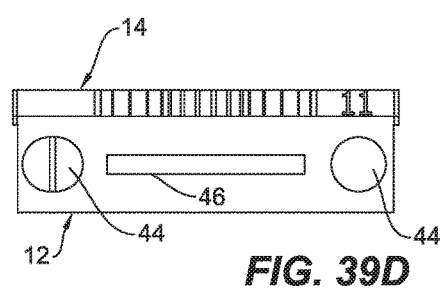
Figure 39E:
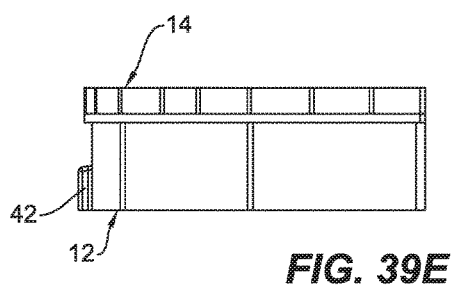
Figure 39F:
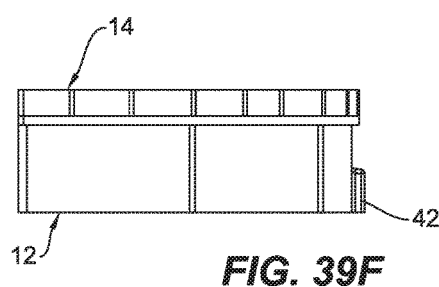
Figure 40A:
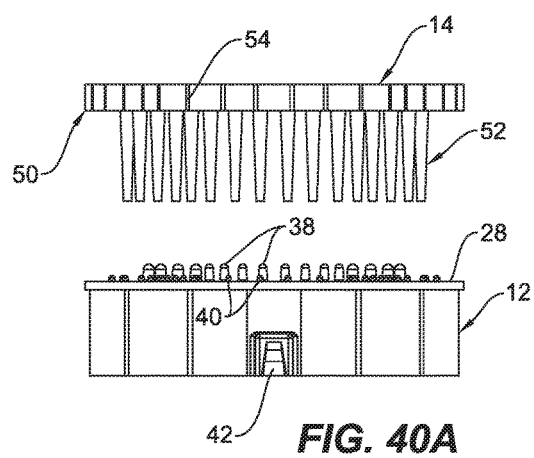
FIGS. 40A-40D are plan views of the dental model base and mounting plate of FIGS. 37-38.
Figure 40C:
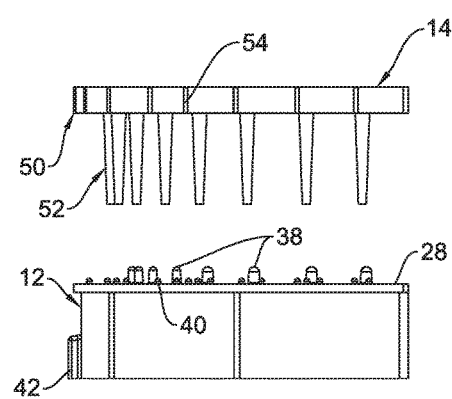
Figure 40B:
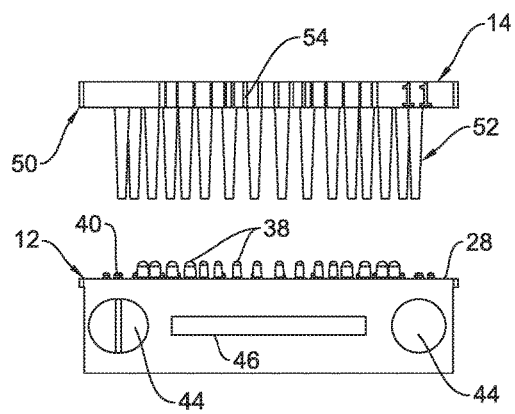
Figure 40D:
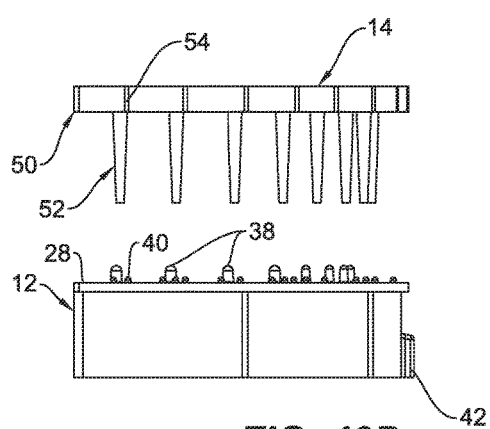
Figure 42:
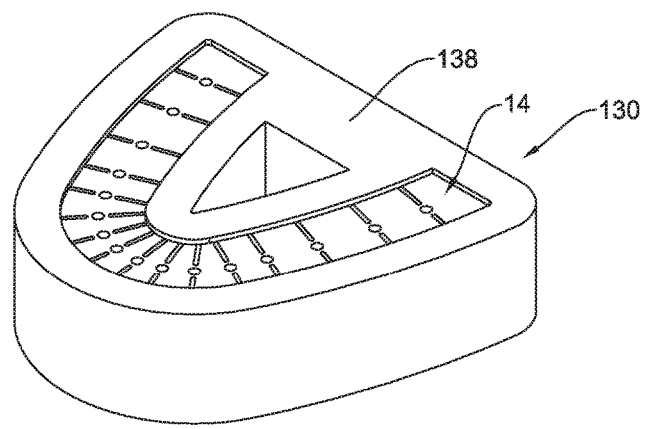
FIGS. 42-43 are perspective views of the assembly of FIG. 41A showing the mold filled to form a plate portion of the mounting plate.
Figure 44:
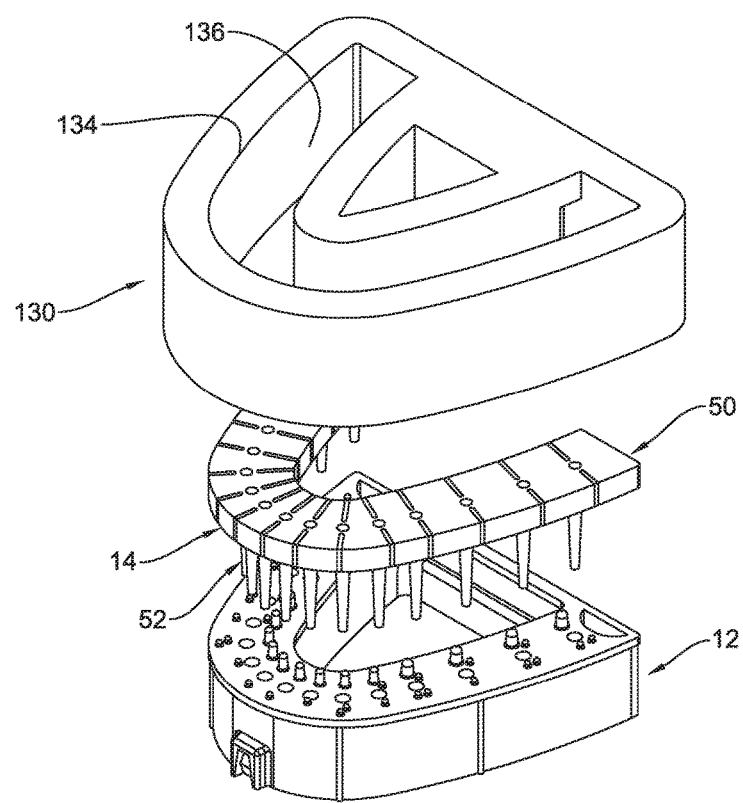
FIGS. 44-45 are exploded perspective views of the assemblies of FIGS. 42-43 showing the formed mounting plate.
Figure 43:
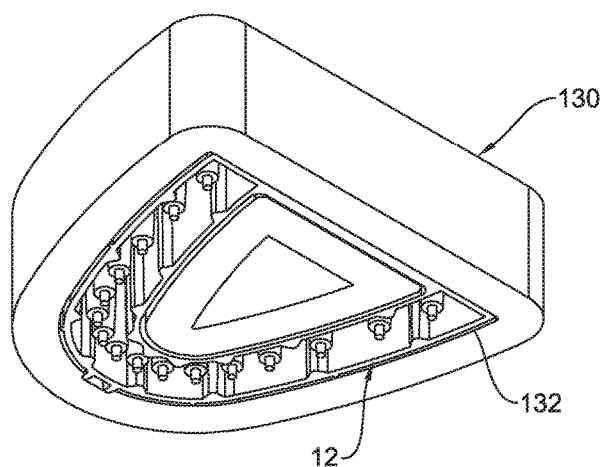
Figure 45:
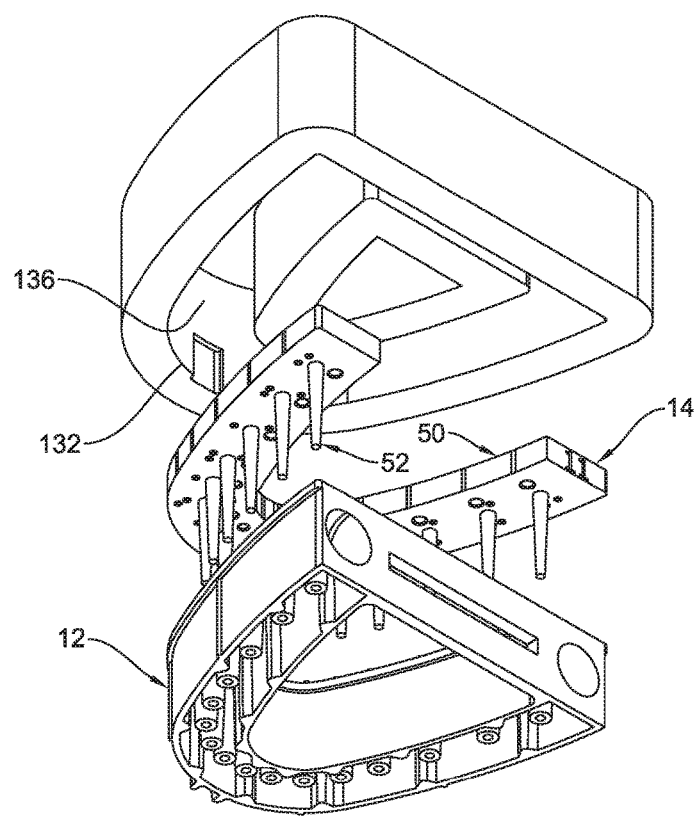
Figure 46:
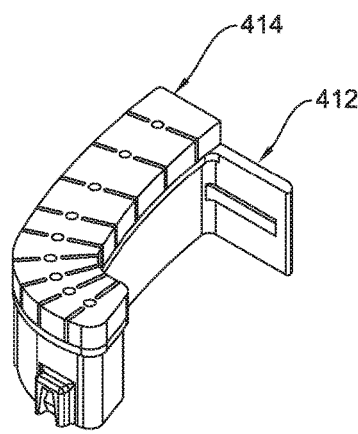
FIGS. 46-47 are perspective views of another example dental model base and mounting plate assembled together.
Figure 48:
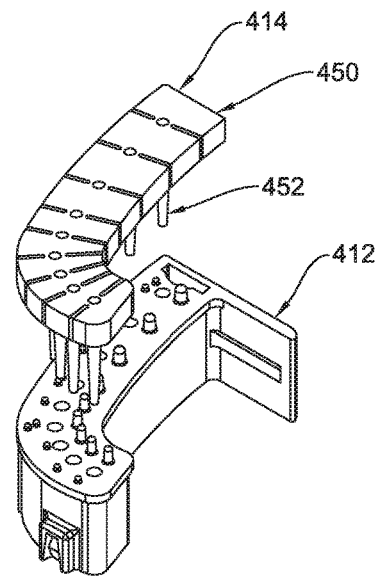
FIGS. 48-49 are exploded perspective views of the dental model base and mounting plate of FIGS. 46-47.
Figure 47:
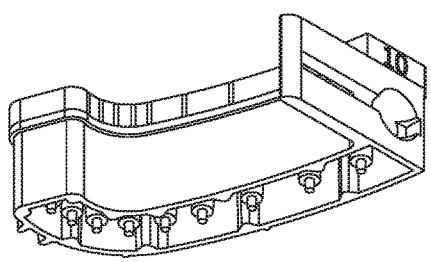
Figure 49:
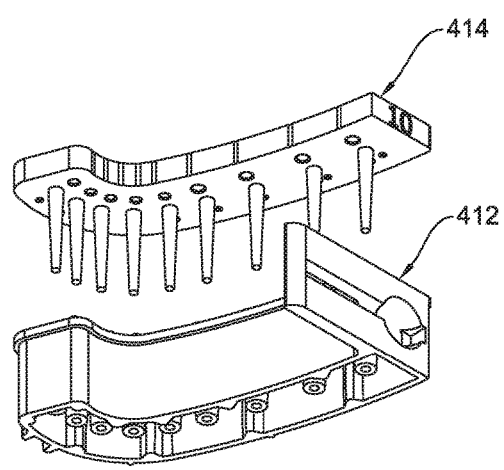
Figure 50A:
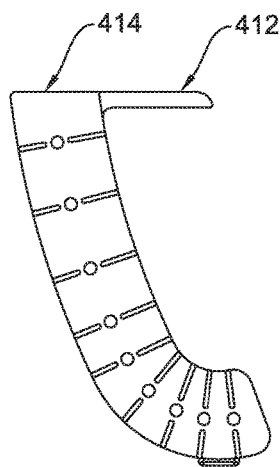
FIGS. 50A-50F are plan views of the dental model base and mounting plate of FIGS. 46-47.
Figure 50C:
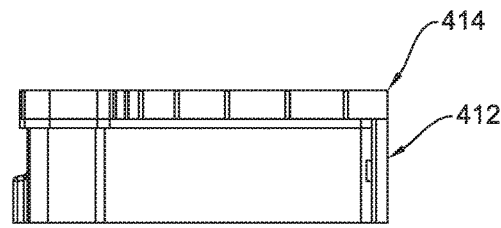
Figure 50D:
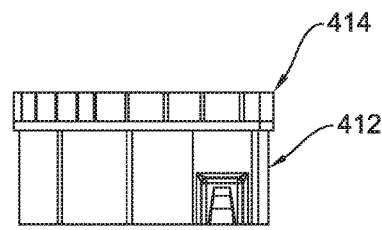
Figure 50E:
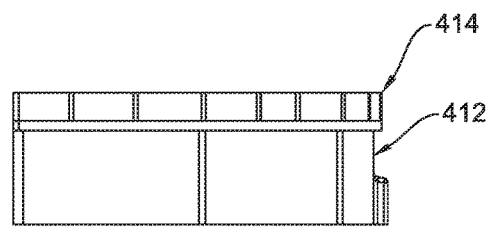
Figure 50B:
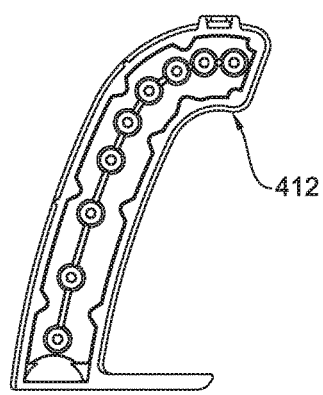
Figure 50F:
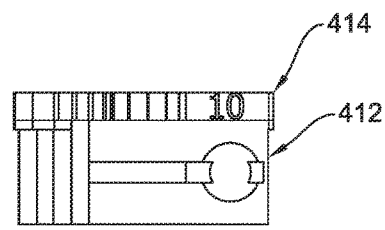

Referring to FIGS. 37 and 38, the dental model base 12 includes a top side 20, a bottom side 22, a front end 24, a rear end 26, a model support surface 28, a side wall 30, and a cavity 32. FIGS. 35-36 and 39A-40D show additional views of the dental model base 12. A plurality of pin apertures 34 are formed on the model support surface 28 and are aligned with a plurality of pin support protrusions 36 that extend into the cavity 32. The indexing members 38, 40 are positioned on the model support surface 28. A different size and number of indexing members 38 may be associated with each pin aperture 34 as compared to the size and number of the indexing members 40.

The dental model base 12 may also include a latch feature 42 positioned at the front end 24 and at least one socket feature 44 positioned at the rear end 26. The latch 42 and socket 44 may interface with features of the attachment plate 16 to provide a quick release mount of the dental model base 12 to the attachment plate 16 and to whatever device or structure the attachment plate 16 is mounted to (e.g., the alignment jig 18 or an articulator structure). A slot 46 may also be formed in the rear end 26. The slot 46 may be used to mount the dental model base 12 to a support structure such as, for example, an articulator.

Figure 36:
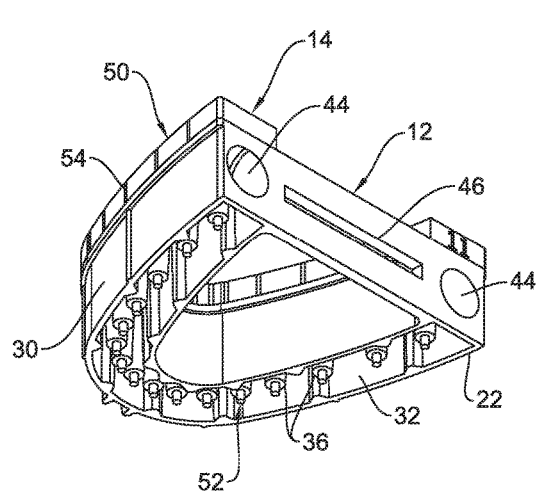

The pin support protrusions 36 may define a channel or bore, which has a tapered construction and is sized to receive the mounting pins of the mounting plate 14 described above. The pin support protrusions 36 may have a length within cavity 32 that is less than a distance that the mounting pins extend so that distal tips of the mounting pins protrude from a distal open end of the pin support protrusions 36, as shown in FIG. 36. This arrangement provides exposure of a portion of the mounting pins so that the mounting pins may be more easily removed by applying an axial force to the exposed portion of the mounting pins.

The dental model base 12 may also include markers 31, 33 on the side wall 30 (see FIG. 37). The marker 31 may be aligned with a position of a cuspid tooth of the dental model, and the marker 33 may be aligned with a first molar of the dental model. The markers 31, 33 are aligned with an pin aperture 34 and pin support protrusion 36 associated with the cuspid and first molar.

Referring again to FIGS. 37 and 38, the mounting plate 14 includes a plate portion 50, a plurality of mounting pins 52, and a plurality of pin markings 54. The plate portion 50 includes top and bottom surfaces 56, 58. The mounting pins 52 may extend from the bottom surface 58 and include a tapered portion 60. The tapered portion 60 extends into and mates with the tapered internal bore of the pin apertures 34 and pin support protrusions 36 of the dental model base 12.

The pin markings 54 may extend away from the mounting pins 52 to be exposed along the top surface 56 and possibly along the opposing inner and outer side surfaces 55, 57. The pin markings 54 may provide a visual indicator of a position of each of the mounting pins 52 even when the top surface 56 is at least partially covered with a dental model.

During formation of the mounting plate 14, the top surface 56 may be machined to achieve a desired thickness of the plate portion 50. The machining may include, for example, milling to remove a portion of the plate portion 50 and a portion of the mounting pins 52. This machining may result in the mounting pins 52 being exposed along the top surface 56. Typically, the mounting pins 52 comprise a different material from the plate portion 50. The difference in materials between the plate portion 50 and the mounting pins 52 may provide a visual indicator of the positions of the mounting pins 52 on the plate portion 50, which may assist in arranging a dental model on the mounting plate 14 with or without the pin markings 54.

The pin markings 54 may be formed using, for example, a stenciling method that applies a visual indicator along an outer surface of the plate portion 50. Other methods may be used to form pin markings 54 including, for example, forming a slight protrusion or recess, embedding a member within the material of the plate portion 50, or providing the pin markings 54 along the bottom surface 58 instead of the top surface 56 and forming the plate portion 50 out of a transparent material that permits visualization of the pin markings 54 from the top surface 56.

Figure 11:
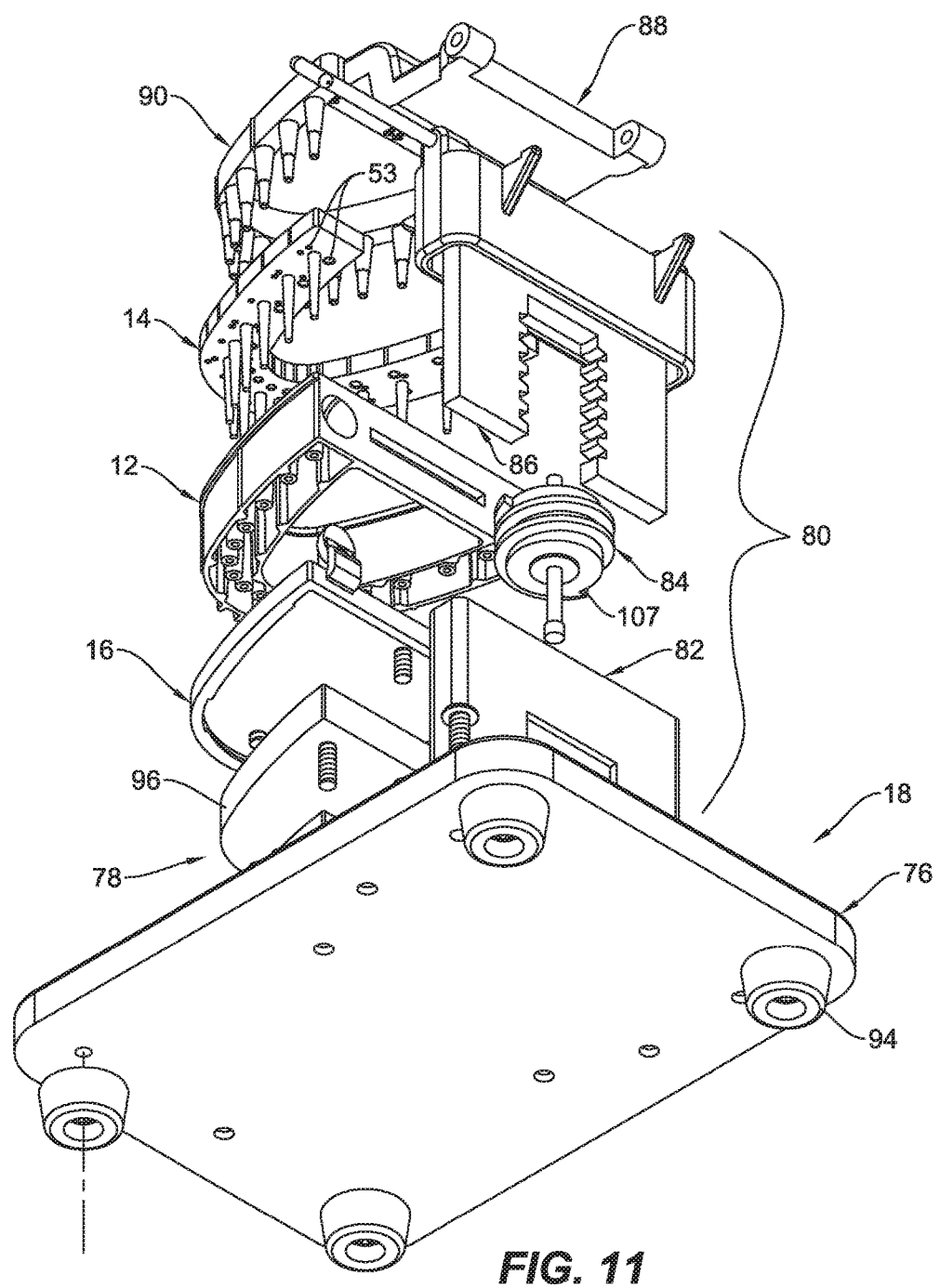
FIG. 11 is an exploded bottom perspective view of the dental modeling assembly of FIG. 1.

The mounting plate 14 may also include a plurality of indexing apertures 55 (see FIG. 11). The indexing apertures 55 may be aligned with the plurality of indexing members 38, 40 positioned on the top surface of the dental model base 12. In at least one example, the indexing apertures 55 are formed concurrently with forming the plate portion 50 directly on the top surface of the dental model base 12, or a surface that represents the top surface and indexing numbers 38, 40 of the dental model base 12. The arrangement of the indexing members 38, 40 and the indexing apertures 55 is unique for each one of the pin apertures 34 and mounting pins 52. This unique arrangement of indexing members and indexing apertures substantially eliminates the possibility of positioning a mounting pin 52, and associated portion of the dental model, in the wrong pin aperture 34.

The attachment plate 16 is now described with reference to FIGS. 9-11. The attachment plate 16 includes a top surface 64, a bottom surface 66, a latch member 68, at least one ball attachment member 70, fastener apertures 72, and a plurality of first fasteners 74. The top surface 64 is configured to receive and support the dental model base 12. The bottom surface 66 rests against a pedestal feature of the alignment jig 18. The latch member 68 engages the latch 42 of the dental model base 12, and the ball attachment member 70 engages the sockets 44 of the dental model base 12. The latch member 68 and ball attachment member 70 may provide a releasable (e.g., snap-fit) connection of the dental model base 12 to the attachment plate 16. The first fastener 74 may extend through the fastener aperture 72 to provide a releasable connection of the attachment plate 16 to the alignment jig 18. Other attachment features may be possible to releasably mount the attachment plate 16 to the alignment jig 18. The attachment plate 16 may be configured to mount to other devices such as, for example, pouring jigs and articulators. Furthermore, different types of releasable connection features may be used in place of latch member 68 (e.g., snap-fit) and ball attachment member 70 (e.g., ball and socket) to provide a quick release attachment of the dental model base 12 to the attachment plate 16 or the alignment jig 18.

Referring again to FIGS. 1-11, generally, the alignment jig 18 includes a base 76, a pedestal 78, a support stand 80, and a pin locator 90. The base 76 supports the pedestal 78 and support stand 80. The support stand 80 includes a housing 82, a screw 84, a slide 86, and a support arm 88. The support stand 80 is adjustable to alter a position of the pin locator 90 relative to the pedestal 78, which supports the dental model base 12, mounting plate 14 and attachment plate 16.

The base 76 includes a top surface 92 to which the pedestal 78 and support stand 80 are mounted. The base 76 also includes a plurality of support pads 94 along a bottom surface thereof. The support pads 94 may provide a high friction interface with a support surface, such as a countertop, to limit movement of the alignment jig 18 relative to the support surface during use.

Figure 9:
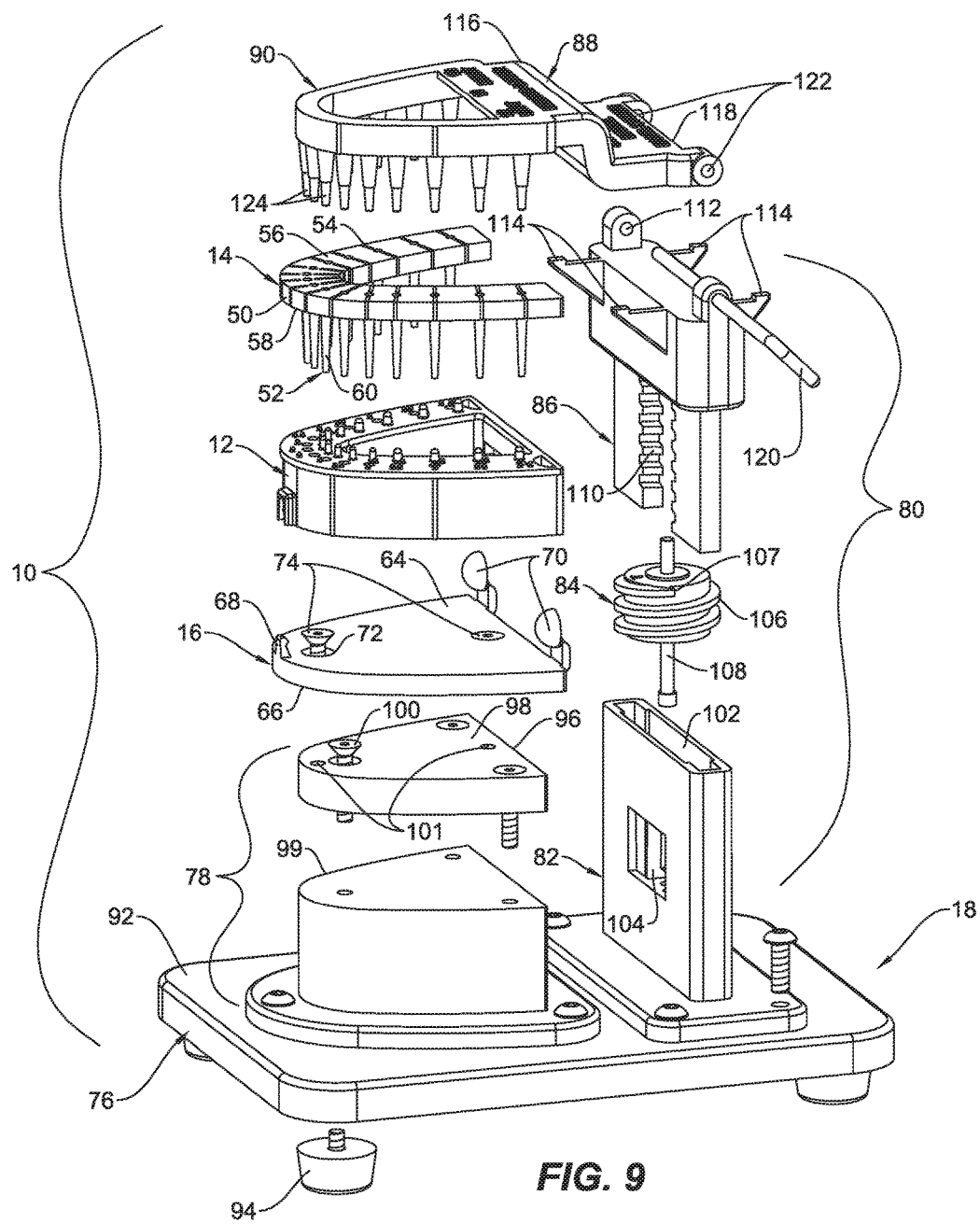
FIG. 9 is an exploded top perspective view of the dental modeling assembly of FIG. 1.
Figure 10:
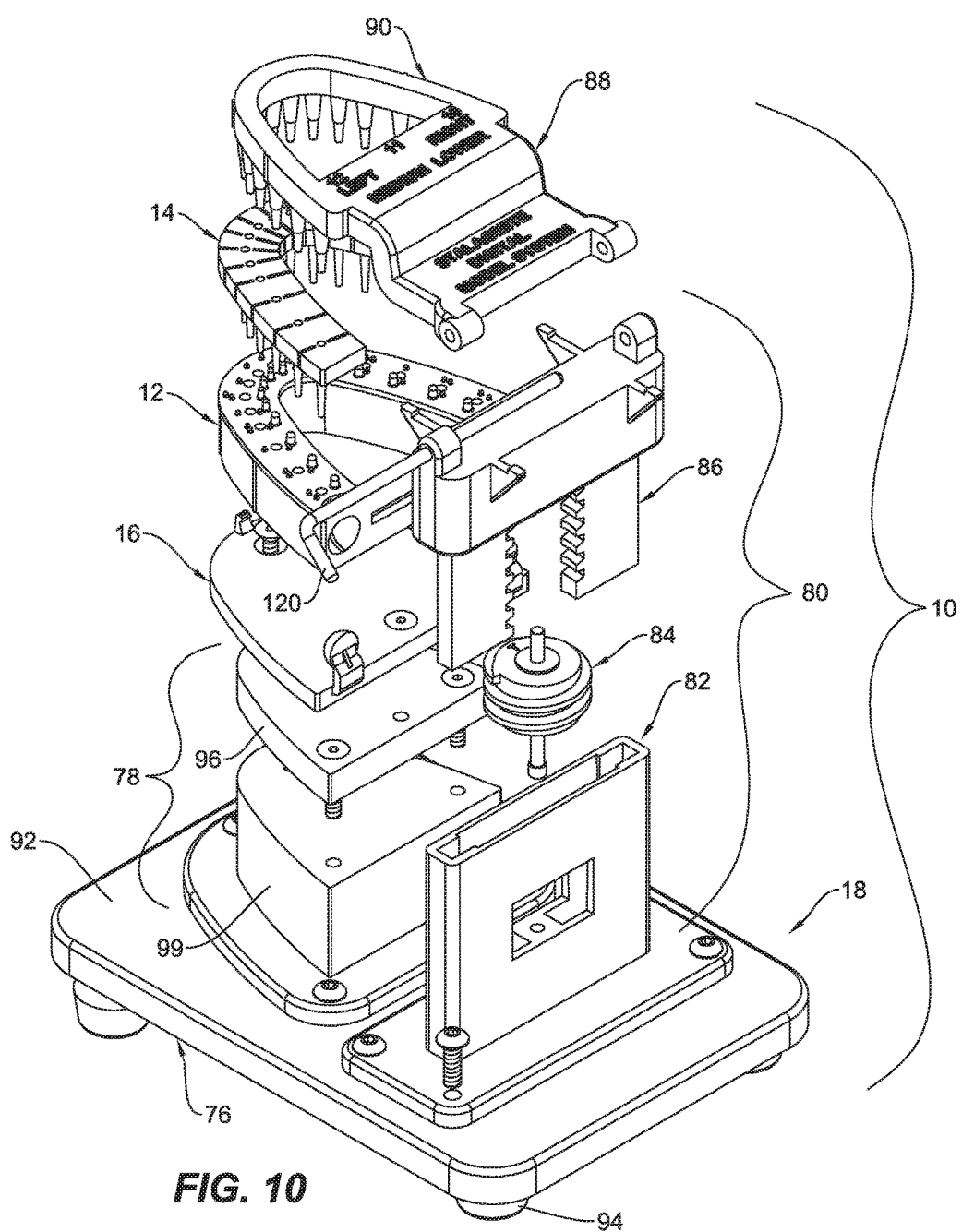
FIG. 10 is another exploded top perspective view of the dental modeling assembly of FIG. 1.

The pedestal 78 includes a pedestal plate 96, a mounting surface 98, a base 99 and a plurality of pedestal fasteners 100 (see FIGS. 9-11). The base 99 may comprise different materials from the pedestal plate 96. In one example, the base 99 comprises a polymer material and the pedestal plate 96 comprises a metal material. The pedestal plate 96 provides an interface for attaching the attachment plate 16 to the alignment jig 18. The pedestal fasteners 100 may be used to secure the pedestal plate 96 to the base 99. The pedestal plate 96 may include the mounting surface 98 and a plurality of fastener openings 101 configured to receive the first fasteners 74 of the attachment plate 16.

The housing 82 includes a top opening 102 and a screw opening 104 (see FIGS. 9-11). The top opening 102 is sized to receive the slide 86. The screw opening 104 provides access to the screw 84 when assembled. The screw may include a plurality of screw threads 106 and an axle member 108. The screw 84 may be assembled with the housing 82 by removing the axle 108 from the screw 84, positioning the screw 84 within the screw opening 104, and advancing the axle 108 up through a bottom surface of the housing 82 when the housing 82 is detached from the base 76. This arrangement may provide secure attachment of the screw 84 to the housing 82 until the housing 82 is removed from the base 76.

The slide 86 shown in FIGS. 9-11 includes a plurality of slide threads 110, an axle opening 112 and a plurality of stop or pad members 114. The screw threads 106 of the screw 84 interface with the slide threads 110. Rotating the screw 84 moves the slide 86 up and down relative to housing 82. The screw threads 106 of screw 84 may include stop surfaces 107 (see FIGS. 9 and 11), which provide maximum raised and lowered positions of the slide 86 relative to housing 82.

The axle openings 112 are sized to receive an axle pin 120 to secure the support arm 88 to the slide 86. The stop members 114 provide position stops for the support arm 88, which is rotatable between a first position shown in FIG. 1 and arranged adjacent to the mounting plate 14 and a second or removed position shown in FIG. 2 rotated away from the mounting plate 14. The stop members 114 may define a 180° rotation angle for the support arm 88. The stop members 114 may be positioned at any desired location or angle to define a different rotation angle of the support arm 88.

While a portion of the slide 86 is shown extending into the housing 82 to provide contact with the screw 84, other embodiments are possible wherein the slide 86 extends along an exterior of the housing 82 and provides a similar function. In one example, the screw 84 may be mounted to the slide 86 rather than being mounted to the housing 82 so as to move vertically with the slide 86 relative to housing 82. In other arrangements, different adjusting features may be used to move the support arm 88 vertically relative to pedestal 78. In some examples, the pedestal 78 may include features that provide vertical movement of the dental model base 12 and mounting plate 14 relative to the pin locator 90 carried by the support arm 88.

The support arm 88 includes distal and proximal ends 116, 118, the axle pin 120 mentioned above, and a pin opening 122 (see FIGS. 9-11). The pin locator 190 includes a plurality of locator pins 124. The locator pins 124 extend in the same direction and typically have the same size and shape and extend the same distance. The pin locator 90 is mounted to the distal end 116 of support arm 88. The support arm 88 is connected to the slide 86 at the proximal end 118.

The axle pin 120 extends through the axle openings 112 of the slide 86 and through the pin openings 122 of the support arm 88 to provide a pivotal connection between the support arm 88 and the slide 86.

In some arrangements, the support arm 88 is formed integral with the pin locator 90. In other arrangements, the pin locator 90 is formed separate from the support arm 88 and assembled thereto using a fastener or other attachment feature.

The pin locator 90 may have a construction that matches the size of the dental model base 12 and mounting plate 14. For example, when a dental model base 12 and mounting plate 14 having a medium size for an upper set of teeth, the pin locator 90 also has a medium upper size. As discussed above, the attachment plate 16 may also have a matching size (e.g., a medium upper size or a size configured to accommodate a medium upper dental model base 12). An operator may check the size of the pin locator 90 to make sure it matches the size of the dental model base 12 and mounting plate 14 by rotating the pin locator 90 into the position shown in FIG. 1 and lowering the slide 86 until the locator pins 124 touch the top surface of the mounting plate 14. The locator pins 124 should align with the mounting pins 52 (e.g., substantially cover the mounting pins 52) along the top surface 56 of the plate portion 50. If the locator pins 124 do not properly align, the pin locator 90 may be replaced with the proper size to match the size of the dental model base 12 and mounting plate 14.

Figure 12:
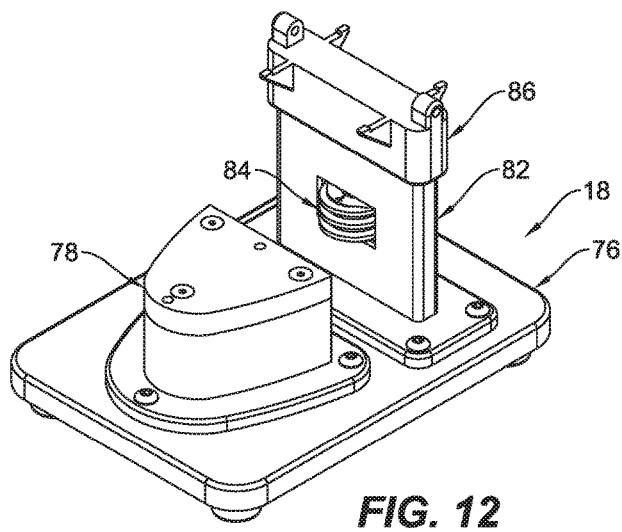
FIG. 12 is a perspective view of a portion of an alignment jig of the dental modeling assembly of FIG. 1.
Figure 13:
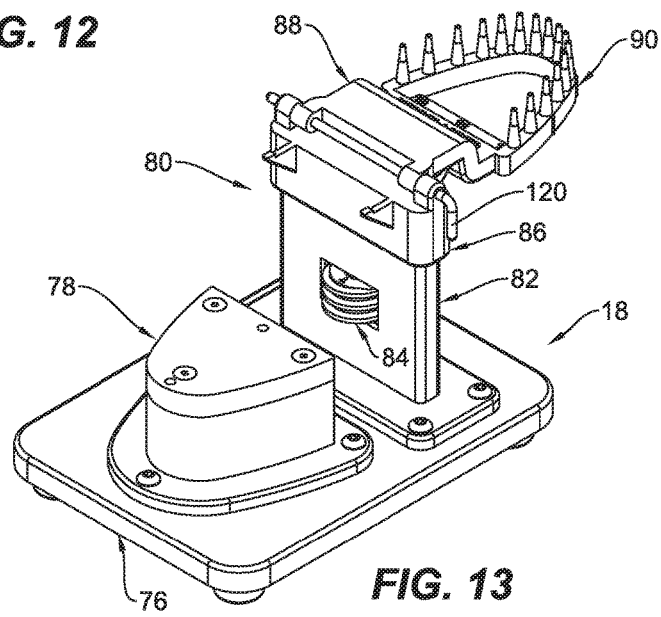
FIG. 13 is a perspective view of the alignment jig of FIG. 12 having additional features.

Referring now to FIGS. 12-26, an example method of mounting a dental model to a dental model base and forming individual teeth models that can be removably mounted to the dental model base is described in detail. FIG. 12 shows the alignment jig 18 in its most basic form. The screw 84 is adjusted to elevate the slide 86 to its maximum height position. A pin locator 90 and associated support arm 88 are selected to match the size for the dental model that is being handled. For example, if the dental model is a medium upper, the pin locator 90 is selected to be a medium upper pin locator. The support arm 88, which carries the pin locator 90, is mounted to the slide 86 using the axle pin 120 as shown in FIG. 13. The support arm 88 is rotated into the second or removed position away from the pedestal 78.

Figure 14:
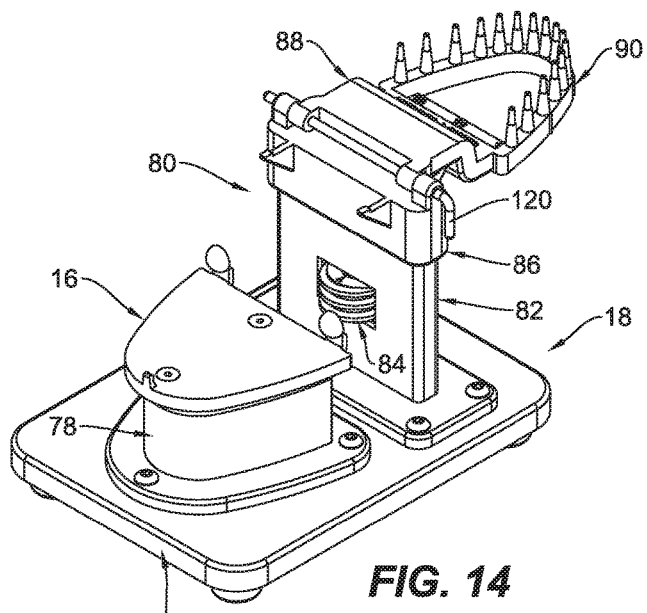
FIG. 14 is a perspective view of the alignment jib of FIG. 13 having additional features.

Referring to FIG. 14, the attachment plate 16 is selected to match the size of the dental model (e.g., a medium upper size). The first fasteners 74 are used to connect the attachment plate 16 to the pedestal plate 96 with pedestal 78.

Figure 15:
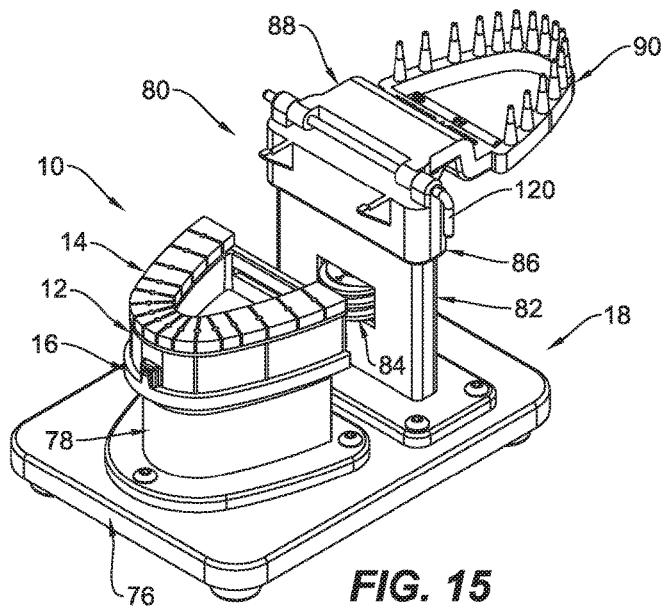
FIG. 15 is a perspective view of the alignment jig of FIG. 14 having a dental model base and mounting plate mounted thereto.
Figure 16:
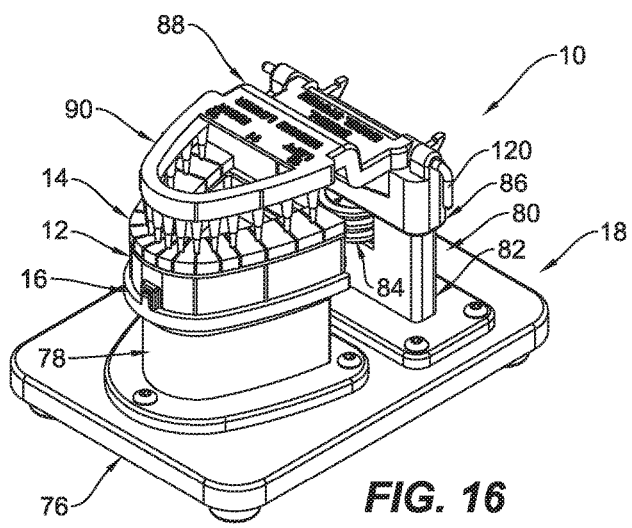
FIG. 16 is a perspective view of the alignment jig of FIG. 15 with a pin locator arranged adjacent to the mounting plate.
Figure 17:
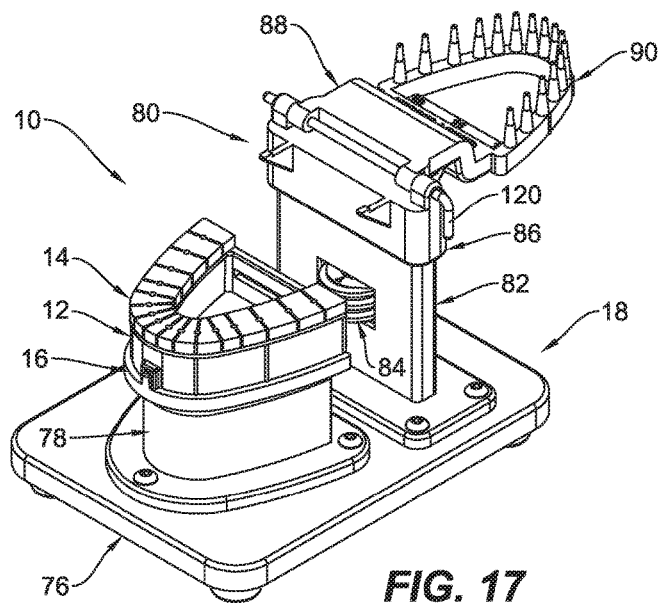
FIG. 17 is a perspective view of the alignment jig of FIG. 16 with the pin locator removed from the mounting plate.

Referring to FIG. 15, the dental model base 12 and mounting plate 14 are selected to match the size of the dental model (e.g., a medium upper), and the mounting plate 14 is mounted to the dental model base 12 by inserting the mounting pins 52 into the pin apertures 34. The dental model base 12 is mounted to the attachment plate 16 using an interface between the latch 42 and latch member 68 and the socket 44 with the ball attachment member 70. Referring to FIG. 16, the support arm 88 is rotated into the first or adjacent position, which is vertically above the mounting plate 14, to confirm that the pin locator 90 and the mounting plate 14 have a mating size. The screw 84 may be operated to adjust the slide 86 downward to contact the locator pins 124 against the top surface of the mounting plate 14. The locator pins 124 should align with the mounting pins 52 and the pin markings 54. Once the mating size is confirmed, the support arm 88 is rotated back to the second or removed position shown in FIG. 16 and the slide 86 is adjusted vertically upward (e.g., to its maximum height position).

Figure 18:
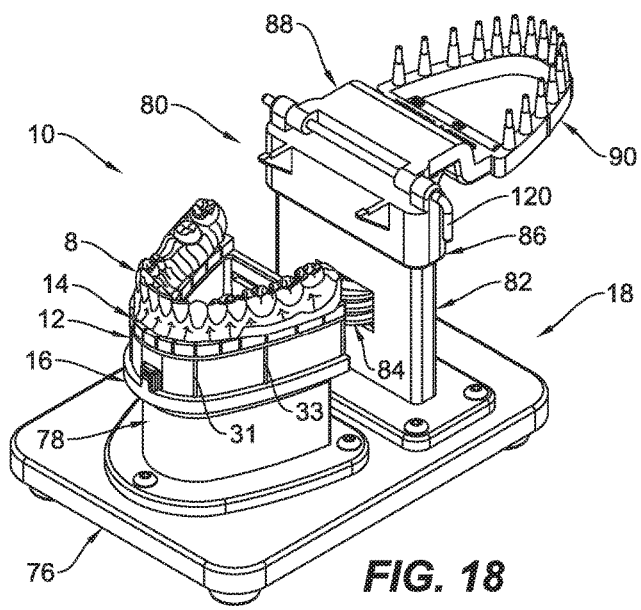
FIG. 18 is a perspective view of the alignment jig of FIG. 17 with a dental model positioned on the mounting plate.

Referring to FIG. 18, a dental model 8 is positioned on top of the mounting plate 14. A rough adjustment of the dental model 8 may be performed to align the cuspid with the marking 31 and the first molar with the marking 33. The operator may check to confirm whether there is excess gum portion of the dental model that is extending over the peripheral edges of the mounting plate 114 and that needs to be trimmed.

Figure 19:
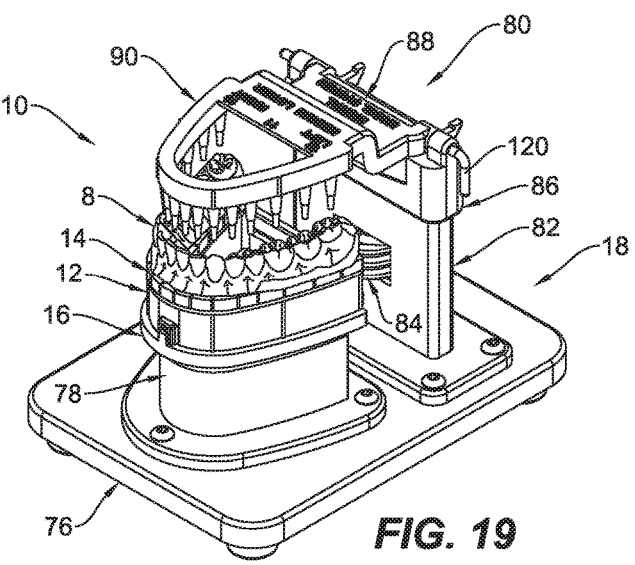
FIG. 19 is a perspective view of the alignment jig of FIG. 18 with the pin locator positioned adjacent to the dental model.
Figures 20, 21:
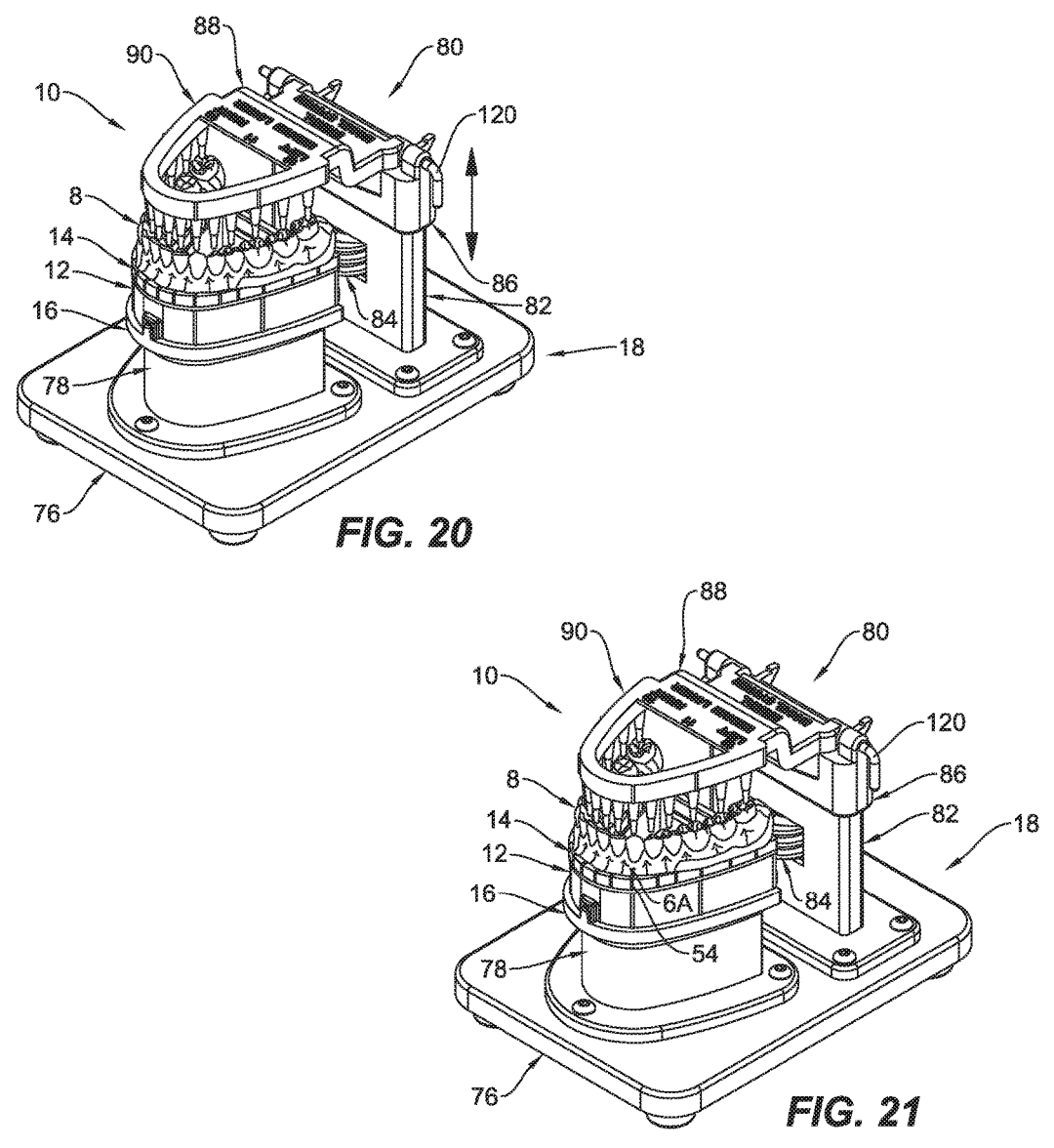

Referring to FIG. 19, the support arm 88 is rotated back to the first or adjacent position vertically above the dental model 8. FIG. 20 shows the screw 84 operated to lower the slide 86 until the locator pins 124 are positioned adjacent to occlusal surfaces of the teeth of the dental model 8. In at least one example, the locator pins 124 are positioned within about 0.5 millimeters to about 5 millimeters, and more preferably about 1 millimeter to about 2 millimeters of the teeth's occlusal surface. The dental model 8 is adjusted on the mounting plate 14 to align the locator pins 124 with individual teeth of the dental model 8.

Figure 22:
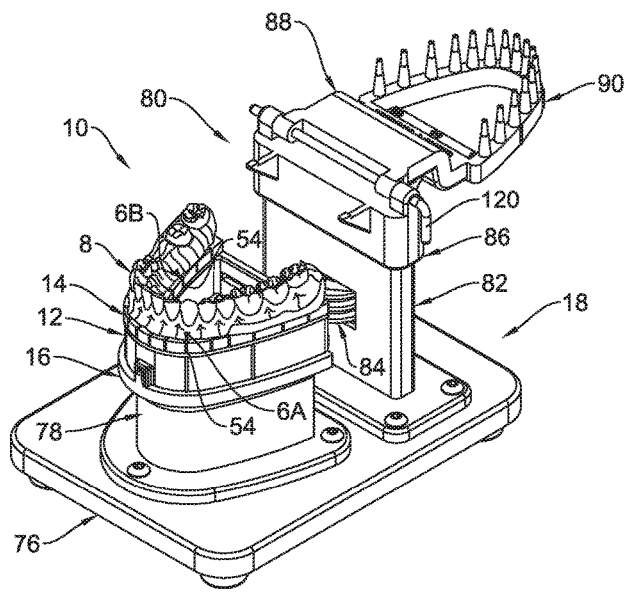
FIG. 22 is a perspective view of the alignment jig of FIG. 21 with the pin locator moved away from the dental model.

Once the alignment is completed precisely as possible, the operator may mark an outer surface of the dental model 8 with model markings 6A, 6B as shown in FIGS. 21 and 22, wherein the model markings 6A, 6B are aligned with some of the pin markings 54 or the markers 31, 33. The markings may be made using, for example, a permanent marker, paint, or stickers. The model markings 6A, 6B may provide a quick reference for realigning the dental model 8 relative to the mounting plate 14 after applying a bonding agent (e.g., adhesive) as will be described below.

Figure 23:
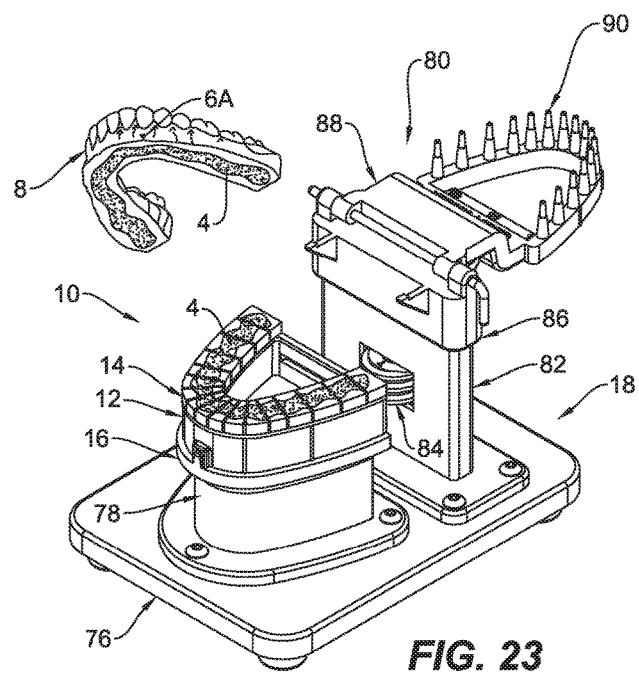
FIG. 23 is a perspective view of the alignment jig of FIG. 22 with an adhesive added between the mounting plate and dental model.

Referring to FIG. 22, the support arm 88 is rotated back to the second or removed position so that the operator can easily access the dental model 8 for removal of the dental model 8. FIG. 23 shows an adhesive 4 applied to a bottom surface of the dental model 8 and to the top surface of the mounting plate 14. The adhesive 4 may be applied along an entirety of the bottom surface of the dental model 8 and along an entirety of the top surface of the mounting plate 14, or along only portions thereof.

The dental model 8 is then returned to a position on top of the mounting plate 14 and the model markings 6A, 6B are aligned with associated markings on a mounting plate 14 (e.g., certain of the pin markings 54, markers 31, 33 or markings made by the operator). The operator rotates the support arm 88 back into the first or adjacent position, which should position the locator pins 124 adjacent to individual teeth of the dental model 8 as described above with reference to FIG. 21. The operator may make any fine tuning adjustments to align the locator pins 124 centrally on each tooth of the dental model 8. Typically, due to the fast setting properties of the adhesive 4, the operator has only a few seconds (e.g., less than 60 seconds) to make any adjustments of the dental model 8 relative to the mounting plate 14.

Figure 24:
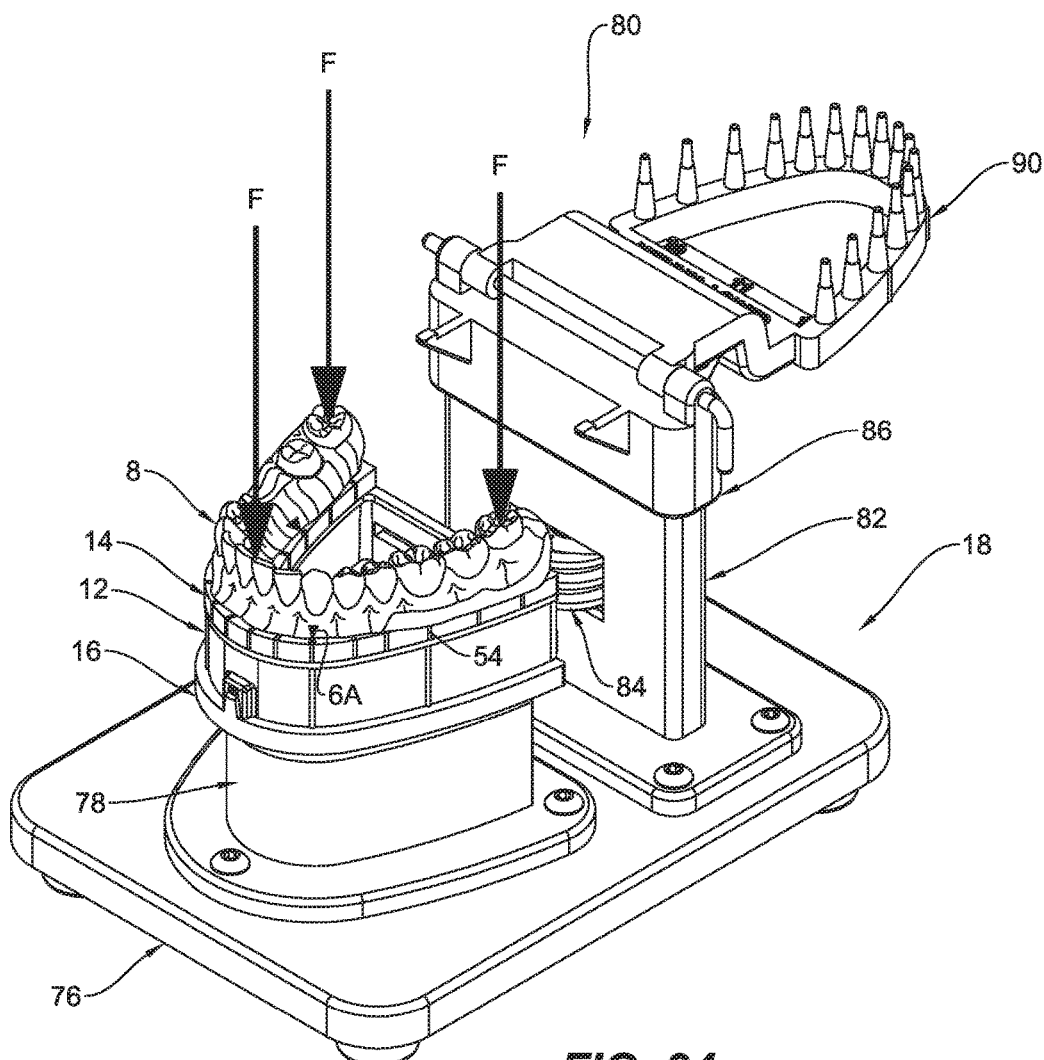
FIG. 24 is a perspective view showing the dental model secured to the mounting plate with the adhesive.
Figure 24A:
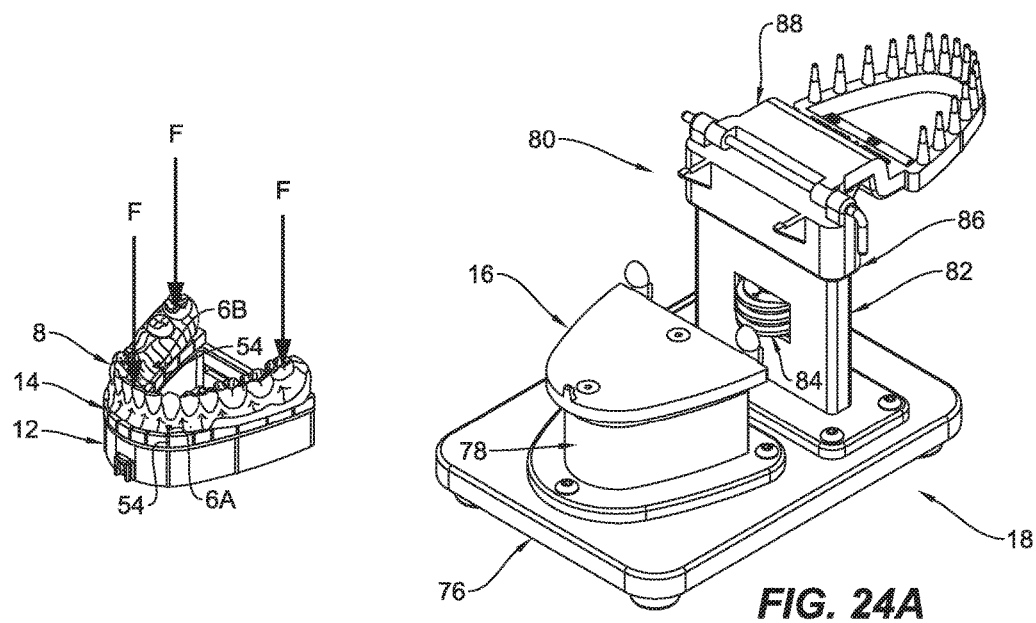
FIG. 24A is a perspective view showing the dental model secured to the mounting plate with the adhesive and removed from the alignment jig.

The operator may then move the support arm 88 into the second or removed position and apply a downward force on the dental model 8 to fix a position of the dental model 8 relative to the mounting plate 14. The application of pressure may secure the fixed interface and may accelerate setting of the adhesive 4. The operator may wipe away excess adhesive 4 that oozes out between the interface of the mounting plate 14 and dental model 8. The operator may apply the downward force F to the dental model 8 while the dental model base 12 remains mounted to the alignment jig 18 as shown in FIG. 24. Alternatively, as shown in FIG. 24A, the operator may remove the dental model base 12 from the alignment jig 18 and apply the downward force F at a location separate from the alignment jig 18.

Figure 25:
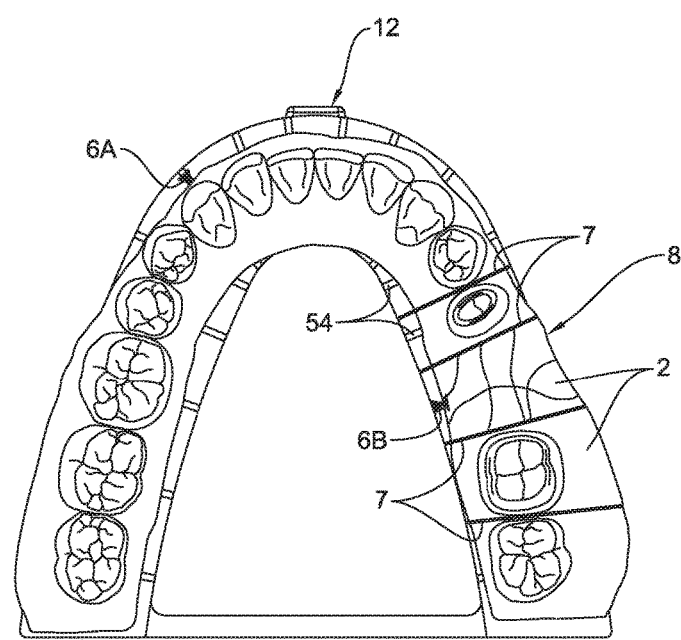
FIG. 25 shows the assembly of the dental model, dental model base and mounting plate of FIG. 24 with cuts to separate individual teeth of the dental model.
Figure 26:
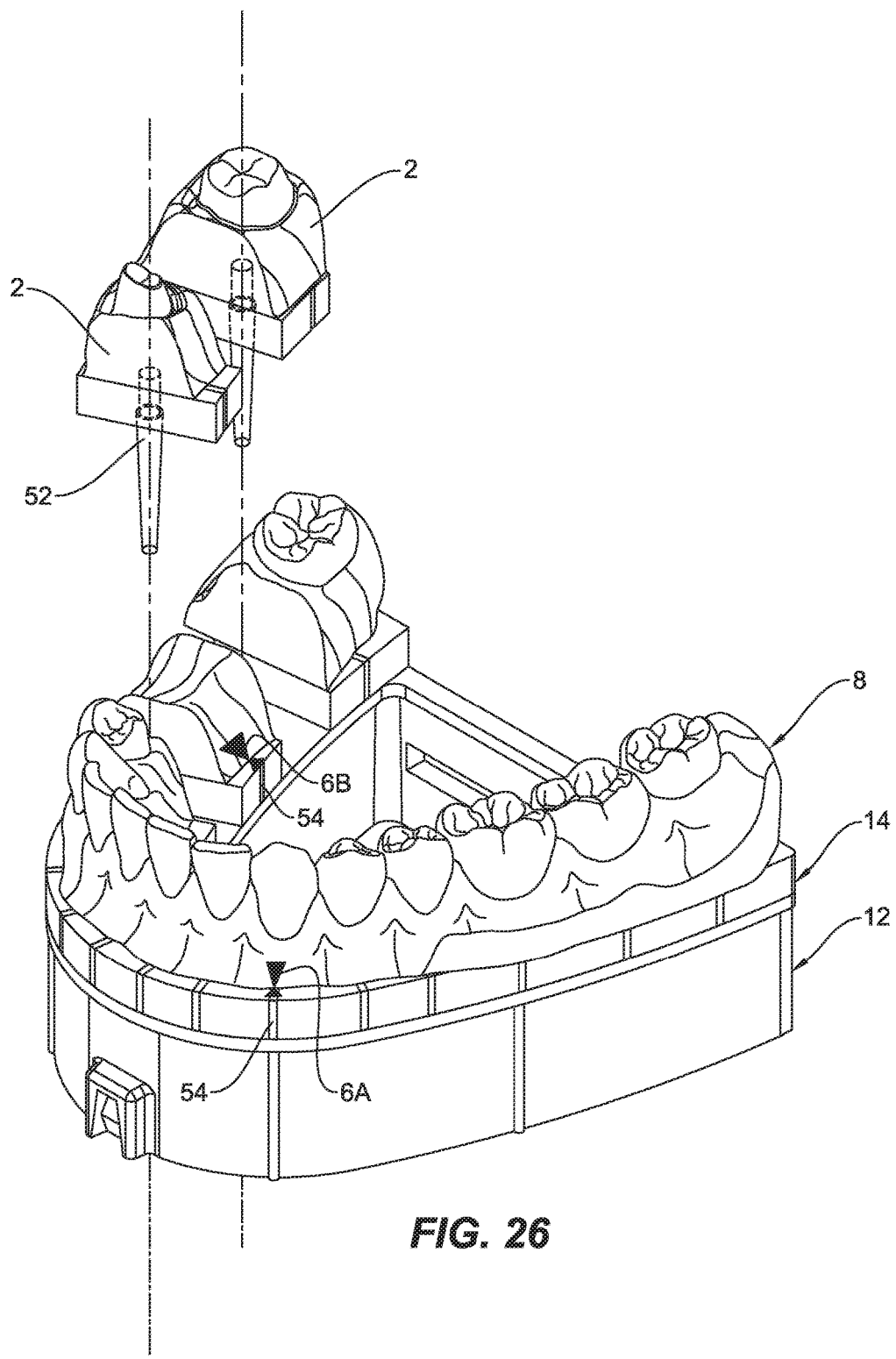
FIG. 26 is a perspective view of the assembly of FIG. 25 with some of the individual teeth models removed.

Referring to FIG. 25, the operator may then cut the dental model 8 between individual teeth of the dental model with cuts 7. The cuts 7 may extend through the mounting plate 14. The operator may wish to form the cuts 7 at a location between the pin markings 54 to ensure that the cut 7 does overlap one of the mounting pins 52.

After making the cuts 7, the operator may remove the individual teeth models 2 from the dental model base 12. The individual teeth models 2 may include a portion of the dental model 8, a portion of the mounting plate 14, and a separate mounting pin 52. The tapered construction of the mounting pins 52 may provide improved ease in removing and reinserting the mounting pins 52 relative to the dental model base 12.

Referring now to FIGS. 27-31F, another example dental modeling assembly 200 is shown with an alternative dental model base 212 and mounting plate 214. The dental model base 212 is configured as a quadrant shaped triple tray articulator component. The dental model base 212 has a generally linear construction rather than the arch shape construction of the dental model base 12 described above. The dental model base 212 includes a pair of alignment recesses 249 at opposing ends thereof, which are used to mount the dental model base 212 to an attachment plate 216. The dental model base 212 also includes an attachment arm 247. The attachment arm 247 may be configured to pivotally connect to another triple tray articulator component. The articulator features of the dental model base 212 are shown and described with reference to U.S. Pat. No. 7,690,919, which is incorporated herein by reference in its entirety.

Referring to FIGS. 31A-31F, the attachment plate 216 comprises a top surface 264, a bottom surface 266, upper and lower peripheral lips 271, 273, and a plurality of alignment posts 275. The alignment posts 275 interface with the alignment recesses 249 of the dental model base 212 to retain the dental model base 212 on the top surface 264 of the attachment plate 216. The alignment posts 275 may be positioned on and extending from both the top surface 264 and bottom surface 266. The position of the alignment posts 275 may accommodate different sizes of the dental model base 212. For example, the arrangement of alignment posts 275 on the top surface 264 may be configured to accommodate a medium-sized upper dental model base 212. The arrangement of alignment posts 275 with the bottom surface 266 may be configured to accommodate a medium-sized lower dental model base 212.

The upper and lower peripheral lips 271, 273 may help retain the dental model base 212 on a respective top or bottom surface 264, 266.

Figure 27:
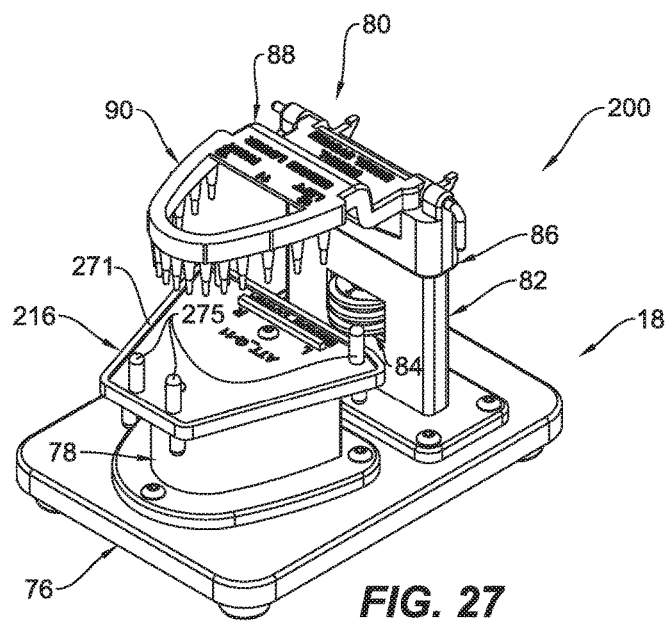
FIG. 27 is a perspective view of another example dental modeling assembly having an alternative attachment plate.
Figure 28:
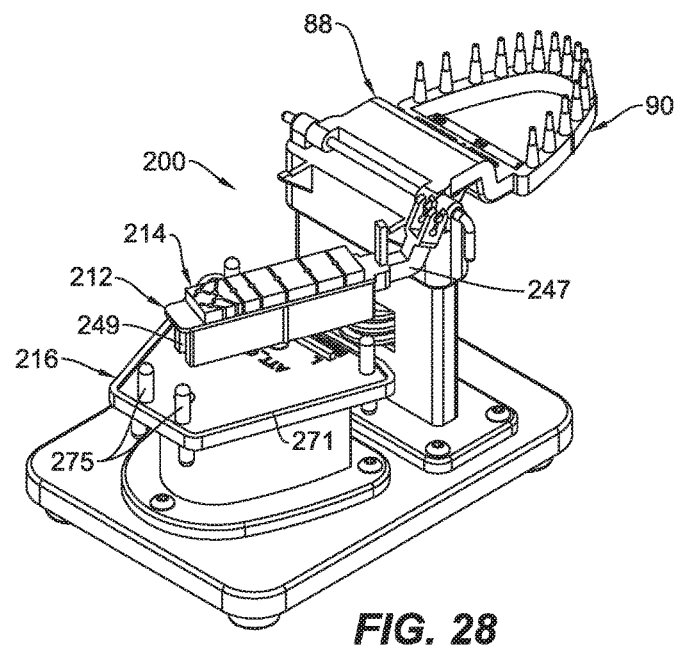
FIG. 28 is a perspective view of the dental modeling assembly of FIG. 27 with a triple tray quadrant articulator arranged for mounting to the attachment plate.
Figure 29:
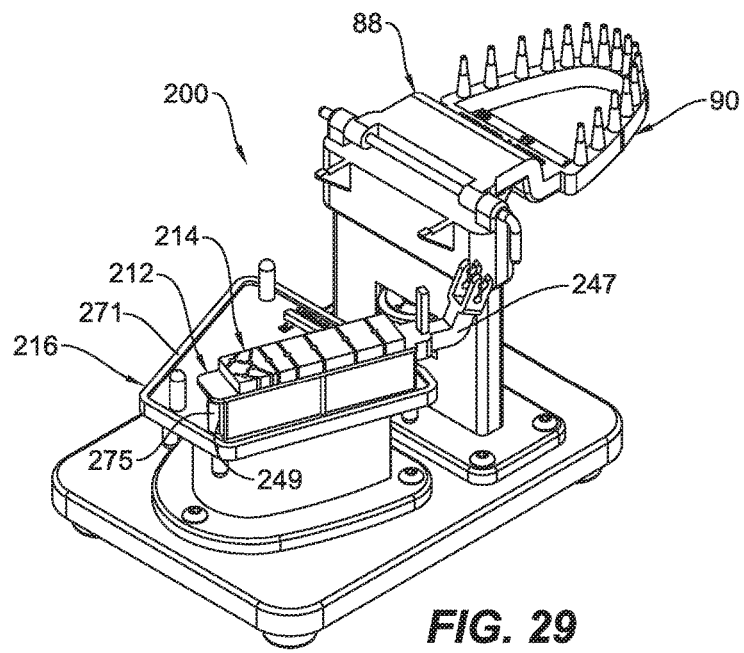
FIG. 29 is a perspective view showing the triple tray articulator mounted to the attachment plate.

Referring to FIGS. 27-30, an example method of using the dental modeling assembly 200 to mount a dental model to a dental model base is shown in various stages. FIG. 27 shows the alignment jig 18 assembled with the attachment plate 216 mounted to the pedestal 78. Referring to FIG. 28, the support arm 88 is rotated into the remove position and the dental model base 212 with mounting plate 214 is aligned with the alignment posts 275. FIG. 29 shows the dental model base 212 mounted to the attachment plate 216 with the alignment posts 275 contacting the alignment recesses 249 of the dental model base 212. As described above with reference to FIGS. 12-26, other steps may occur as part of connecting a dental model to the dental model base 212 and mounting plate 214 such as, for example, positioning a pin locator 90 adjacent to the mounting plate 214 to confirm a proper size of the pin locator 90.

Figure 30:
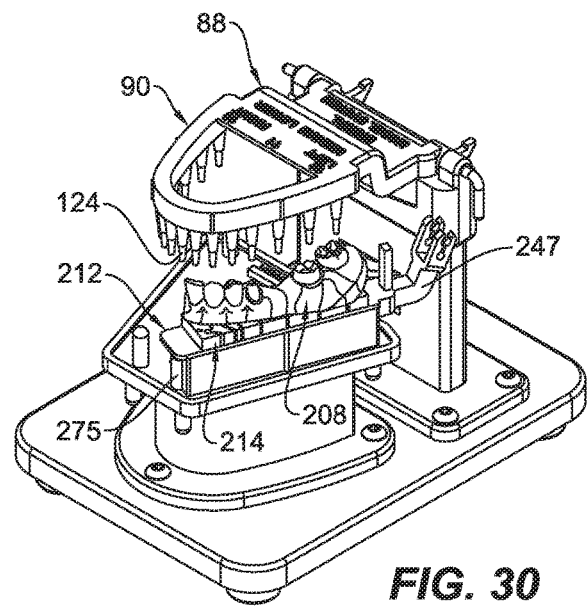
FIG. 30 is a perspective view of the dental modeling assembly of FIG. 29 with a portion of a dental model positioned on the quadrant triple tray articulator and the pin locator aligned with the model.
Figure 31A:
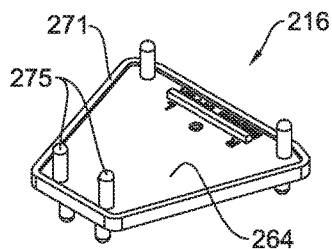
FIGS. 31A-31F show various views of the attachment plate shown in FIGS. 27-30.
Figure 31C:
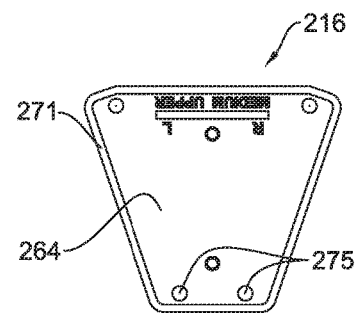
Figure 31B:
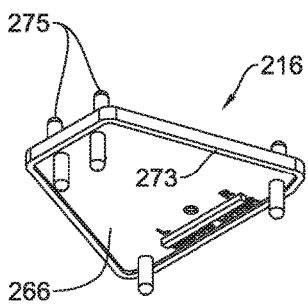
Figure 31D:
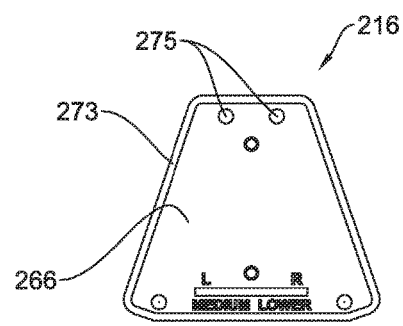
Figure 31F:
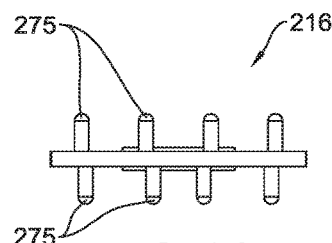
Figure 31E:
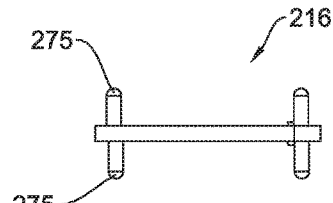

FIG. 30 shows a dental model 208 positioned on the mounting plate 214. The dental model 208 may include only a portion of an arc of a person's upper or lower teeth. The operator may align teeth of the dental model 208 with pin markings on the mounting plate 214. The support arm 88 may be rotated into the first or adjacent position to position the locator pins 124 adjacent to teeth of the dental model 208. The slide 86 is moved downward by operating screw 84 to position the locator pins 124 in close proximity to the teeth of dental model 208. The operator aligns the locator pins 124 centrally in alignment with each individual tooth of the dental model 208. The operator then may make markings such as model markings 6A, 6B discussed above with reference to FIGS. 12-26 to provide a rough indicator of the relative position between the dental model 208 and the mounting plate 214 for realigning the dental model 208 after applying a bonding agent such as adhesive 4 between the mounting plate 214 and the dental model 208. After applying the adhesive and repositioning the dental model 208 on the mounting plate 214, the operator may again confirm alignment of the dental model 208 using the pin locator 90, followed by applying a pressure force in a downward direction on the dental model 208 to fix the dental model 208 to the mounting plate 214.

The alignment jig 18 may be sized to accommodate positioning of the dental model base 212 with attachment arm 247 while still being able to operate the slide 86 up and down and rotating the support arm 88 between the first and second positions. A relative position between the support stand 80 and the pedestal 78 may be adjusted to accommodate dental model bases having various constructions and features such as different shaped attachment arms 247. The support arm 88 may be adjusted in length to accommodate any changes in relative position between the support stand 80 and pedestal 78.

Referring now to FIGS. 32-34F, another example dental modeling assembly 300 is shown including a dental model base 312, a mounting plate 314, an attachment plate 316, and the alignment jig 18. FIGS. 34A-34F show the attachment plate 316 having a top surface 364, a bottom surface 366, and upper and lower peripheral lips 371, 373. The upper and lower peripheral lips 371, 373 may be sized to accommodate different sizes for the dental model base 312. For example, the upper peripheral lip 371 may be sized to accommodate a medium-sized upper dental model base, and the lower peripheral lip 373 may be sized to accommodate a medium-sized lower dental model base.

Figure 32:
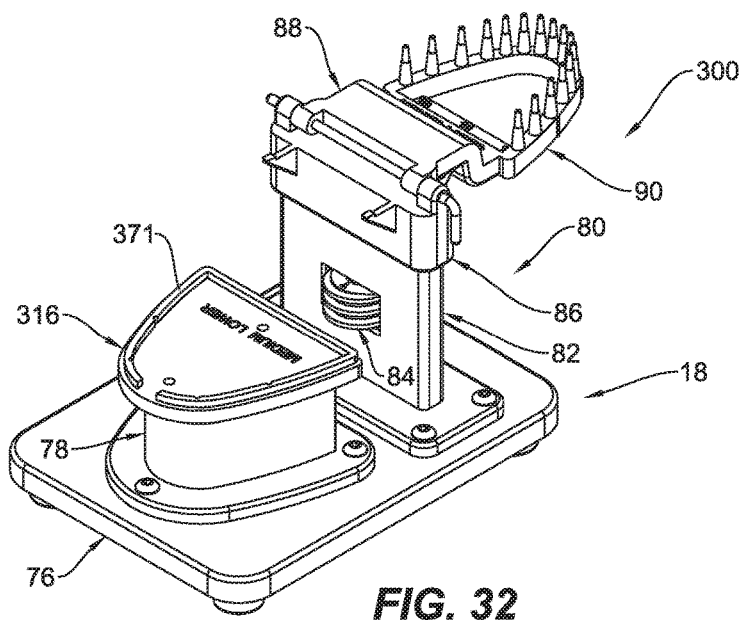
FIG. 32 is a perspective view of another example dental modeling assembly having an alternative attachment plate.
Figure 33:
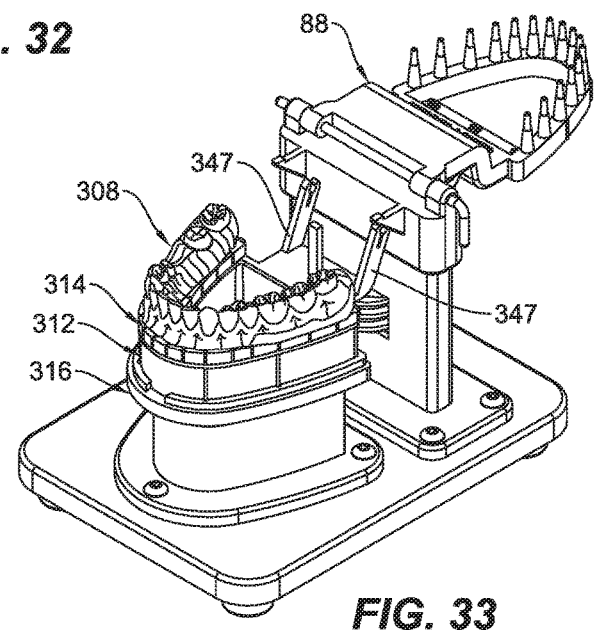
FIG. 33 shows the dental modeling assembly of FIG. 32 with an arc triple tray articulator mounted to the attachment plate and a dental model positioned on the articulator.
Figure 34A:
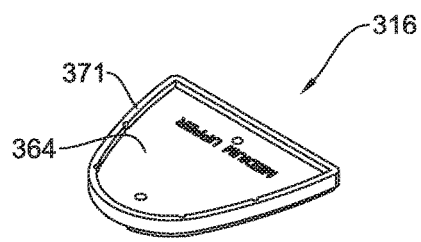
FIGS. 34A-34F show various views of the attachment plate shown in FIGS. 32-33.
Figure 34C:
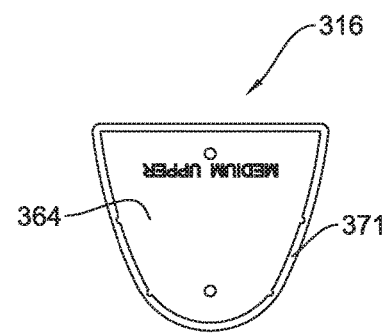
Figure 34B:
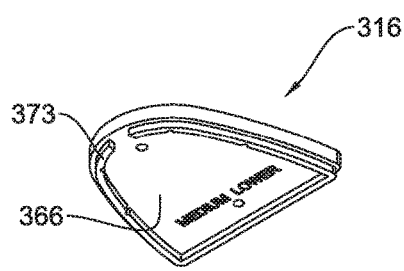
Figure 34D:
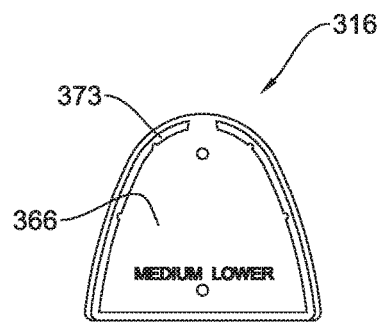
Figure 34F:
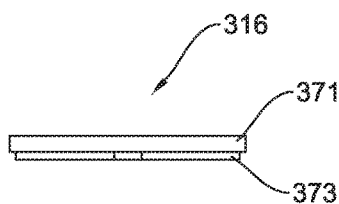
Figure 34E:
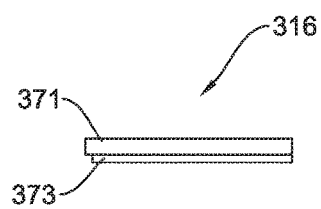
Figure 35:
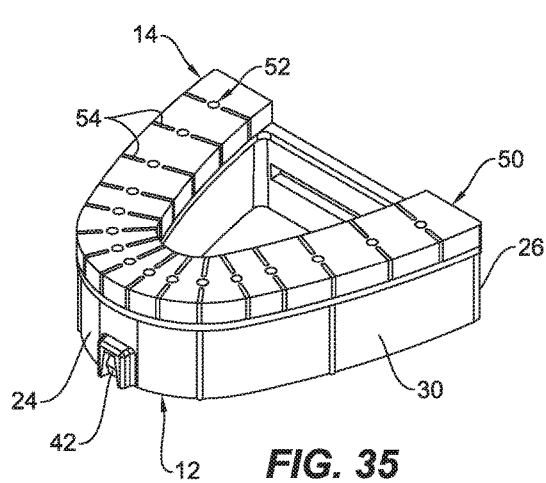
FIGS. 35-36 show perspective views of the dental model base and mounting plate of FIG. 1 assembled together.

FIG. 32 shows the attachment plate 316 mounted to the pedestal 78 of the alignment jig 18. The support arm 88 is rotated into the remove position to move the pin locator 90 out of the way from obstructing the attachment plate 316. The slide 86 may be moved vertically upward using screw 84. FIG. 33 shows the dental model base 312 with mounting plate 314 mounted to the attachment plate 316. Additional methods steps may include positioning the pin locator 90 adjacent to or even in contact with the top surface of the mounting plate 314 to confirm a proper size has been selected for the pin locator 90.

FIG. 33 shows a dental model 308 positioned on the mounting plate 314. An initial adjustment may be made by the operator to align teeth of the dental model 308 with pin markings on the mounting plate 314. The operator may then rotate the support arm 88 into the first position to position the locator pins 124 adjacent to teeth of the dental model 308. The slide 86 may be adjusted using screw 84 to position the locator pins 124 adjacent to an occlusional surface of the dental model 308. The operator may adjust a position of the dental model 308 relative to the locator pins 124 and the mounting plate 314 to align a separate locator pin 124 centrally and vertically above each tooth of the dental model 308. The operator may then rotate the support arm 88 into the removed position, and apply a marking to the dental model 308 to provide a rough indicator (e.g., in alignment with one of the pin markings on a mounting plate 314) for a quick repositioning of the dental model 308 after applying a bonding agent (e.g., adhesive 4). After applying the adhesive 4 to the dental model 308 and mounting plate 314, the operator repositions the dental model 308 on a mounting plate 314 and aligns the manually applied markings (e.g., model markings 6A, 6B) with the pin markings. The operator then rotates the support arm 88 back into the first position to align the locator pins 124 with individual teeth of the dental model 308. Once alignment is confirmed, the operator moves the pin locator 90 back to the second position and applies a pressure force in a downward direction to fix the dental model 308 to the mounting plate 314.

FIGS. 35-40D show the dental model base 12 and mounting plate 14 described above with references to FIGS. 1-26. The mounting plate 14 includes a separate mounting pin 52 associated with each pin aperture 34 and pin support protrusion 36 of the dental model base 12. In at least some arrangements, the plate portion 50 of the dental model base 12 comprises a polymer material such as polyurethane. The materials for the mounting pins 52 may have a different material composition including, for example, a metal material. The materials of the dental model base 12 may have a different material composition from materials of the mounting plate 14. In at least one example, a difference in materials between the dental model base 12 and plate portion 50 is sufficient to provide molding of the plate portion 50 directly onto the dental model base 12 and release of the plate portion 50 from the dental model base 12 after the materials of the plate portion 50 are cured. Using this type of molding, the indexing apertures 55 (see FIG. 38) may be formed to exactly match the layout and size of the indexing members 38, 40.

FIGS. 41A-45 show an example method of forming the mounting plate 14. FIG. 41A shows a plurality of mounting pins 52 positioned in the pin apertures 34 of the dental model base 12. FIG. 41B shows the mounting pins 52 aligned with the pin apertures 34 before insertion. The dental model base 12 with the mounting pins 52 is then positioned in a plate mold member 130. The model support surface 28 of the dental model base 12 is positioned spaced apart from a top surface 138 of the plate mold member 130. The plate mold member 130 also includes a bottom opening 132, through which the dental model base 12 is inserted, a top opening 134, and a base cavity 136. In at least some arrangements, a model engagement portion 62 of the mounting pins 52 (also referred to as a knurled end or an end having a knurled surface), is positioned within the base cavity 136 and may extend vertically above the top surface 138. The base cavity 136 may be filled with a material used to form the plate portion 50 directly on the model support surface 28 of the dental model base 12 (see FIG. 42) while the dental model base 12 is positioned within the base cavity 136 (see also FIG. 43). After the plate portion 50 is cured, the mold member 130 is removed and the plate portion 50 is permanently connected to each of the mounting pins 52 (e.g., the model engagement portion 62 of the each of the mounting pins 52) (see FIGS. 44 and 45).

After forming the mounting plate 14 using the plate mold member 130, the top surface of the attachment plate 16 may be machined to a finished condition. In one example, the top surface 56 is machined to remove any imperfection or discontinuities along the top surface 56. The machining may include milling and may involve removing a portion of the model engagement portion 62 of the mounting pins 52. In at least one example, the model engagement portions 62 of the mounting pins 52 re machined flush with the top surface 56. This machining may provide a specific thickness for the plate portion 50. The thickness may be in the range of, for example, about 0.15 inch to about 0.3 inches, and more preferably about 0.18 inches to about 0.2 inches. The thickness of the plate portion 50 may be originally formed at about 0.2 inches to about 0.3 inches and the model engagement portion 62 may extend to a length of about 0.2 inches to about 0.3 inches from the top surface of the dental model base 12.

Referring now to FIGS. 46-51D, another example dental model base 412 and mounting plate 414 is shown and described. The dental model base 412 has a quadrant shape that tracks a portion of the full arc of the dental model base 12 described above. The mounting plate 414 may have a shape that tracks the partial or quadrant arc shape of the dental model base 412. The dental model base 412 may include latch and ball and socket connection features that may provide a quick release (e.g., snap-fit) connection of the dental model base 412 to the attachment plate 16 described above. The dental model base 412 and mounting plate 414 may have many similar features as the dental model base 12 and mounting plate 14 described above, but limited to a partial arc construction.

Figure 52A:
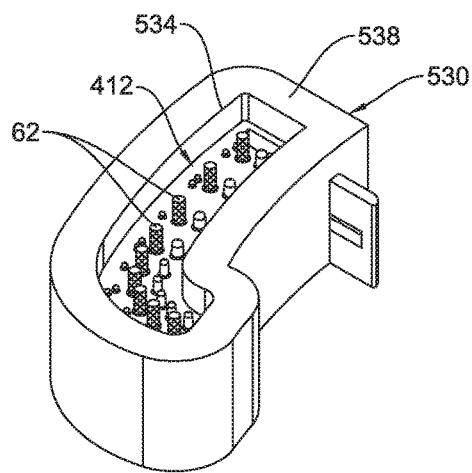
FIG. 52A is a perspective view of the dental base of FIG. 46 having a plurality of mounting pins inserted therein with the dental model base positioned in a mold.
Figure 52B:
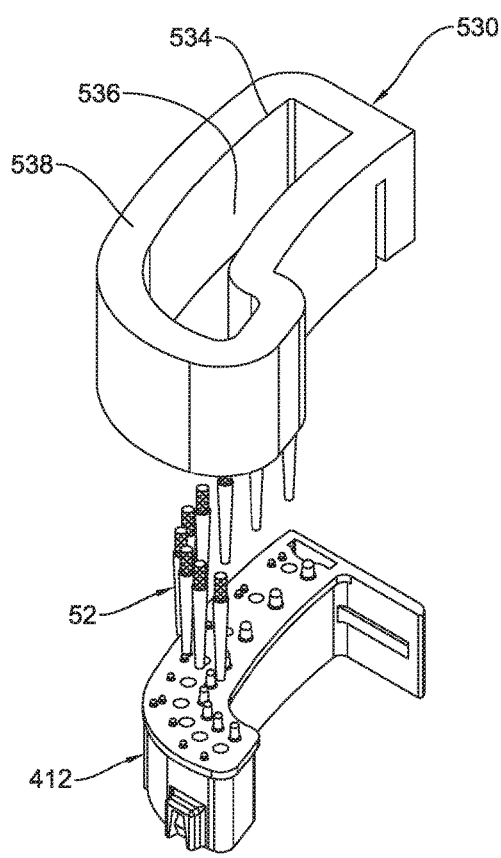
FIG. 52B is an exploded perspective view of the dental model base, mounting pins, and mold of FIG. 52A.

The mounting plate 414 may be formed in a similar manner to how the mounting plate is formed using the plate mold member 130 described above. FIG. 52A shows the dental model base 412 having a plurality of mounting pins 52 positioned therein and the dental model base 412 positioned in a plate mold member 530. FIG. 52B shows the mounting pins 52 aligned with the pin apertures of the dental model base 412 before insertion. The plate mold member 530 includes a bottom opening 532, a top opening 534, a base cavity 536, and a top surface 538. The dental model base 412 is inserted into the bottom opening 532 with a top mold support surface of the dental model base 412 spaced from the top surface 538. This portion of the base cavity 536 may be filled with material that forms the plate portion of the mounting plate 414. The model engagement portions of the mounting pins are exposed within this space so that the plate portion is permanently connected to the mounting pins as part of forming the plate portion.

Figure 53:
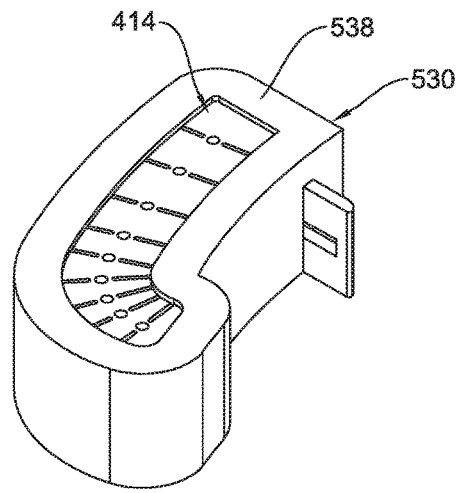
FIGS. 53-54 are perspective views of the assembly of FIG. 52A with the mold filled to form a plate portion of the mounting plate.
Figure 55:
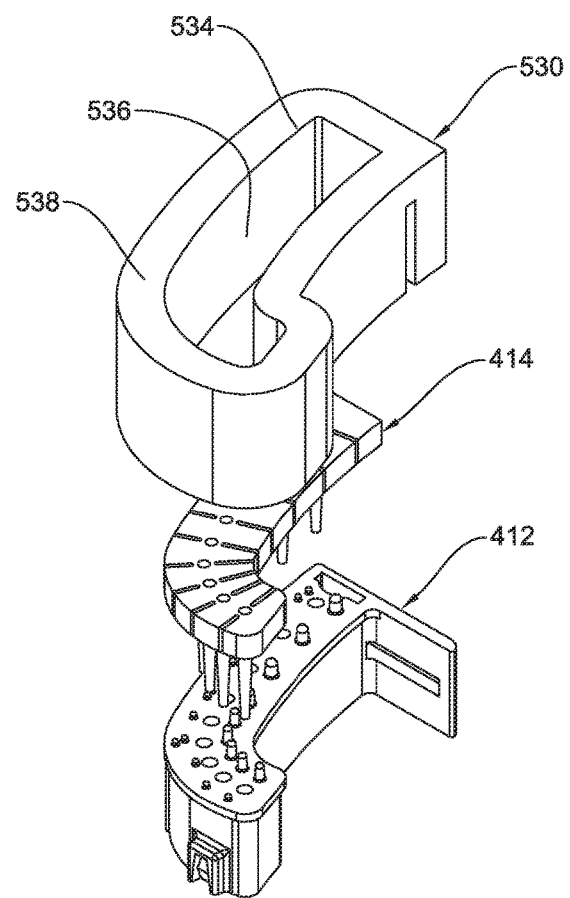
FIGS. 55-56 are exploded perspective views of the assembly of FIGS. 53-54.
Figure 54:
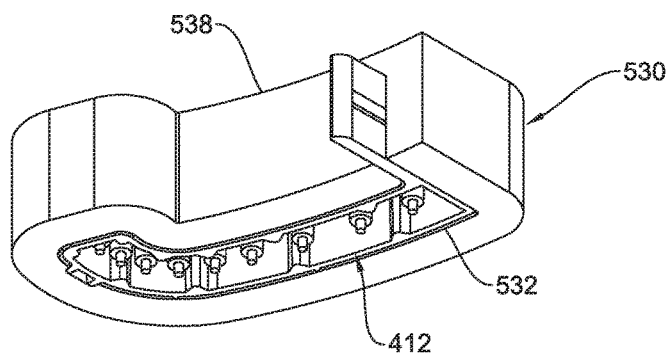
Figure 56:
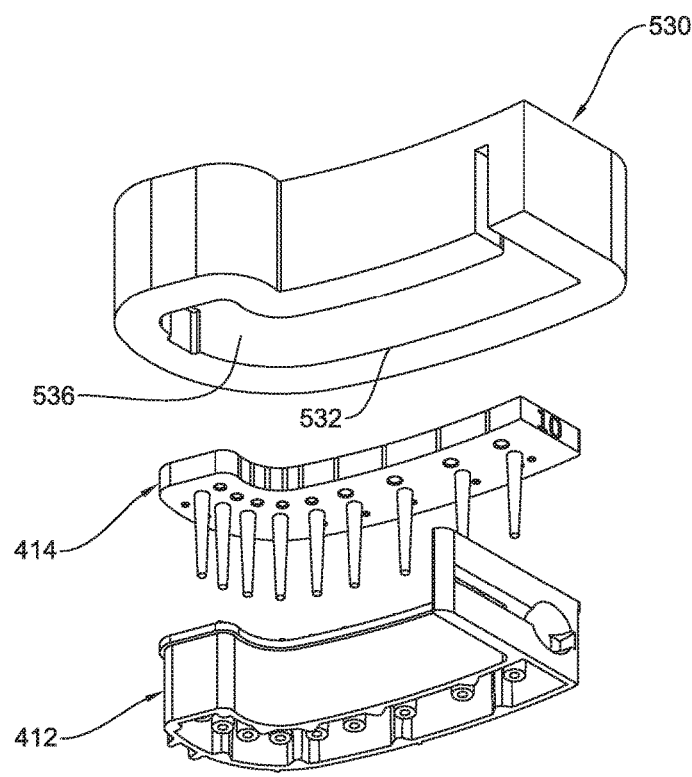
Figure 57:
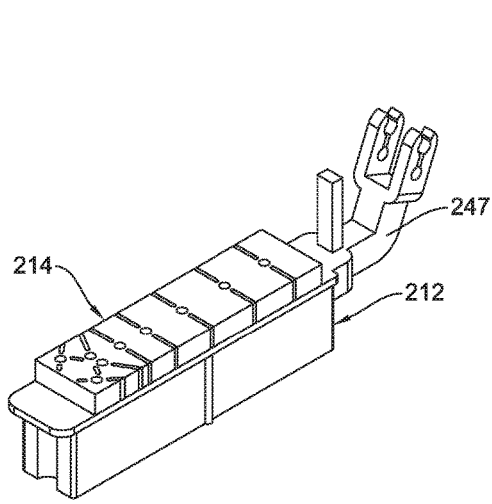
FIGS. 57-58 are perspective views of the quadrant triple tray articulator shown in FIGS. 28-30 assembled together.
Figure 59:
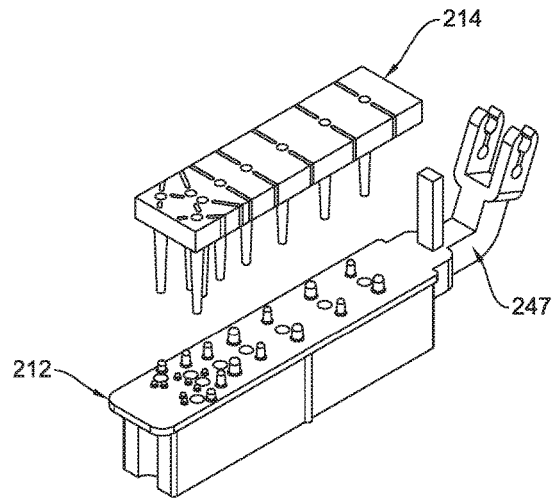
FIGS. 59-60 are exploded perspective views of the quadrant triple tray articulator of FIGS. 57-58.
Figure 58:
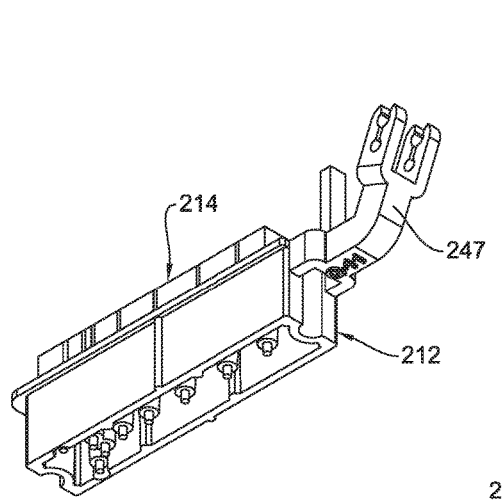
Figure 60:
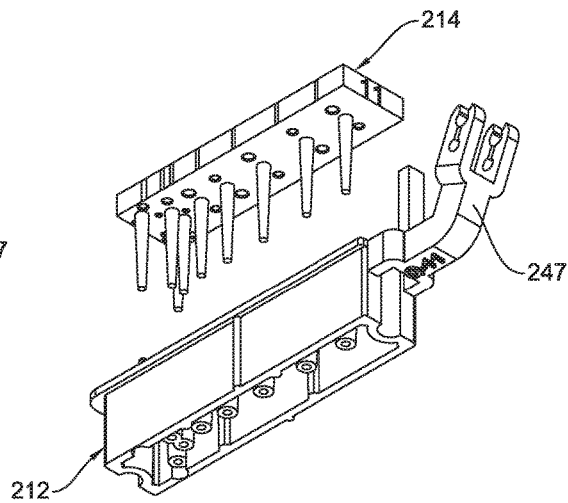
Figure 62A:
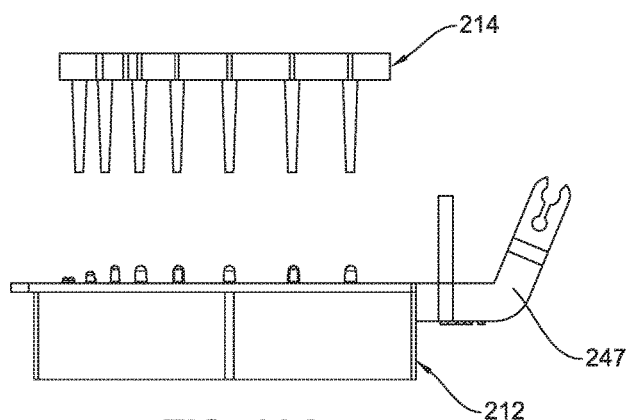
FIGS. 62A-62D are plan views of the quadrant triple tray articulator of FIGS. 59-60.
Figure 62C:
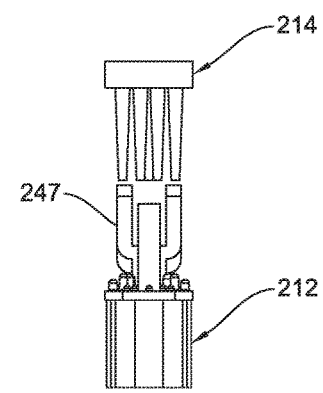
Figure 62B:
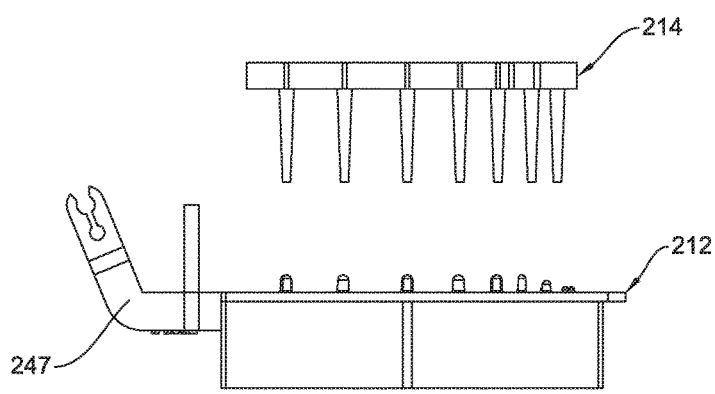
Figure 62D:
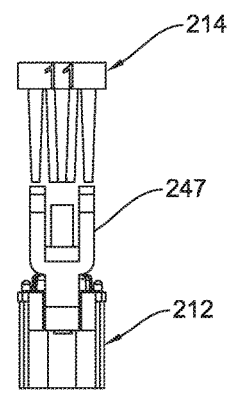

FIGS. 53 and 54 shows the plate portion 450 formed within the base cavity 536. FIGS. 55 and 56 show the dental model base 412 and mounting plate 414 removed from the plate mold member 530.

FIGS. 57-62D show the dental model base 212 and mounting plate 214 described above with reference to FIGS. 27-31F. The mounting plate 214 is shown including a plurality of mounting pins arranged to extend into corresponding pin apertures of the dental model base 212. The attachment arm 247 includes female connector recesses for attaching to another triple tray articulator component. Other triple tray articulator components may comprise a male connection feature insertable into the female recess feature of the attachment arm 247.

Figure 63A:
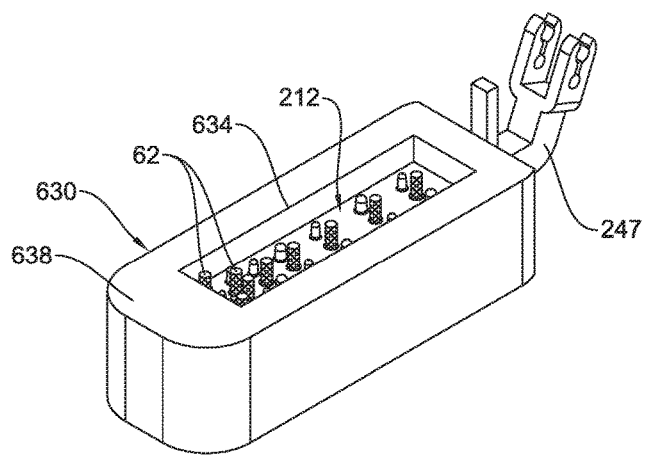
FIG. 63A is a perspective view of another example dental model base having a plurality of mounting pins positioned therein with the dental model base enclosed in a mold.
Figure 63B:
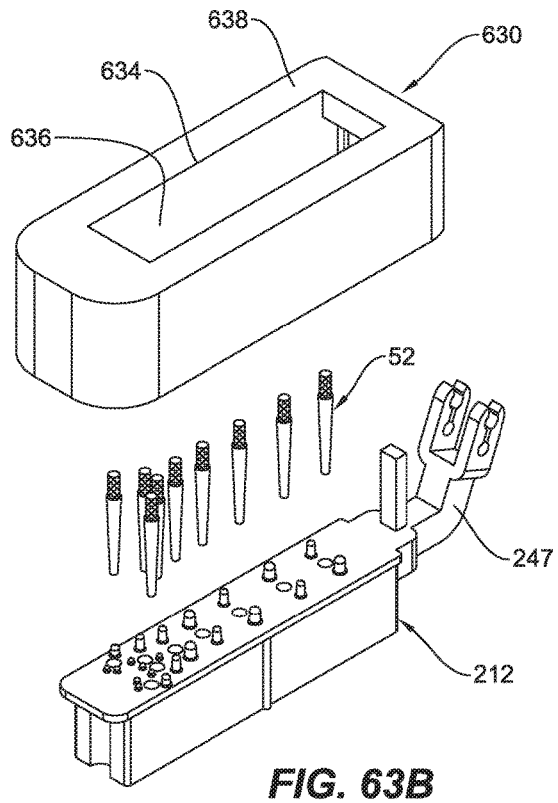
FIG. 63B is an exploded perspective view of the dental model base, mounting pins, and mold of FIG. 63A.

FIG. 63A shows a plate mold member 630 used to form a plate portion of the mounting plate 214. The mounting pins 52 of the mounting plate 214 are positioned in the dental model base 212, and the dental model base 212 is inserted through a bottom opening 632 into a base cavity 636 of the plate mold member 630. FIG. 63B shows the mounting pins 52 aligned with the pin apertures of the dental model base 212 prior to insertion. A top mold support surface of the dental model base 212 is spaced from a top surface 638 to provide a portion of the base cavity 636 accessible through a top opening 634 to insert material to form the plate portion.

Figure 64:
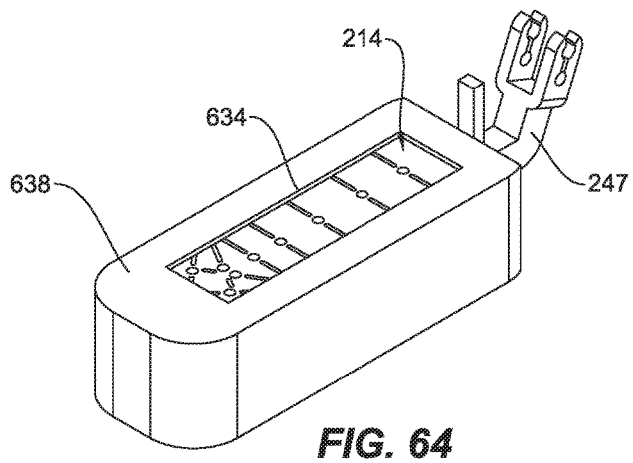
FIGS. 64-65 are perspective views of the assembly of FIG. 63A with the mold filled to form a plate portion of the mounting plate.
Figure 66:
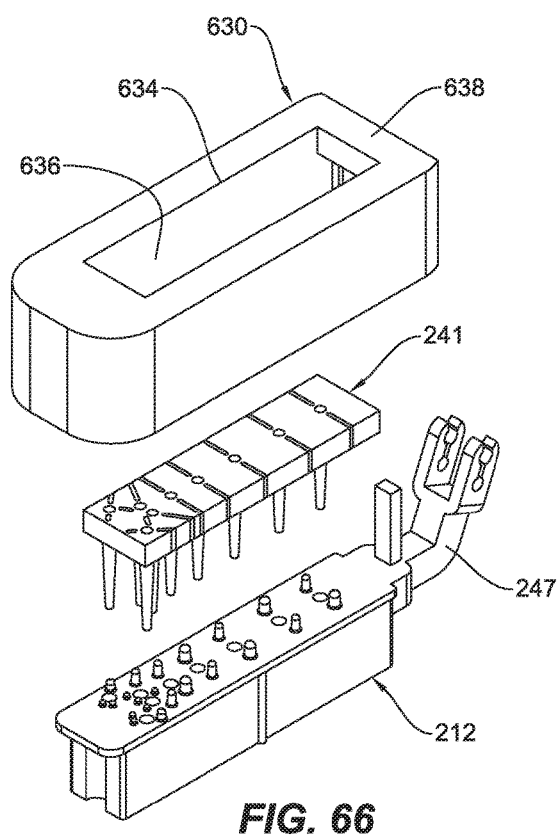
FIGS. 66-67 are exploded perspective views of the assembly of FIGS. 64-65.
Figure 65:
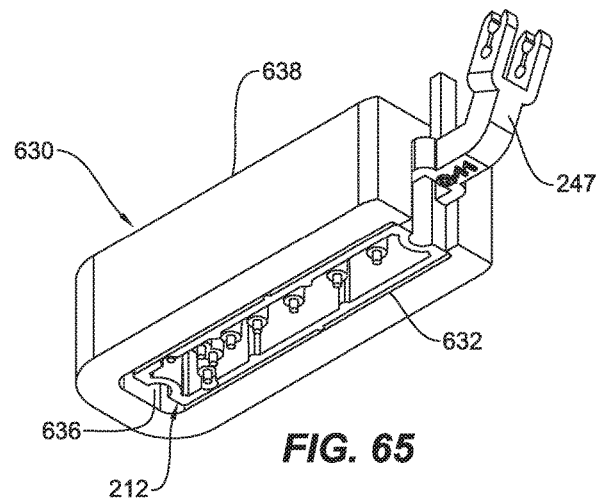
Figure 67:
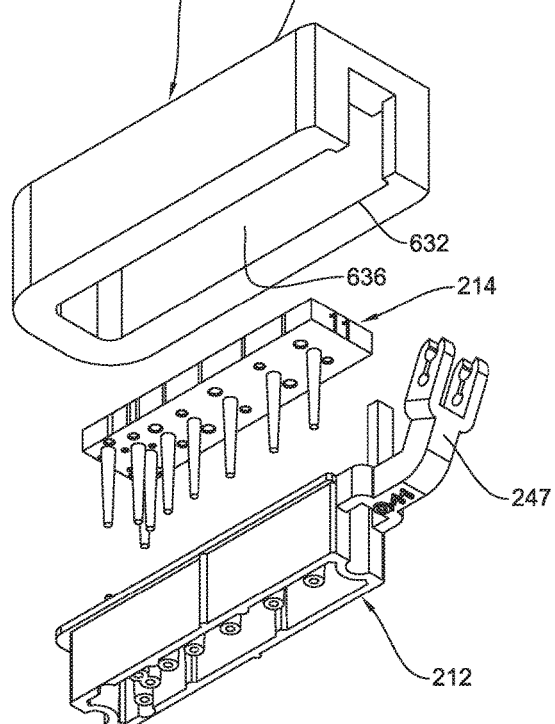

FIGS. 64 and 65 show the plate portion formed within the base cavity 636 and permanently connected to the model engagement portions of the mounting pins. FIGS. 66 and 67 show the dental model base 212 and mounting plate 214 separated from the plate mold member 630.

Figure 68:
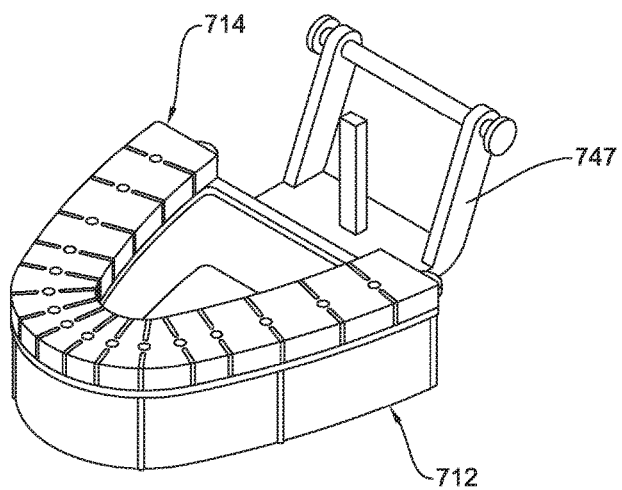
FIG. 68 is a perspective view of an arc triple tray articulator with mounting plate assembled thereto in accordance with the present disclosure.
Figure 69:
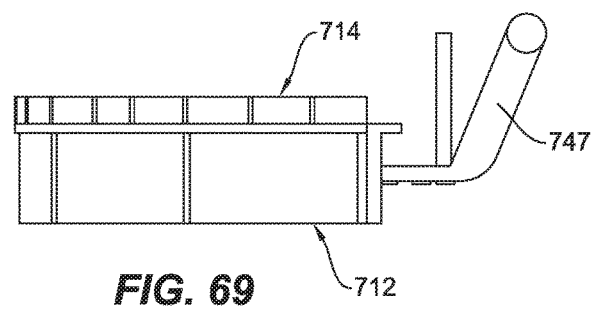
FIG. 69 is a side view of the arc triple tray articulator of FIG. 68.
Figure 70A:
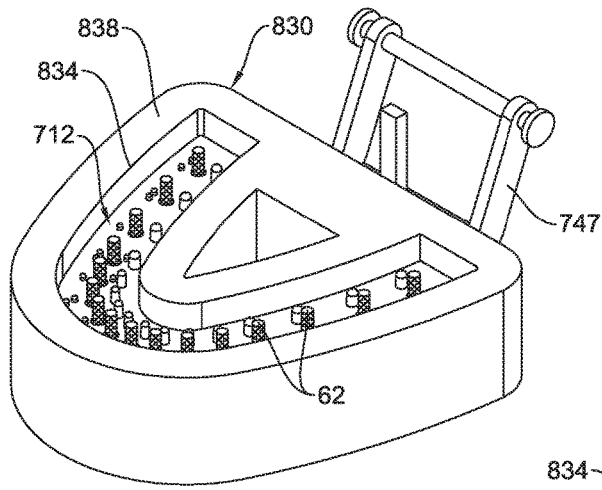
FIG. 70A is a perspective view of the arc triple tray articulator of FIG. 68 having a plurality of mounting pins positioned therein with the articulator enclosed in a mold.
Figure 70B:
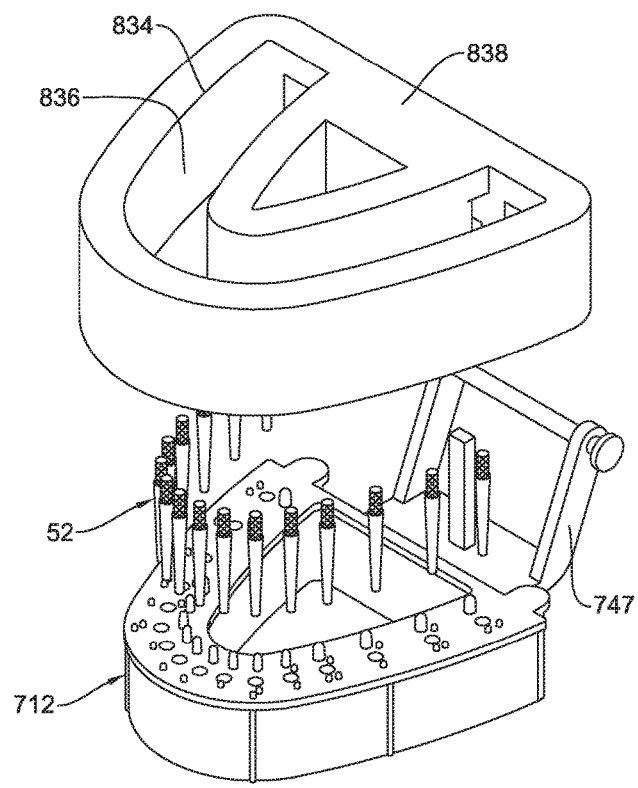
FIG. 70B is an exploded perspective view of the dental model base, mounting pins, and mold of FIG. 70A.
Figure 71:
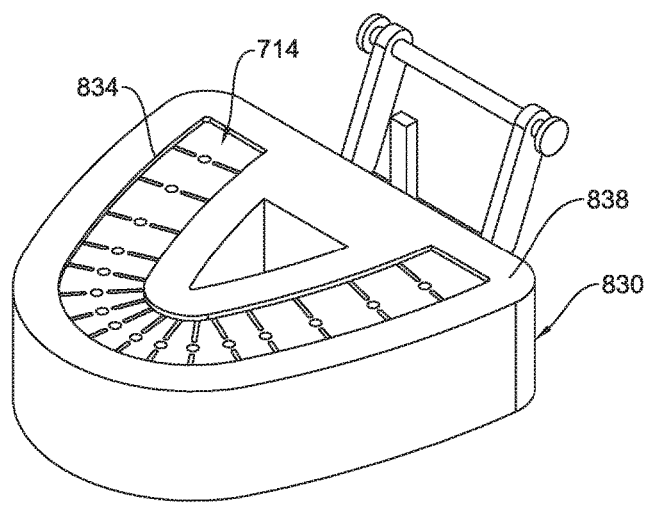
FIGS. 71-72 are perspective views of the assembly of FIG. 70A with the mold filled to form a plate portion of the mounting plate.
Figure 73:
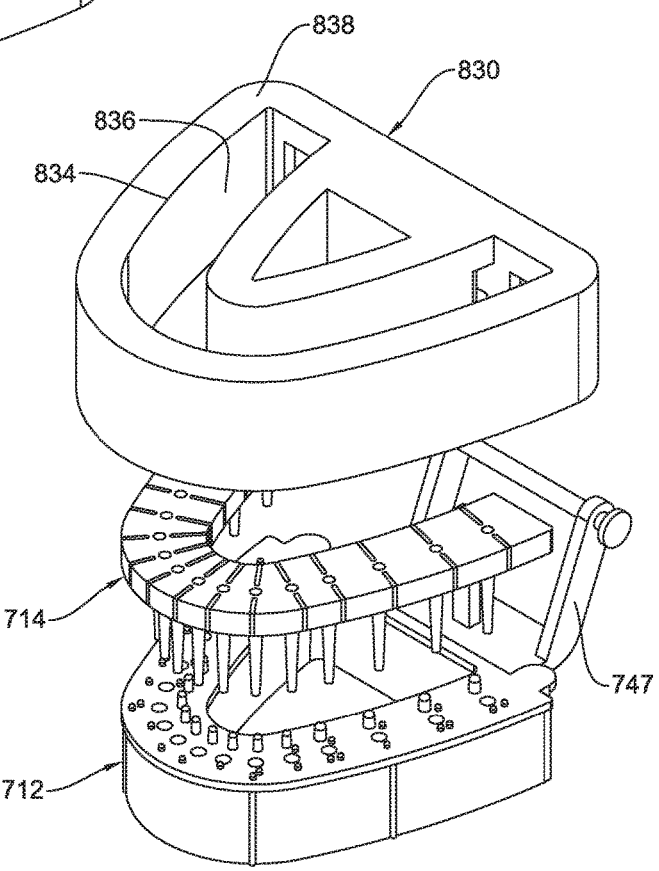
FIGS. 73-74 are exploded perspective views of the assembly of FIG. 71.
Figures 72, 74:
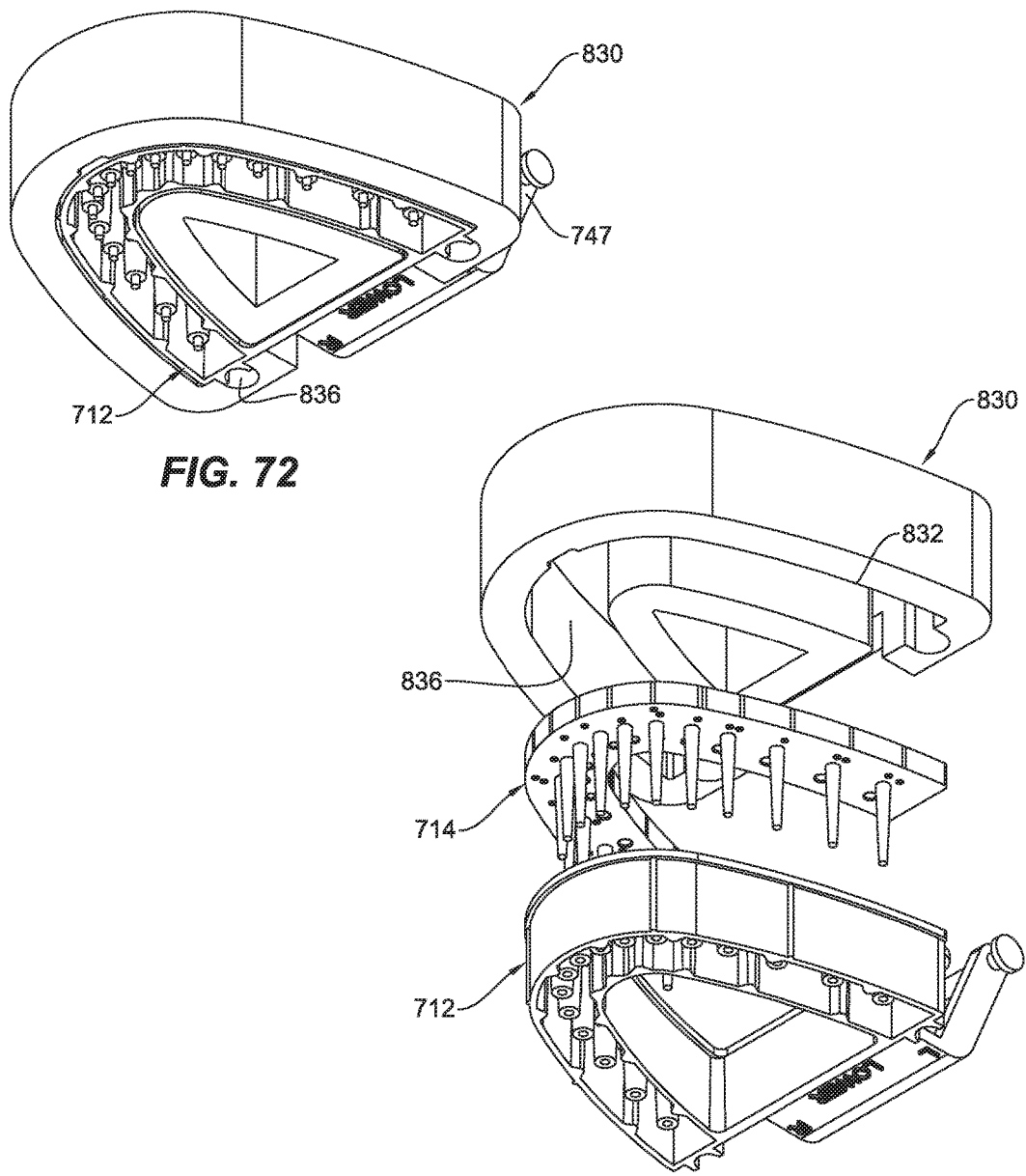

FIGS. 68-69 show another example dental model base 712 and mounting plate 714. The dental model base is in a form of a full arc triple tray articulator having an attachment arm 747. The attachment arm 747 may be configured for attachment to another triple tray articulator component having, for example, a male connection feature that is inserted into a female connection feature of the attachment arm 747. The mounting plate 714 may have the same or similar construction as the mounting plate 14 described above. The mounting plate 714 may be formed using a plate mold member as shown and described with reference to FIGS. 70-74. The plate mold member 830 may include a bottom opening 832, a top opening 834, a base cavity 836, and a top surface 838. The plate portion of the mounting plate 714 may be formed using similar methods steps as described above with reference to FIGS. 41-45.

The plate mold members shown and described with reference to the figures may have a resilient construction that permits easier insertion of and removal of the dental model base and mounting plate as part of forming the plate portion of the mounting plate. Other types of molds may be used, and may be better suited for mass production of the mounting plate. In one example, the mold comprises a dual cavity construction that surrounds portions of the dental model base from different directions and may assist in forming a plate portion having more precise dimensions and improved surface finish. In one example, the mold comprises at least two parts, which when assembled together around portions of the dental model base form a mold cavity that is filled by injection molding.

Referring now to the attached figures, several example embodiments are disclosed. The embodiments of FIGS. 75-92 and 116-138 relate to dental modeling assemblies having quadrant and full art instructions, respectively, wherein the dental model bases associated with the dental modeling assemblies are configured for attachment to a separate articulator device. An example separate articulator device is disclosed in U.S. Pat. No. 4,734,033 commonly marketed as the Vertex® articulator sold by DENTSPLY of Burlington, N.J. Another example separate articulator is disclosed in FIGS. 18-19 of U.S. Published Application No. 2006/0281,043, which articulator includes the capability of mounting a dental model base therein using an attachment plate having a ball and socket and latch connection arrangement. U.S. Pat. No. 4,734,033 and U.S. 2006/0281,043 are hereby incorporated in their entireties by this reference.

The embodiment of FIGS. 93-115 is directed to a dental modeling assembly having what is commonly referred to as a triple tray articulator. Triple tray articulators include hinge attachment features that are formed integral with the dental model base. The embodiment of FIGS. 93-115 includes a quadrant-style dental model base. Other dental model base constructions having integral articulator components in related methods of use are disclosed in U.S. Pat. No. 7,690,919, which is hereby incorporated in its entirety by this reference.

The example dental model bases disclosed herein may be configured for use with the impressionless dental modeling system methods disclosed herein, as well as being configured for use with systems and methods of former dental models using an impression of a person's teeth. While the dental model bases disclosed herein with reference to the attached figures emphasize the use of a plurality of removable dowel pins, other types of dental model bases may be used such as, for example, the opposing bases disclosed in U.S. Published Application No. 2006/0281043, which is incorporated by reference above. In one example, a dental model of a person's upper teeth may be formed on a dental model base with removable dowel pins using an impressionless modeling method, and a dental model of a person's lower teeth (i.e., the opposing teeth) may be formed on an opposing model base that is void of removable dowel pins using one of the impressionless modeling systems disclosed herein.

Figure 115:
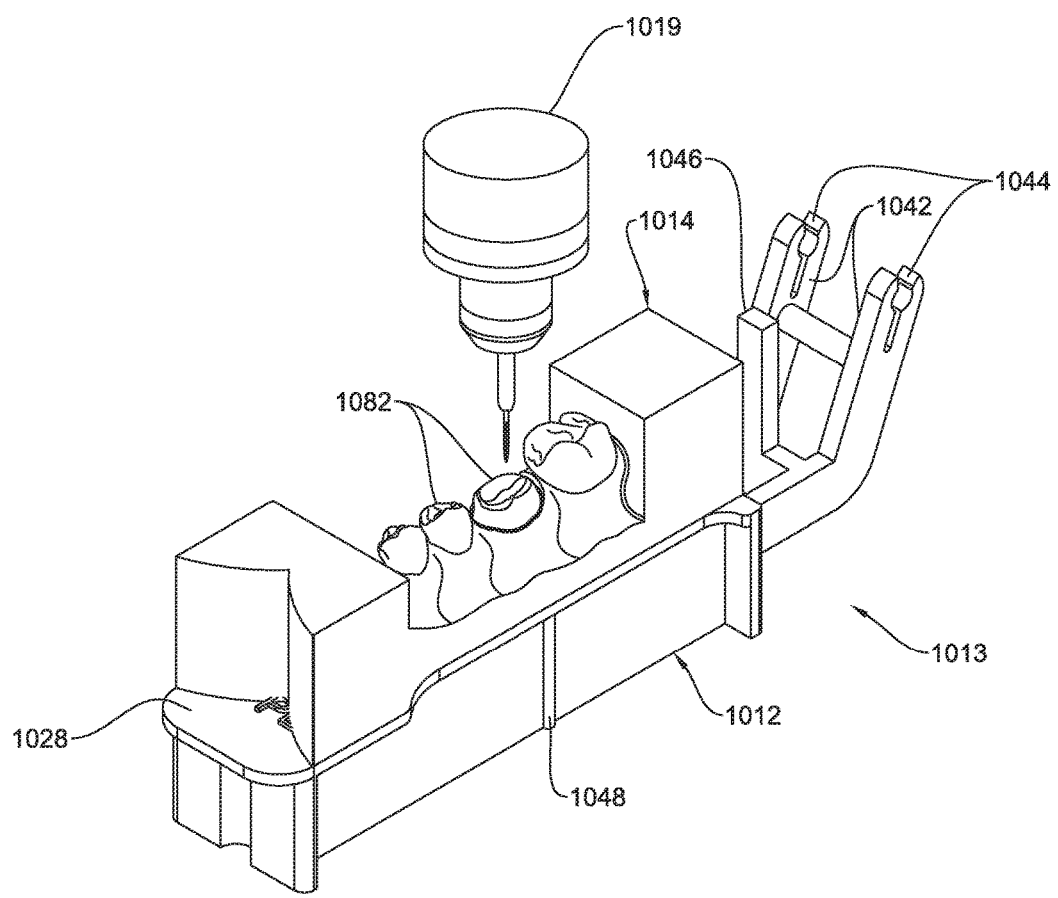
FIG. 115 is a front perspective view of the mounting molding block of FIG. 94 at least partially milled to form a dental model.
Figure 116:
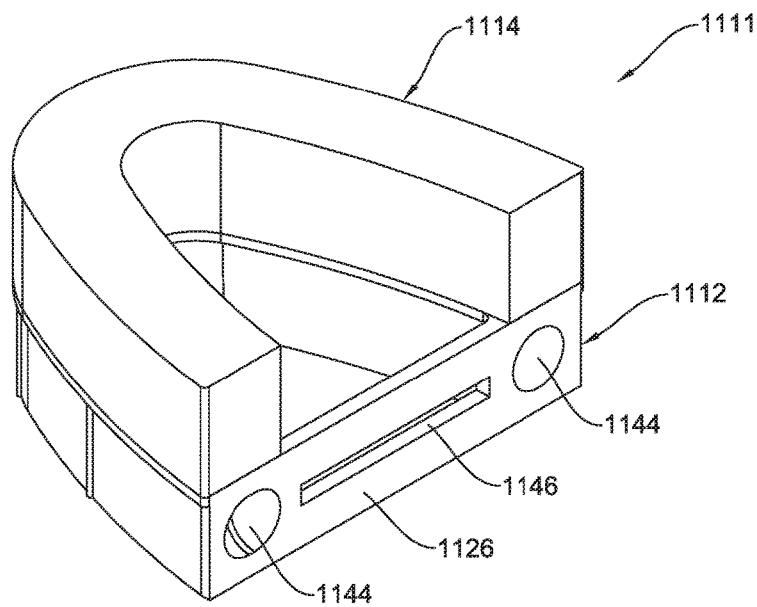
FIG. 116 is a rear perspective view of another example mounted molding block in accordance with the present disclosure.
Figure 117:
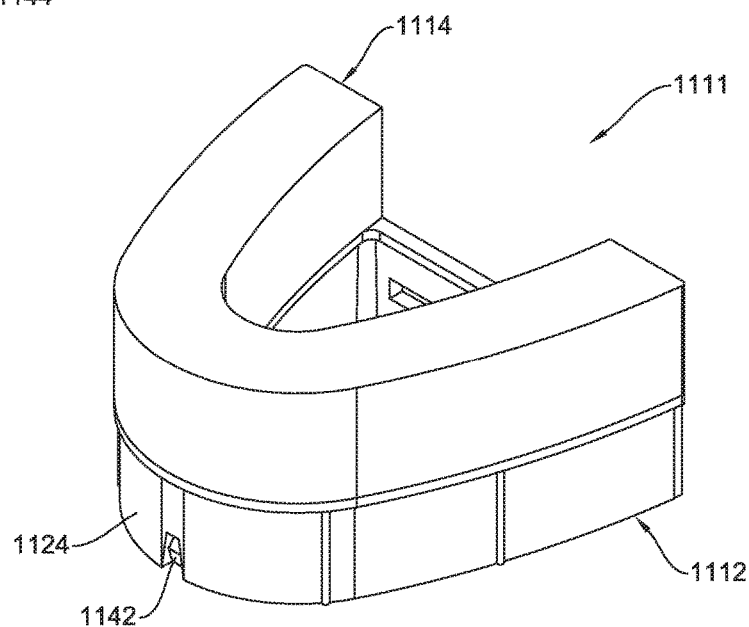
FIG. 117 is a front perspective view of the mounted molding block of FIG. 116.
Figure 118:
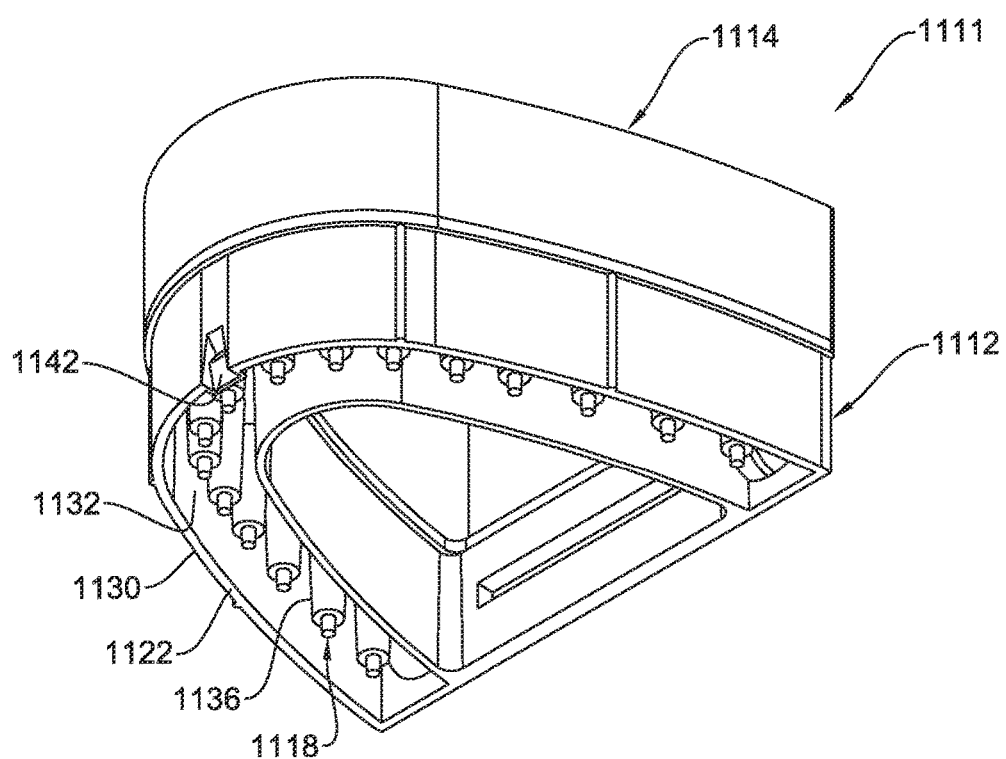
FIG. 118 is another front perspective view of the mounted molding block of FIG. 116.

Referring now to FIGS. 75-115, an example of dental modeling assembly 900 is shown and described. A dental model base 912 and cured modeling block 914 are arranged as a mounted modeling block 911 in FIGS. 75 and 76. The cured modeling block 914 is mounted to a model support surface 928 of the dental model base 912. A plurality of removal dowel pins may be mounted to the dental model base and extend from the model support surface 928 into the cured modeling block 914. A dental model may be formed from the cured modeling block 914 using, for example, a milling machine or other forming device 1019 as shown in FIG. 115. Individual teeth of a dental model may be aligned with one of the removable dowel pins supported in the dental model base 912. Other forming devices such as laser cutters, thermal cutters, sandblasters, and other cutting devices may be used to form a dental model in the cured modeling block 914. An advantage of using the dental model base 912 with the cured modeling block 914 when forming the dental model using a forming device is that the dental model base 912 includes pre-positioned dowel pins that are aligned with each tooth of the dental model. The use of pre-positioned removable dowel pins on a dental model base may eliminate multiple steps previously needed in order to associate each tooth of the dental model with a removable dowel pin and mounted dental model base to the dental model.

FIGS. 77-83 illustrate several exploded views of the dental modeling assembly 900. The dental modeling assembly 900 includes the dental model base 912, the cured modeling block 914, and a mold member 916. The mold member 916 is configured to mount to the dental model base 912 as shown in, for example, FIGS. 84 and 87. The mold member 916 defines a cavity within which the model support surface 928 of dental model base 912 is positioned. A curable modeling material is filled in the cavity to a depth sufficient to cover exposed portions of the removable dowel pins extending from the model support surface 928. The modeling material cures into the cured modeling block 914. The cured modeling block 914 includes the dowel pins mounted thereto. The cured modeling block 914 with at least one of the pins 918 extending from a bottom side thereof can be removed from the dental model base 912 as shown in FIGS. 77-83.

Figure 77:
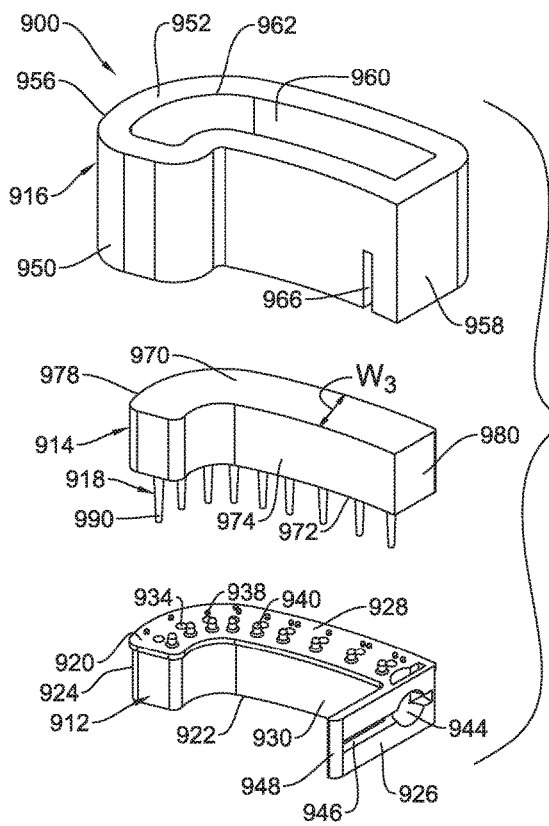
FIG. 77 is an exploded rear perspective view of an example dental modeling assembly including the mounted modeling block of FIG. 75.
Figure 78:
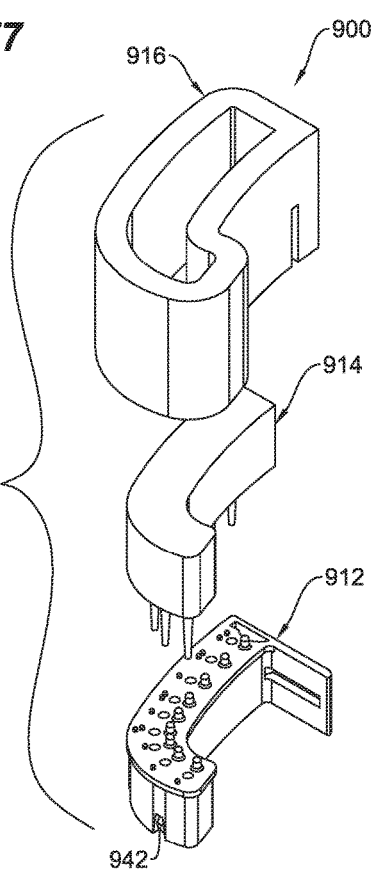
FIG. 78 is an exploded front perspective view of the dental modeling assembly of FIG. 77.
Figure 79:
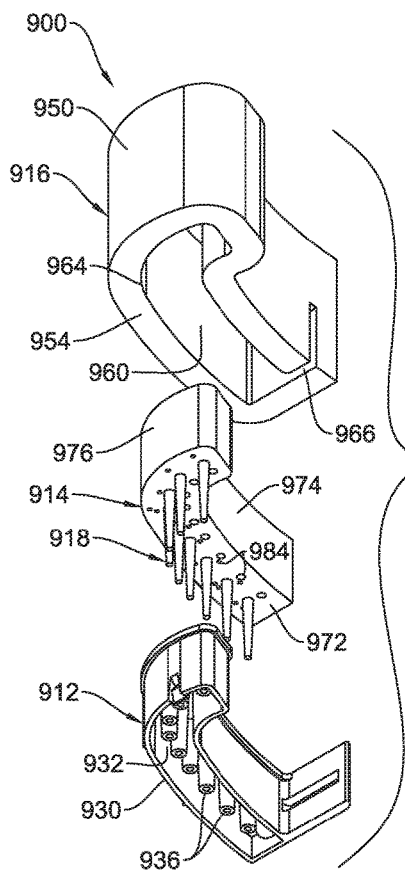
FIG. 79 is another exploded front perspective view of the dental modeling assembly of FIG. 77.
Figure 80:
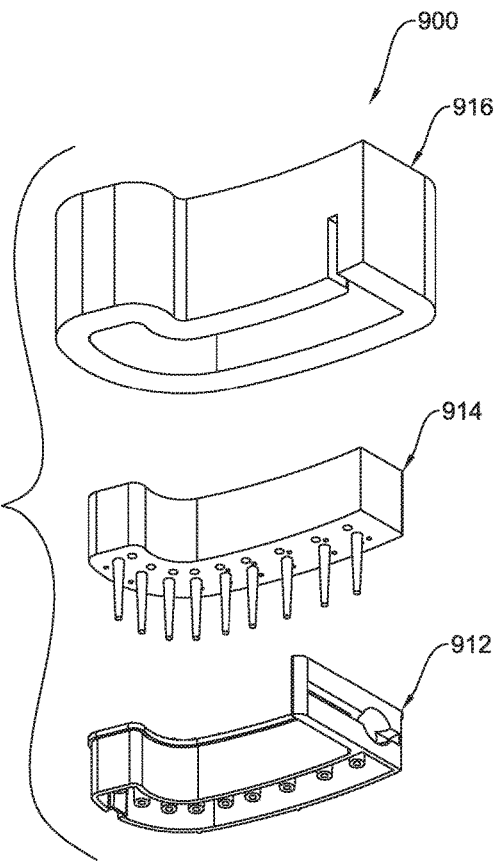
FIG. 80 is another exploded rear perspective view of the dental modeling assembly of FIG. 77.
Figure 81:
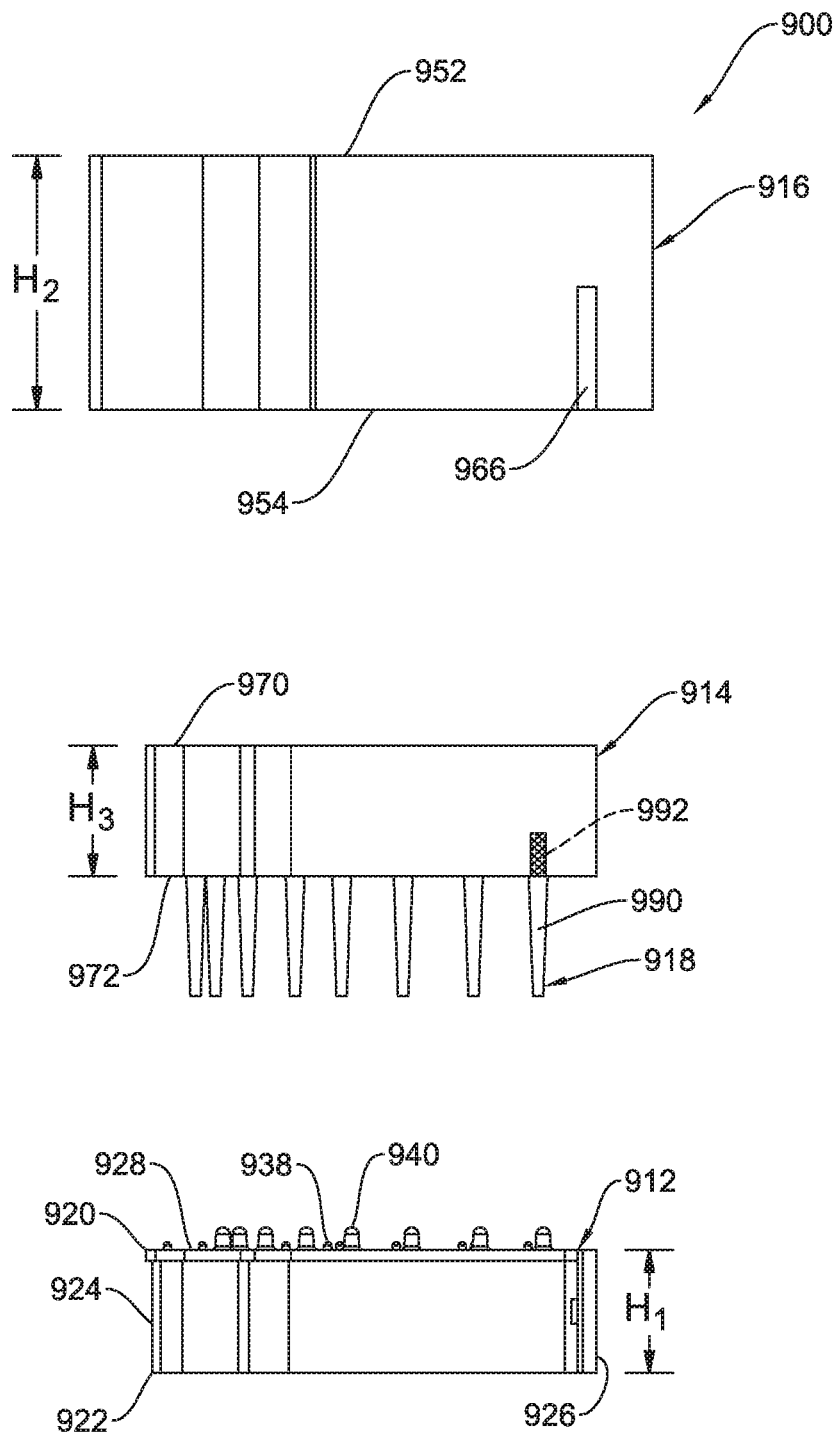
FIG. 81 is an exploded side view of the dental modeling assembly of FIG. 77.
Figure 82:
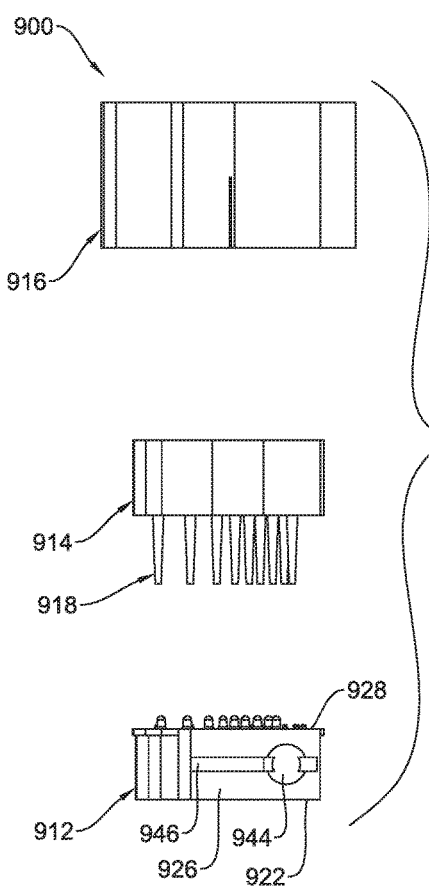
FIG. 82 is an exploded rear view of the dental modeling assembly of FIG. 77.
Figure 83:
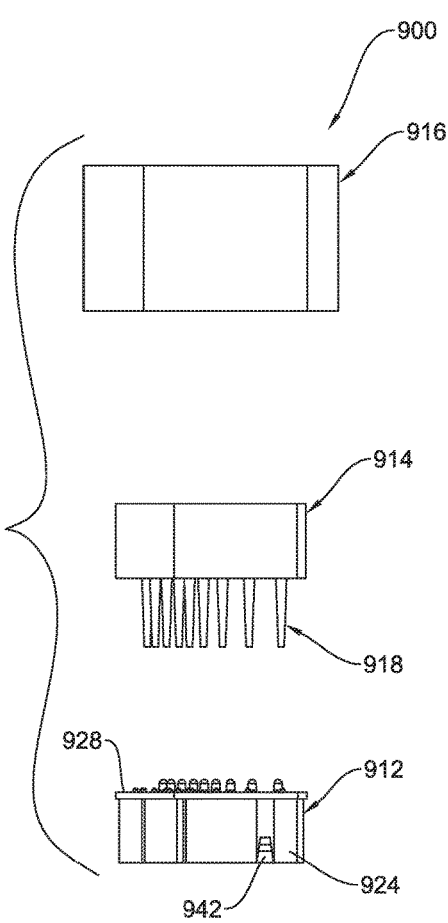
FIG. 83 is an exploded front view of the dental modeling assembly of FIG. 77.
Figure 84:
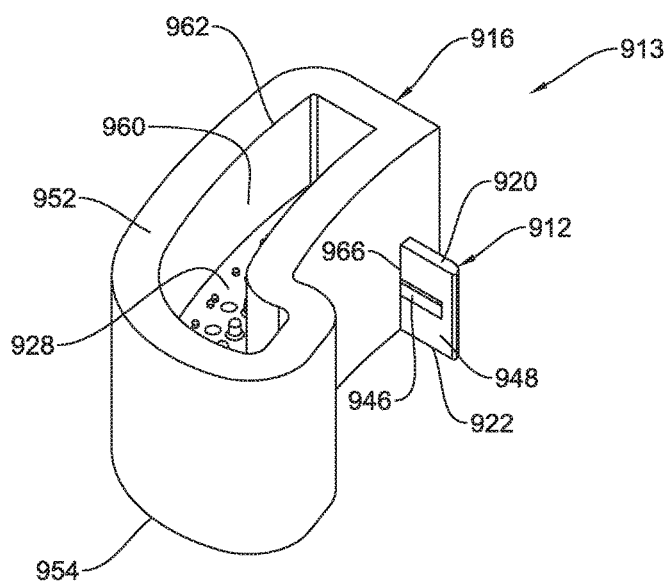
FIG. 84 is a front perspective view of an example mold and base assembly in accordance with the present disclosure.
Figure 85:
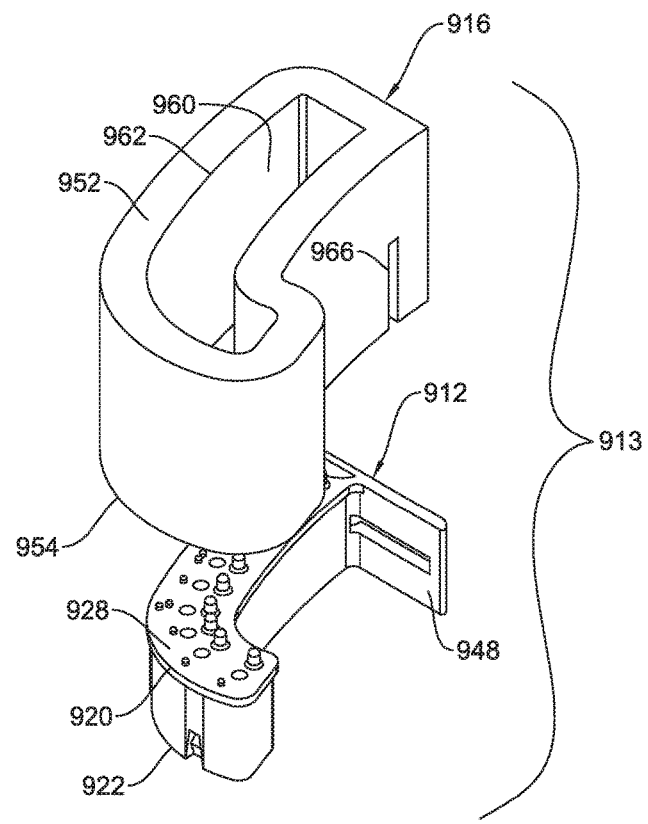
FIG. 85 is an exploded front perspective view of the mold and base assembly of FIG. 84.

Referring primarily to FIGS. 77 and 79, the dental model base 912 includes top and bottom sides 920, 922, front and rear ends 924, 926, the model support surface 928, a wall 930 extending from the model support surface 928 and defining a cavity 932 opposite the model support surface 928. The dental model base 912 also includes a plurality of pin apertures 934 positioned along the model support surface 928. A plurality of pin support protrusions 936 are aligned with the pin apertures 934 and extend into the cavity 932 in a direction opposite the model support surface 928. A plurality of small and large indexing members 938, 940 may be positioned adjacently pin apertures 934. The indexing members 938, 940 may have different arrangements for adjacent pin apertures 934 to help reduce the incidence of improperly returning a tooth model to an incorrect location on the dental model base 912.

The dental model base 912 may also include a latch 942 and at least one socket 944 at opposing front and rear ends 924, 926, respectively. The latch and socket 942, 944 may be generally referred to as a connection arrangement. The latch and socket 942, 944 may be useful for mounting the dental model base 912 to another device such as, for example, an attachment plate that includes mating latch and ball attachment features. The latch and socket 942, 944 may provide a snap-fit connection between the dental model base 912 and another device. The latch and socket 942, 944 may be characterized as providing a quick release attachment to another device using a latch and ball and socket connection arrangement.

The dental model base may further include a slot 946 along the rear end 926. The slot 946 may be defined in an extension 948 that extends laterally from a portion of the dental model base 912. The slot 946 may be sized to receive a mating protrusion feature of, for example, the articulator disclosed in U.S. Pat. No. 4,734,033, which patent is incorporated herein by reference in its entirety.

The dental model base 912 may include different attachment features for mounting to additional devices such as, for example, attachment plates and articulators. The latch 942, socket 944, slot 946 and other attachment features of the dental model base 912 may be interchanged with each other, eliminated, or used in combination with other attachment features.

The dental model base 912 typically has a width $W_1$ (see FIG. 87) measured across the model support surface 928. The dental model base 912 may also have a height $H_1$ (see FIG. 81). The height $H_1$ may be measured from the model support surface 928 along the top side 920 to the bottom side 922. The bottom side 922 is typically defined by the wall 930 at a location furthest away from the model support surface 928.

Figure 137:
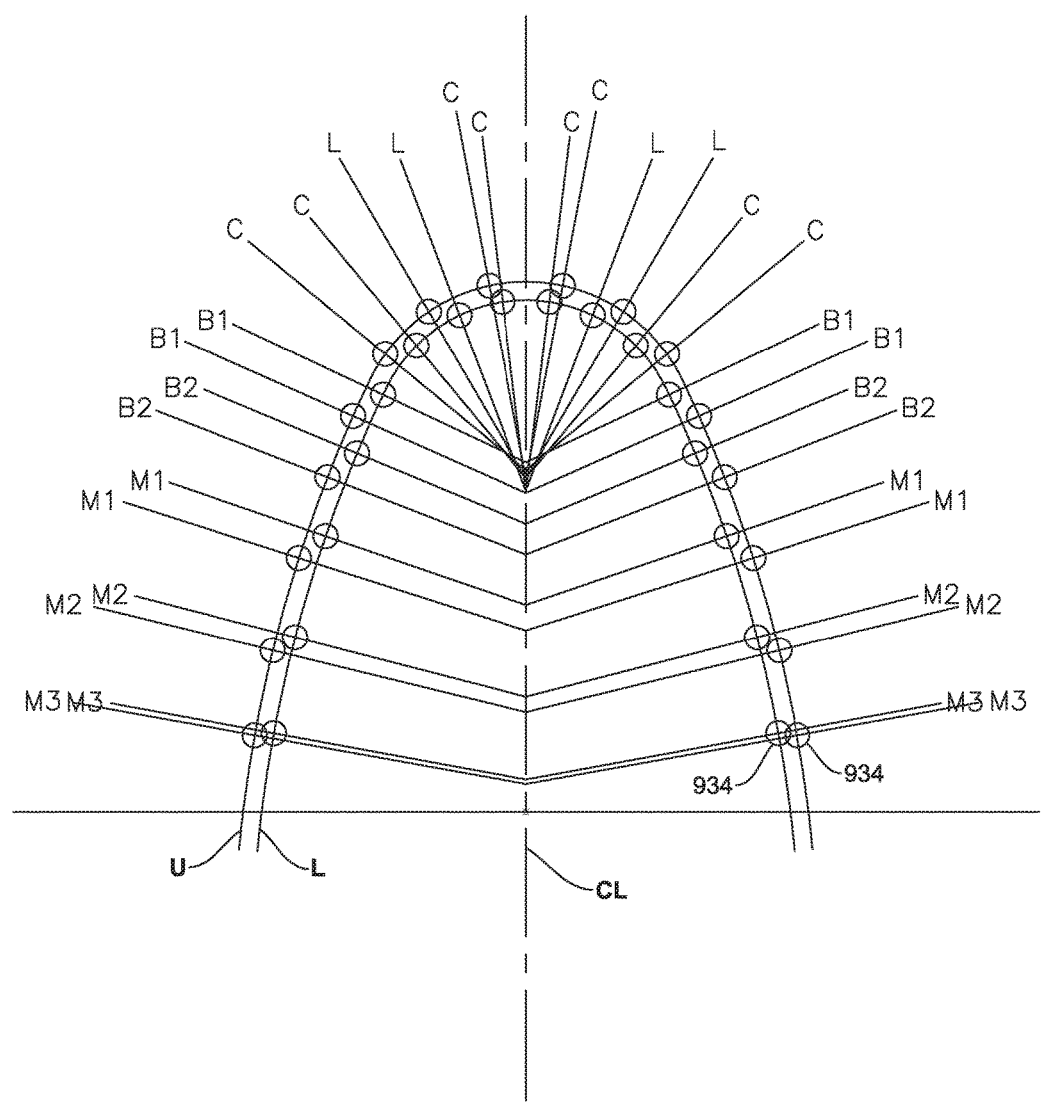

Referring to FIG. 77, the pin apertures 934 are defined along the model support service 928 at predetermined spaced apart locations. Each of the pin apertures 934 is positioned at an average location for a given mouth size (i.e., small, medium, large mouth sizes typically associated with child, youth and adult size mouths). The location of each of the pin apertures 934 has been determined based on hundreds of samples of tooth locations for each mouth size for both the upper and lower teeth. Referring to FIG. 137, an example layout of pin apertures 934 is shown for upper (U) and lower (L) teeth. Each of the lines marked CL, CS, B1, B2, M1, M2, M3 extend from a centerline (CL) outward through one of the pin apertures 934. The average location of teeth for small, medium and large-sized mouths is positioned along each one of these lines that extend from the centerline (CL) (i.e., the location of pin aperture 934 is positioned further from the centerline CL for larger mouth sizes).

Figure 87:
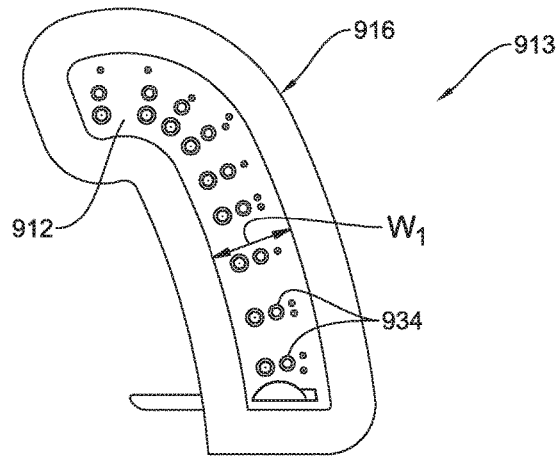
FIG. 87 is a top view of the mold and base assembly of FIG. 84.
Figure 86:
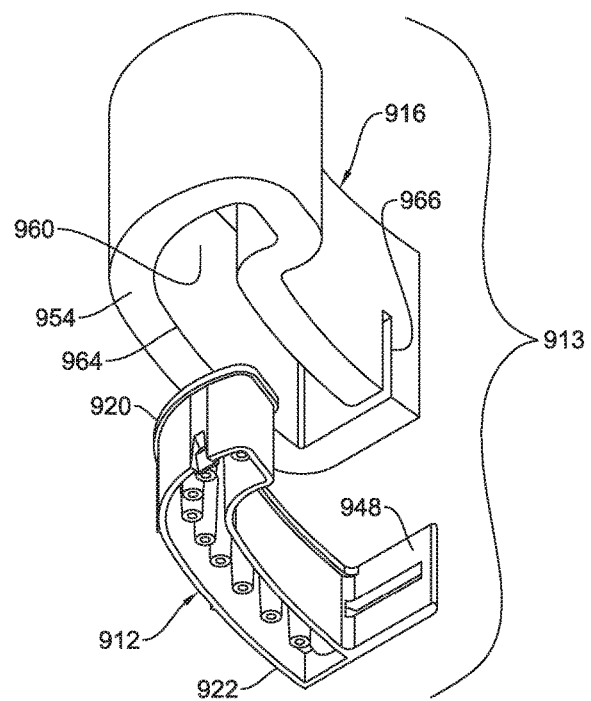
FIG. 86 is another exploded front perspective view of the mold and base assembly of FIG. 84.

The dental model base 912 shown in FIG. 87 includes a portion of one of the upper or lower arcs shown in FIG. 137. The pin apertures 934 are positioned along an arc or include an arc-shaped arrangement. The arrangement of pin apertures 934 follows a natural curvature of a person's mouth and gum line.

Referring again to FIGS. 77 and 79, the cured modeling block 914 includes top and bottom surfaces 970, 972, inner and outer side surfaces 974, 976, front and rear end 978, 980, and a plurality of indexing apertures 984. The indexing apertures 984 define at least in part by the indexing members 938, 940 extending from the model support surface 928 of the dental model base 912. The cured modeling block 914 may include at least one of the dowel pins 918 extending from the bottom surface 972. The dowel pins 918 may include a tapered portion 990 that extends from the cured modeling block 914 and is exposed for positioning within the pin aperture 934. The dowel pins 918 may also include a modeling engagement portion 992 (see FIG. 81) that is engaged within the cured modeling block 914. The modeling engagement portion 992 may include a knurled or roughened surface to promote engagement between the cured modeling block 914 and the dowel pin 918. The modeling engagement portion 992 is typically positioned extending from the model support surface 928 of a dental model base 912 prior to formation of the cured modeling block 914.

The cured modeling block 914 has a height $H_3$ (see FIG. 81) measured between the top and bottom surfaces 970, 972. The cured modeling block 914 may also have a width $W_3$ measured between inner and outer side surfaces 974, 976 (see FIG. 77). Typically, the height $H_3$ is sufficient to provide formation of the dental model without exposing the dowel pins 918.

The cured modeling block 914 typically takes on a size and shape that corresponds to at least a portion of a mold cavity 960 of the mold member 916 (see FIG. 77). In at least some arrangements, a periphery of the cured modeling block 914 substantially matches a periphery of the model support surface 928. In at least some arrangements, the width $W_3$ is substantially equal to the width $W_1$ of the dental model base 912.

The mold member 916 includes a side wall 950, top and bottom surfaces 952, 954, front and rear ends 956, 958, a mold cavity 960, top and bottom openings 962, 964 into the mold cavity 960, and a slot 966 sized to receive the extension 948 of the dental model base 912. The mold cavity 960 has a width $W_2$. The width $W_2$ may be similar in size to the width $W_1$. The mold member 916 may have a height $H_2$ (see FIG. 81) measured between the top and bottom surfaces 952, 954. The height $H_2$ is typically greater than the height $H_3$ of the cured modeling block 914. In at least some arrangements, the height $H_2$ is greater than the height $H_1$.

The mold cavity 960 is typically sized to substantially match the periphery of the model support surface 928 of the dental model base 912. In some arrangements, the mold member 916 creates a seal around a periphery of the model support surface 928 that limits the passage of a curable modeling material that is in an uncured state. In some arrangements, the mold member 916 may be mounted to the dental model base 912 such that at least a portion of the model support surface 928, including the modeling engagement portion 992 of the dowel pins 918 (which are mounted in the pin aperture 934), is exposed within the mold cavity 960.

Figure 88:
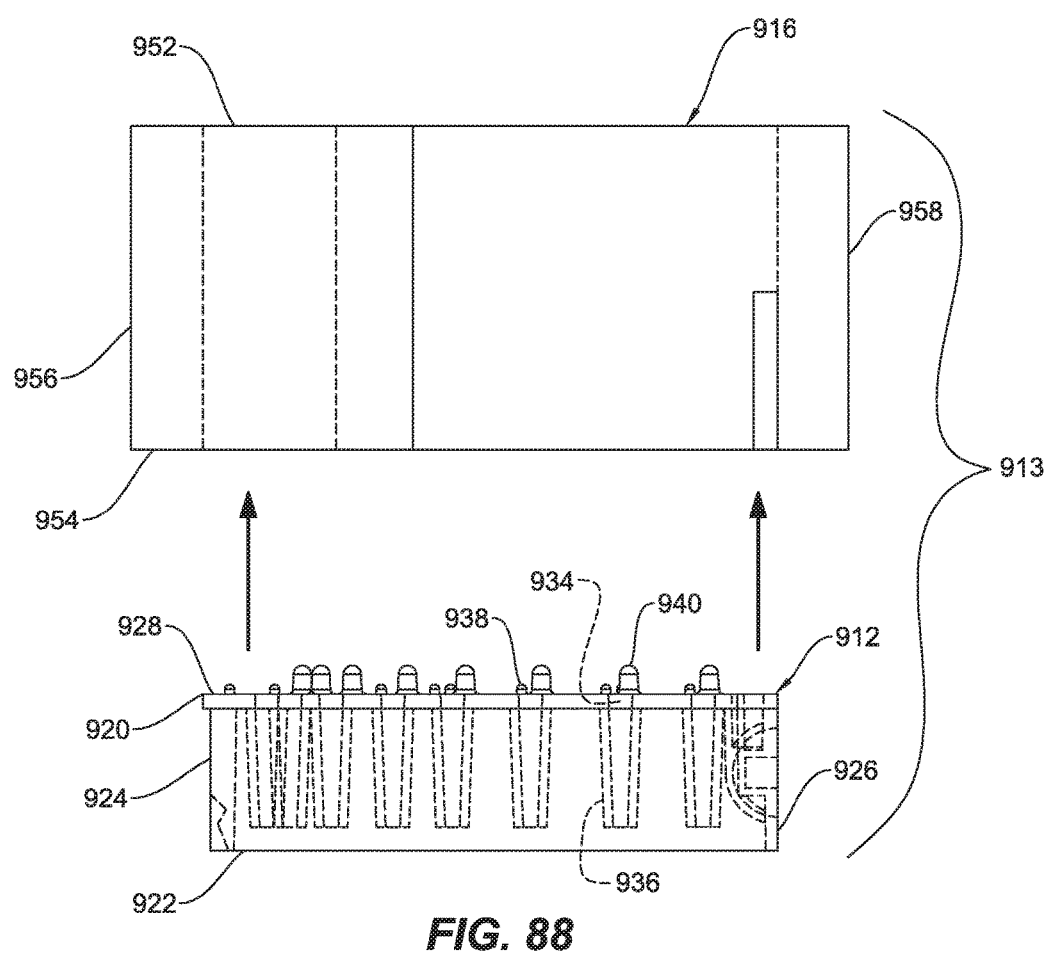
FIG. 88 is an exploded side view of the mold and base assembly of FIG. 84.
Figure 93:
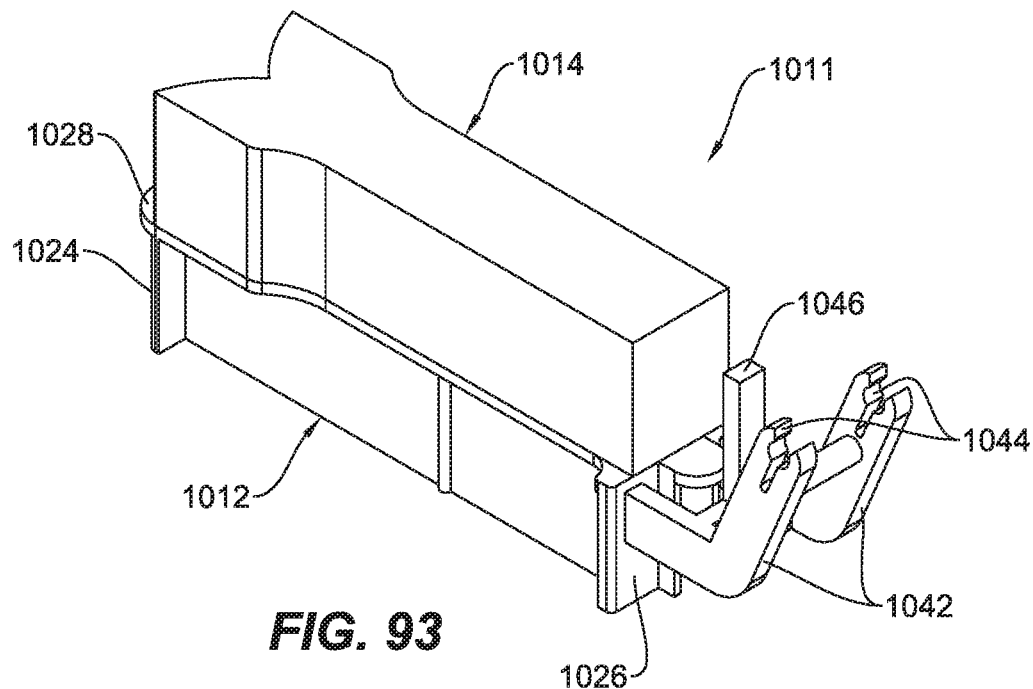
FIG. 93 is a rear perspective view of another example mounted modeling block in accordance with the present disclosure.
Figure 94:
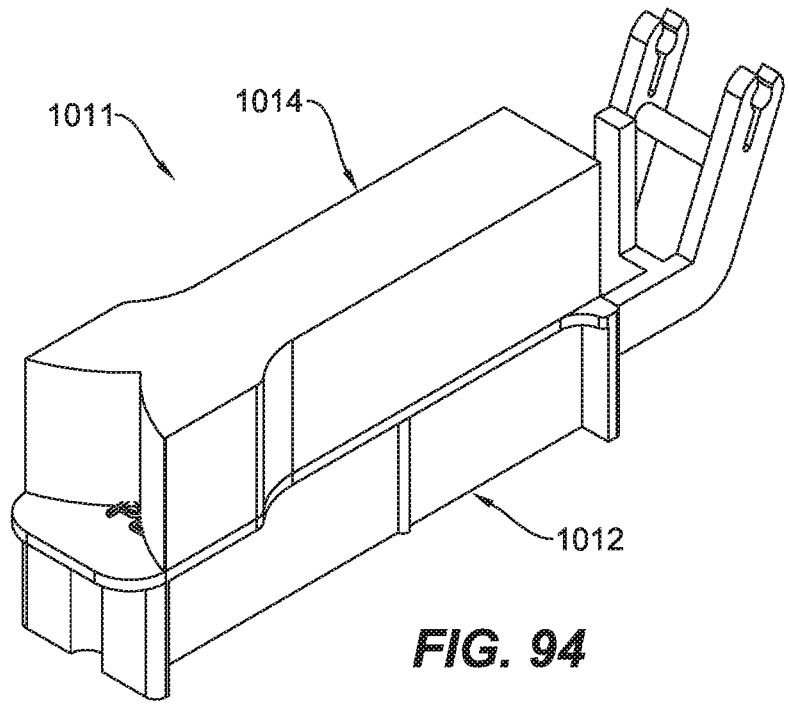
FIG. 94 is a front perspective view of the mounted molding block of FIG. 93.
Figure 95:
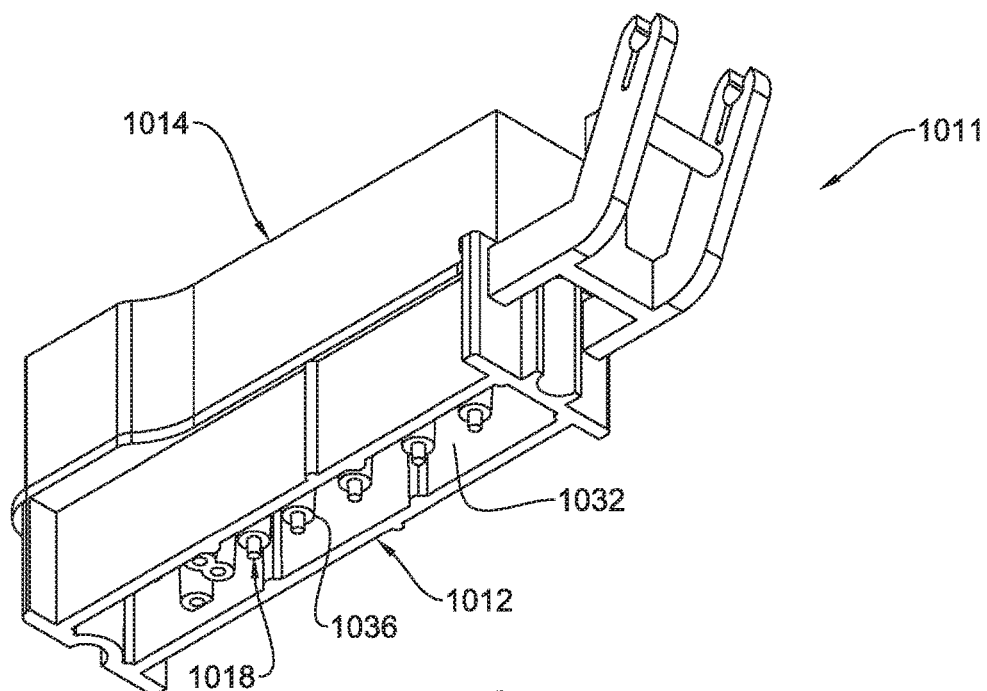
FIG. 95 is another rear perspective view of the mounted molding block of FIG. 93.
Figure 96:
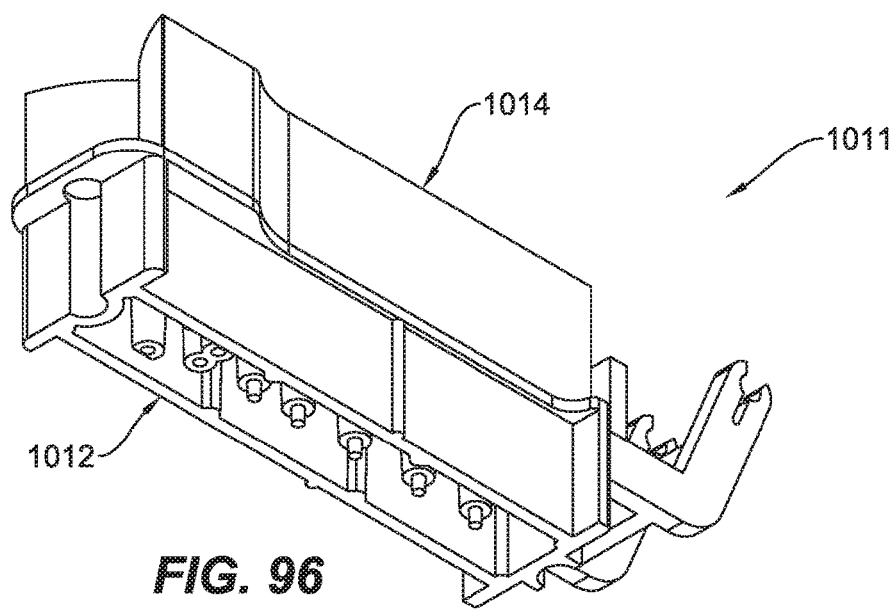
FIG. 96 is another front perspective view of the mounted molding block of FIG. 93.

Mold member 916 may be mounted to the dental model base 912 in a number of different arrangements. In one arrangement, the dental model base is inserted into the mold cavity 960. FIG. 88 illustrates insertion of the dental model base 912 into the bottom opening 964 of the mold cavity 960. FIG. 88 illustrates the dental model base 912 positioned within the mold cavity 960 with only the extension 948 extending through the slot 966 being positioned outside of the mold cavity 960.

In other arrangements, the dental model base 912 may be inserted through the top opening 962. In other examples, the mold member 916 may be positioned sitting on the model support surface 928 with the bottom surface 954 contacting the model support surface 928. In one example, the mold member 916 comprises an elastic material such as, for example, rubber. The mold member 916 may be deformable to promote insertion of the dental model base 912 into the mold cavity 960, and then be deformable again to remove the mold member 916 after the cured modeling block 914 has been formed within the mold cavity 960. In one example, the elastic material used for the mold member 916 comprises one of a vulcanizing rubber, silicone rubber, and urethane rubber. In one example, the mold member 916 is formed using a heated press. The properties of the mold member 916 (i.e., color, ozone protection, stiffness, etc.) can be altered using an elastomizer formulate. The material selected for creating the mold member 916 may be dependent at least in part on the type of material being used as to create the cured modeling block 914.

In other examples, the mold member 916 is mounted to the dental model base 912 using, for example, an adhesive, fasteners, brackets, clamps, interference fits, or any combination of attachment features. Typically, the mold member 916 is mounted to the dental model base 912 in a manner in which the mold member 916 may be dismounted from the dental model base 912 without permanent damage to the mold member 916. However, it may be possible to provide mounting of the mold member 916 to the dental model base 912 in a way that requires some permanent damage (i.e., cutting, cracking, etc.) of the mold member 916 in order to dismount from the dental model base 912.

With the mold member 916 mounted to the dental model base 912, at least a portion of the mold cavity 960 of the mold member 916 is arranged above and adjacent to the model support surface 928. A volume of curable modeling material is inserted into the mold cavity 960 typically through the top opening 962. The curable modeling material is typically filled to a sufficient depth within the mold cavity 960 to completely cover the portions of dowel pins 918 and indexing members 938, 940 that are exposed within the mold cavity 960. In other arrangements, the curable modeling material may be inserted into the mold cavity 960 through a different opening such as an opening defined in the side wall 950 or through one of the pin support protrusions 936 that does not include a dowel pin 918 inserted therein.

Figure 75:
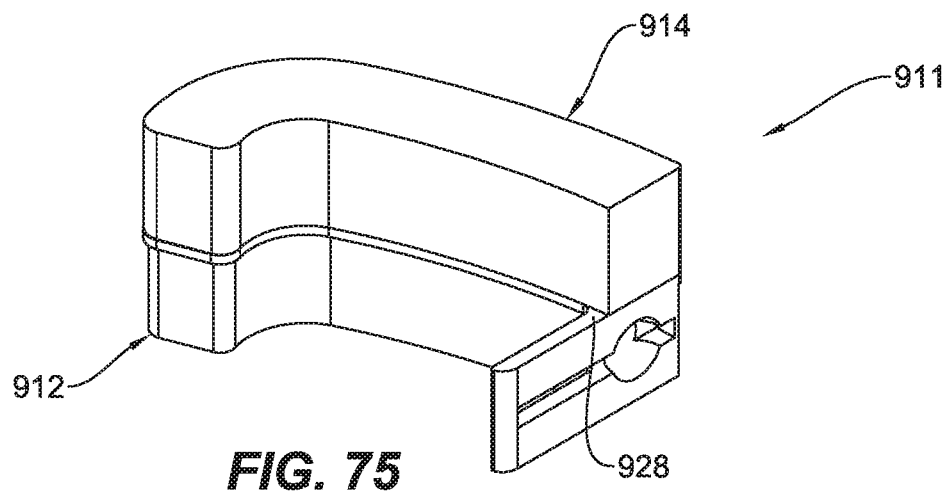
FIG. 75 is a rear perspective view of an example mounted modeling block in accordance with the present disclosure.
Figure 76:
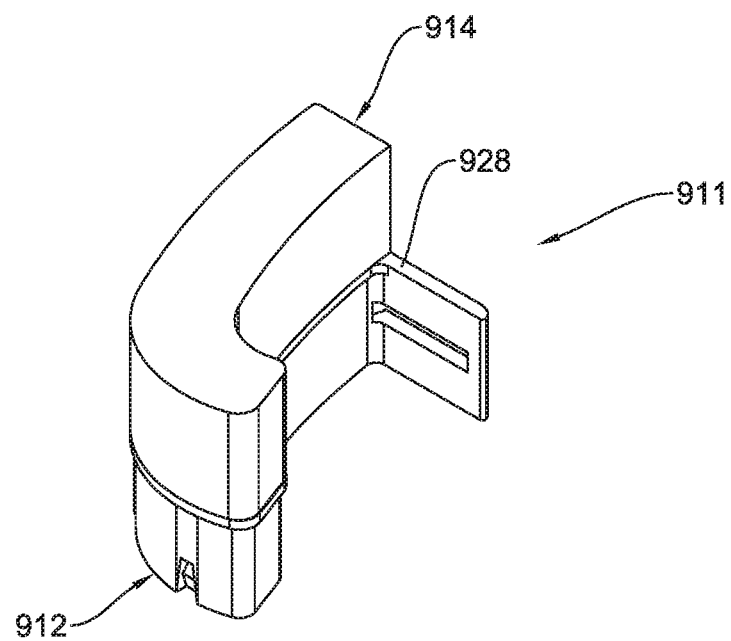
FIG. 76 is a front perspective view of the mounted modeling block in FIG. 75.

After the curable modeling material has cured to form the cured modeling block 914, the mold member 916 is removed from the dental model base 912 to provide the mounted modeling block 911 shown in FIGS. 75 and 76. The combination of the dental model base 912 and mold member 916 prior to creating the cured modeling block 914 may be referred to as a mold and base assembly 913 as shown in FIGS. 84-88. The mold member 916 is shown by itself in various views in FIGS. 89-92.

The cured modeling block 914 may comprise various materials such as, for example, epoxy, polymer material such as plastic, hardened stone, casting resin, foam, and commercial products such as duoMatrix™. Any plastic material used as the cured modeling block 914 may have different properties than the material used for the dental model base 912 such as, for example, a lower melting point than the plastic material used for dental model base 912. Various methods of filling at least a portion of the mold cavity 960 with a material that defines the cured modeling block 914 may be used depending on the type of material.

Referring now to FIGS. 93-115, another example dental modeling assembly 1000 is shown and described. The dental modeling assembly 1000 provides a mounted modeling block 1011 as shown in FIGS. 93-96. The mounted modeling block 1011 includes a cured modeling block 1014 mounted to a dental model base 1012. A dental model 1082 may be formed from the cured modeling block 1014 while mounted to the dental model base 1012 (see FIG. 115) using, for example, a forming device 1019. The forming device 1019 may be, for example, a milling machine or cutting device such as, for example, a laser, heat, or other cutting device. Each tooth of the dental model 1082 may be aligned with a dowel pin mounted to the dental model base 1012. The dowel pins are pre-positioned on a dental model base 1012 to be aligned with teeth of the dental model 1082 so that separation of any one of the teeth of the dental model 1082 from the remaining portions of the dental model has at least one dowel pin connected thereto.

The dental modeling assembly 1000 is shown in various exploded views in FIGS. 97-103. The dental modeling assembly 1000 includes the dental model base 1012, the cured modeling block 1014, and a mold member 1016. Prior to the formation of the cured modeling block 1014, the dental model base 1012 and mold member 1016 may be used together as a mold and base assembly 1013 as shown in FIGS. 104-109.

The dental model base 1012 includes top and bottom sides 1020, 1022, front and rear ends 1024, 1026, a model support surface 1028, a wall 1030 extending in a direction opposite the model support surface 1028, and a cavity 1032 defined by the wall 1030 and positioned opposite the model support surface 1028. A plurality of pin apertures 1034 may be defined along the model support surface 1028. A plurality of pin support protrusions 1036 may extend into the cavity 1032 in a direction opposite the model support surface 1028 and in alignment with each of the pin apertures 1034. A plurality of small and large indexing members 1038, 1040 may be arranged along the model support surface 1028 in association with at least some of the pin apertures 1034.

The dental model base 1012 may include a plurality of articulator components such as, for example, at least one attachment arm 1042, a connection feature 1044 associated with each of the attachment arms 1042, and a separation post 1046. The attachment arms 1042 and connector features 1044 may be configured to mate with articulator components of another dental model base or opposing base such as described in U.S. Published Application No. 2006/0281043.

The attachment arms 1042 and connector features 1044 may connect to another dental model base or opposing base with a hinged connection that provides relative pivotal or hinged movement between the connected dental model bases. The separation post 1046 may be arranged to contact a portion of the dental model base or opposing base that is connected to the dental model base 1012 (i.e., contact an opposing separation post of that device) to provide a position stop for such relative rotation.

Various aspects of the dental model base 1012 may be modified to increase or decrease flexibility of the attachment arms 1042 to provide modification of the amount of articulation that is possible between dental model base 1012 and another base connected to the attachment arm 1042. In one example, portions of the attachment arm 1042 may be modified in shape or size to alter flexibility. In other examples, portions of the attachment arm 1042 may have a different material composition than the remaining portion of the dental model base 1012. In other examples, the angle which the attachment arm 1042 extend from the rear end 1026, or the length and thickness of the support structures extending between attachment arms 1042 may be modified to offer the flexibility and/or articulation possible for the dental model base 1012.

The dental model base 1012 may also include at least one marker along an exterior thereof that is visible when the cured modeling block 1014 is mounted to the dental model base 1012. The marker may be a molar marker 1048 as shown in FIG. 115 that indicates the position of a first molar of a pre-positioned pin aperture 1034 and a dowel pin 1018 that is positioned in the pin aperture 1034. The molar marker 1048 may be used as an initial position marker (i.e., a zero or starting location) during formation of a dental model using, for example, the forming device 1019 shown in FIG. 115.

Figure 99:
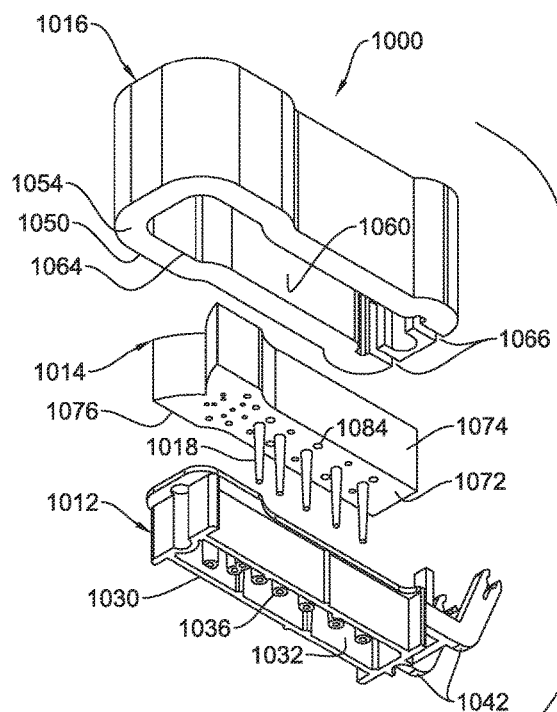
FIG. 99 is another front perspective view of the dental modeling assembly of FIG. 97.
Figure 100:
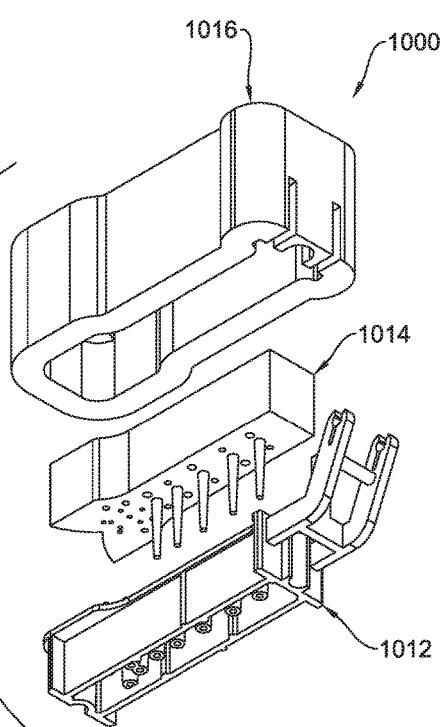
FIG. 100 is another rear perspective view of the dental modeling assembly of FIG. 97.
Figure 103:
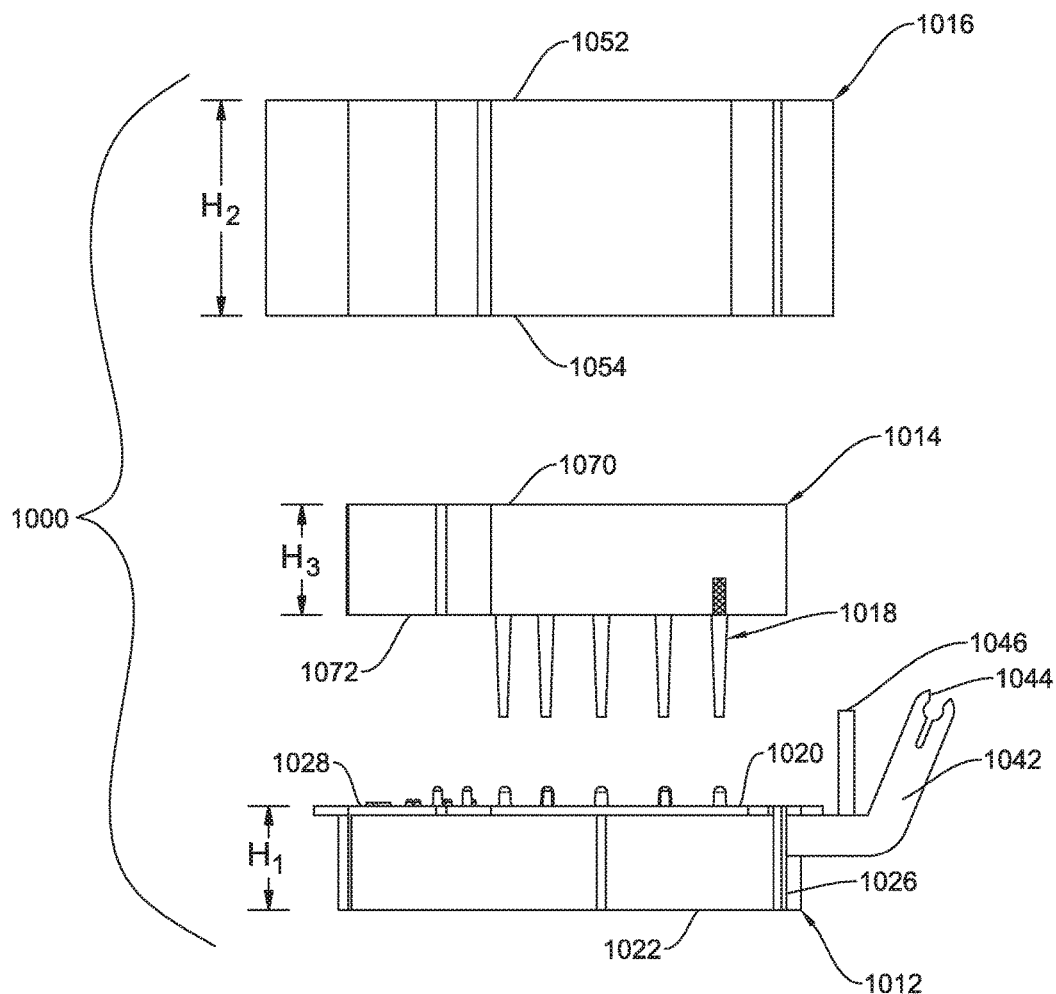
FIG. 103 is an exploded side view of the dental modeling assembly of FIG. 97.
Figure 104:
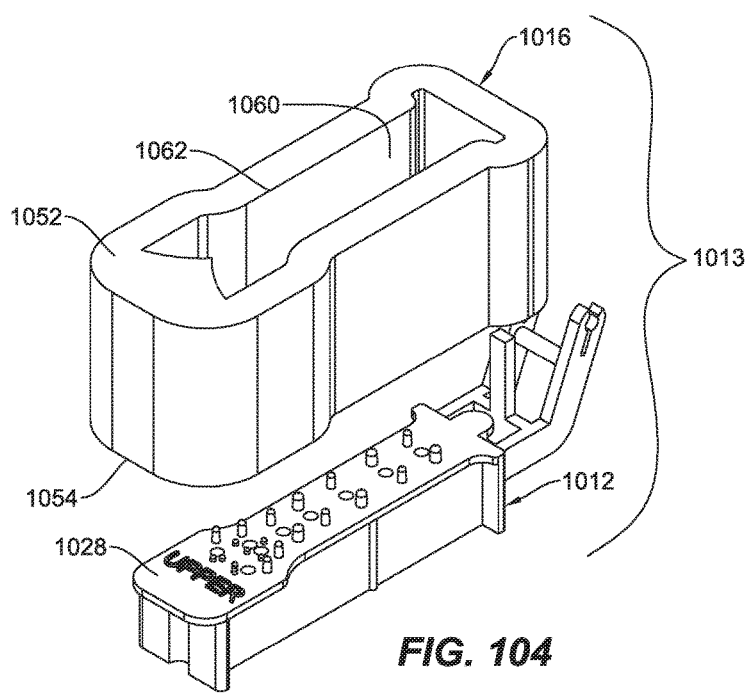
FIG. 104 is a front perspective view of a mold and base assembly in accordance with the present disclosure.
Figure 105:
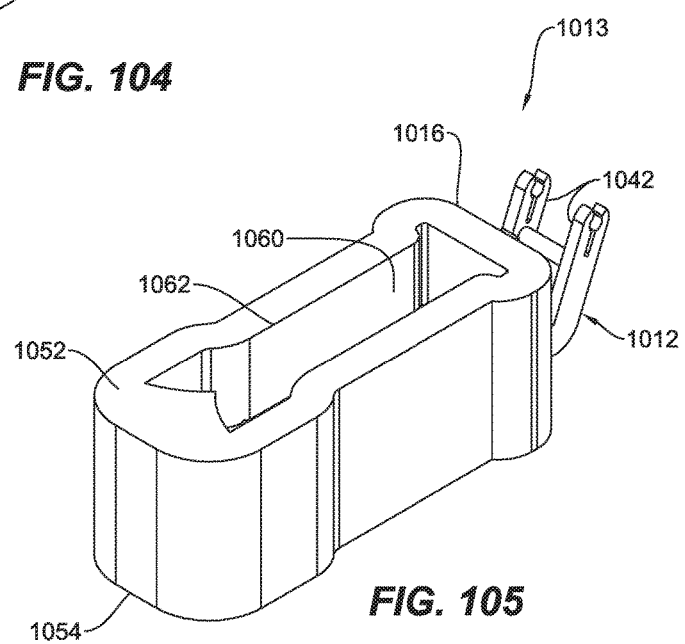
FIG. 105 is an exploded front perspective view of the mold and base assembly of FIG. 104.
Figure 106:
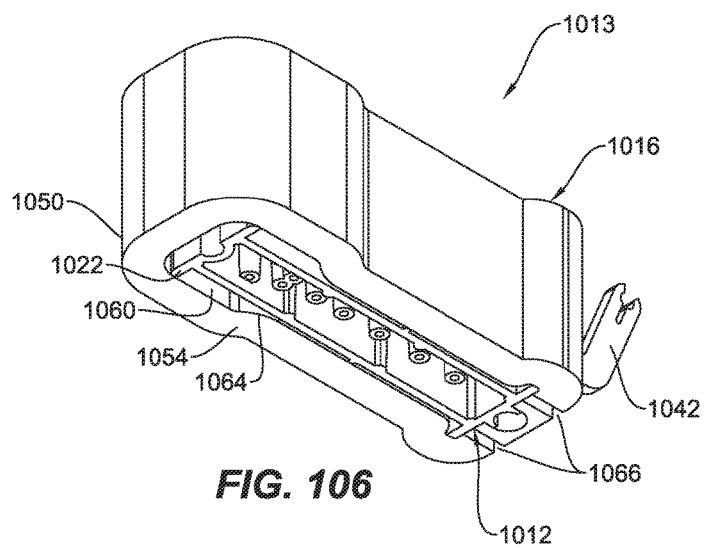
FIG. 106 is another front perspective view of the mold and base assembly of FIG. 104.
Figure 107:
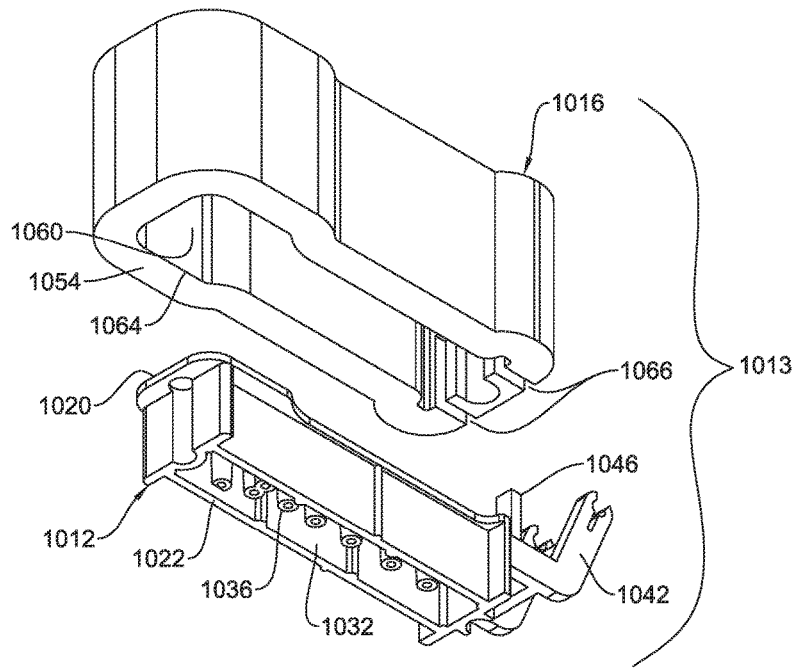
FIG. 107 is another exploded front perspective view of the mold and base assembly of FIG. 104.

The cured modeling block 1014 may include top and bottom surfaces 1070, 1072, first and second side surfaces 1074, 1076, front and rear ends 1078, 1080, and a plurality of indexing apertures 1084 (see FIGS. 97 and 99). The cured modeling block 1014 may have a height $H_3$ and a width $W_3$ (see FIGS. 97 and 103). The cured modeling block 1014 may have many of the same features, properties and functionality as the cured modeling block 1014 described above with references to FIGS. 75-92. The cured modeling block 1014 may have a shape, particularly at the front end 1078, which accommodates the possible location of dowel pins 1018 on the dental model base 1012. For example, the dental model base 1012 may include pairs 1033 and 1035 of anterior pin apertures near the front end 1024 (see FIG. 109). Dowel pins 1018 positioned in one of the anterior pairs of openings 1033, 1035 may be aligned with anterior teeth of the teeth model. There may be some separation of the cured modeling block 1014 at the front end 1078 (i.e., a flared portion) that also provides coverage of dowel pins 1018 positioned in the anterior pairs of apertures 1033, 1035 with enough separation to permit cutting between adjacent teeth models separately that correspond to pairs of openings 1033, 1035.

Figure 138:
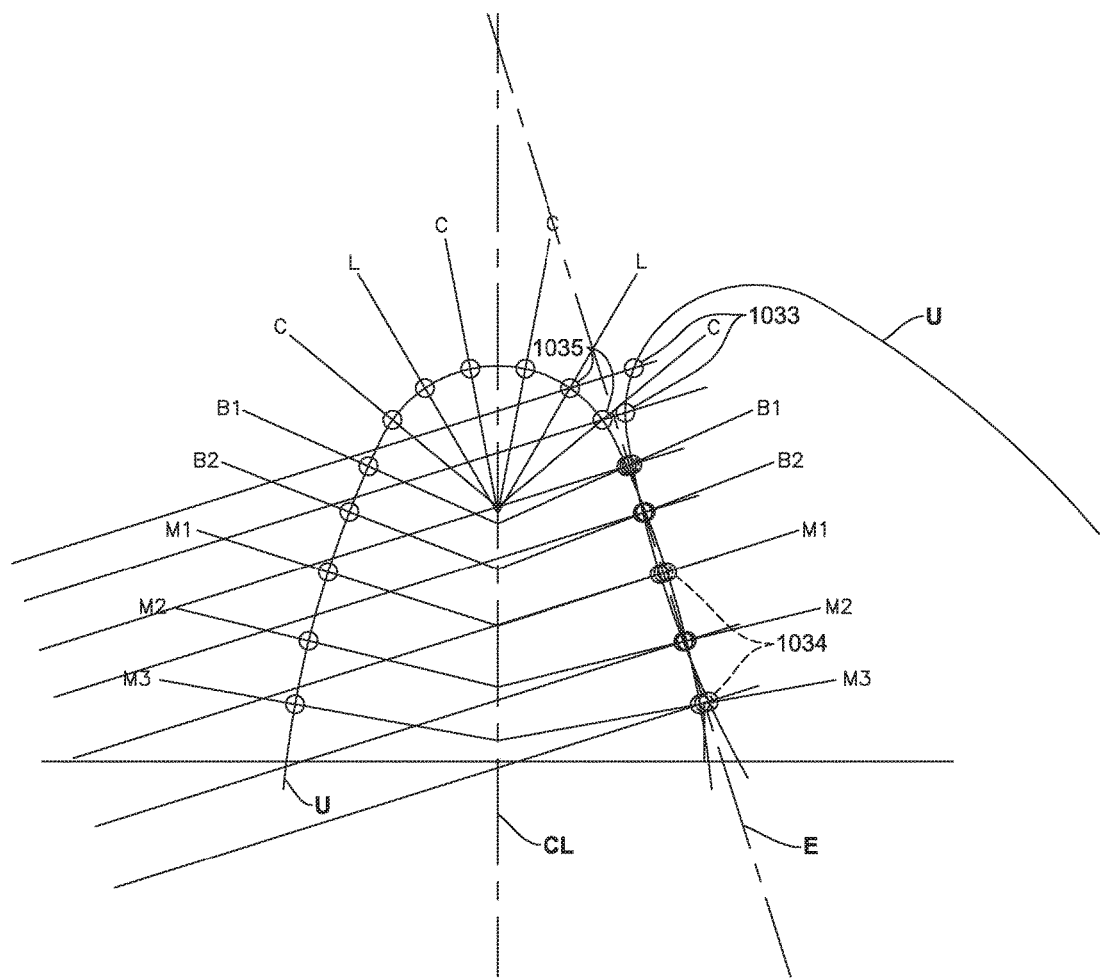

The pin apertures 1034 of dental model base 1012 are pre-positioned to represent average teeth locations for different mouth sizes (i.e., small, medium, and large mouth sizes). Referring to FIGS. 137 and 138, the spacing and orientation of pin apertures 1034 may be determined by an average location of pin apertures when overlapping, for example, the upper arc (U) of pin apertures from FIG. 137 as shown in FIG. 138. The rear most five pin apertures in the dental model base 1012 are aligned linearly in a straight line creating by taking such averaged positions. The pairs of anterior apertures 1033, 1035 may follow the arced portion of apertures of the full arc beyond the five rear most pin apertures (see FIG. 138). The five rear most apertures are arranged linearly along the line (E) in FIG. 138 while the pairs 1033, 1035 are positioned along the arcs (U). The five rear most linearly arranged apertures maintain the same linear or longitudinal space relative to each other while having some variation in a lateral or side-to-side direction as compared to the arc arrangement shown in FIG. 138.

The mold member 1016 may include an outer side wall 1050, a top and bottom surfaces 1052, 1054, front and rear ends 1056, 1058, a mold cavity 1060, and top and bottom openings 1062, 1064 into the mold cavity 1060. The mold member 1016 may also include at least one slot 1066 sized to accommodate portions of the attachment arm 1042 of the dental model base 1012 when inserting at least a portion of the dental model base 1012 into the mold cavity 1060. The size and shape of the slot 1066 may define at least in part a maximum distance of the dental model base 1022 can be inserted into the mold cavity 1060.

Figure 108:
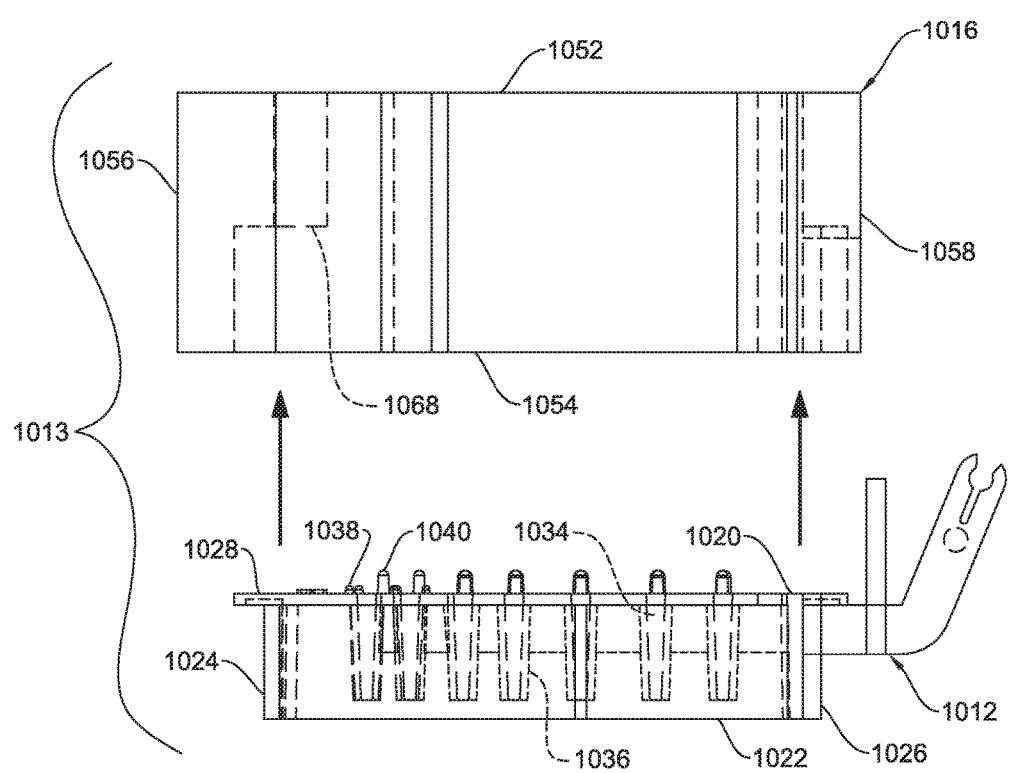
FIG. 108 is an exploded side view of the mold and base assembly of FIG. 104.
Figure 109:
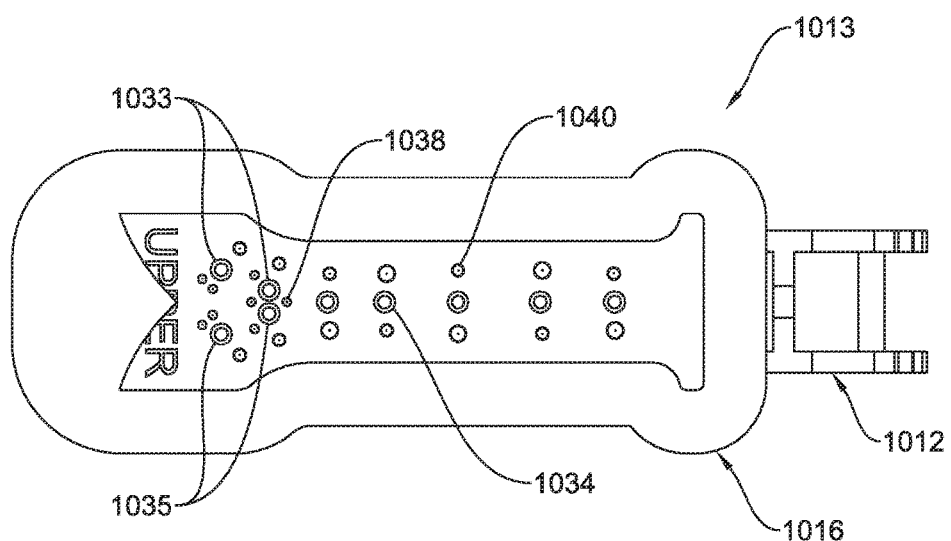
FIG. 109 is a top view of the mold and base assembly of FIG. 104.
Figure 111:
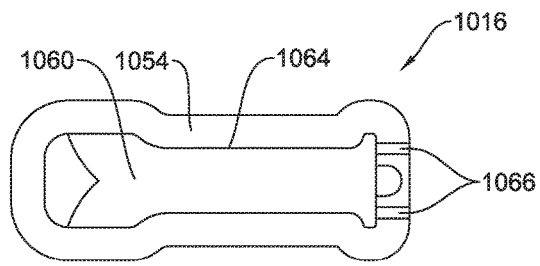
FIG. 111 is a bottom view of the mold member of FIG. 110.
Figure 113:
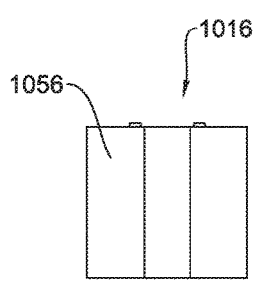
FIG. 113 is a front view of the mold member of FIG. 110.
Figure 112:
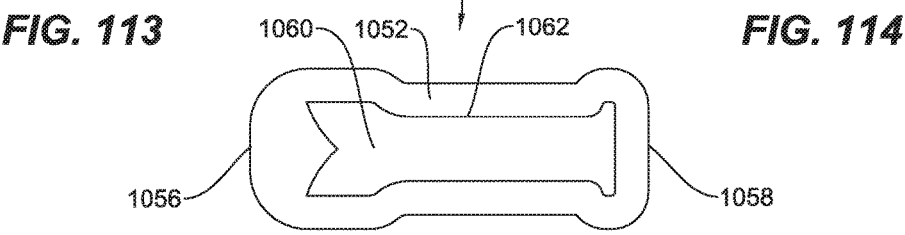
FIG. 112 is a top view of the mold member of FIG. 110.
Figure 114:
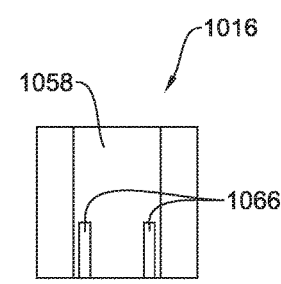
FIG. 114 is a rear view of the mold member of FIG. 110.
Figure 110:
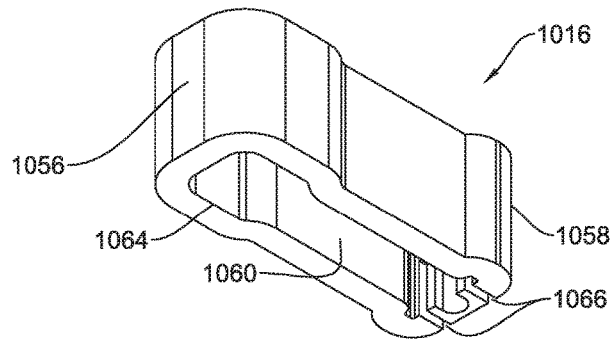
FIG. 110 is a front perspective view of another mold member in accordance with the present disclosure.

The mold member 1016 may also include an extension 1068 that protrudes into the mold cavity 1060 (see FIG. 97). The extension 1068 defines at least in part the flared or diverging portions of the cured modeling block 1014 at its front end 1078. The extension 1068 may extend only partially from the top surface 1052 to the bottom surface 1054 as shown by comparison of, for example, the constructions shown in FIGS. 97 and 99. FIG. 108 illustrates in broken line the extension 1068. The extension 1068 may also define at least in part a maximum distance in which the dental model base 1012 may be inserted into the mold cavity 1060 as the model support surface 1028 of the dental model base 1012 contacts the extension 1068.

The mold member may comprise various materials, features and functionality, and be mounted to the dental model base 1012 similar to mold member 916 and dental model base 912 described above with reference to FIGS. 75-92.

Referring now to FIGS. 116-137, another example dental modeling assembly 1100 is shown and described. The dental modeling assembly 1100 may include a cured modeling block 1114 mounted to a dental model base 1112 in the form of a mounted modeling block 1111 (see FIGS. 116-118). A dental model may be formed directly into the cured modeling block 1114 while mounted to the dental model base 1112. In one example, the dental model may be formed using a milling or cutting device that creates the dental model from the cured modeling block 1114 based on data representing a digital model of a person's teeth. The digital model may be formed by scanning a person's teeth to create a plurality of digital images, using software to combine the digital images to form a digital 3-D model of the teeth.

The dental modeling assembly 1100 includes the dental model base 1112, the cured modeling block 1114, and a mold member 1116 as shown in the various exploded views of FIGS. 119-125. The dental model base 1112 and mold member 1116 may be arranged as an assembly prior to formation of a cured modeling block 1114 as a mold and base assembly 1113 (see FIGS. 126-131).

The dental model base 1112 may include top and bottom sides 1120, 1122, front and rear ends 1124, 1126, a model support surface 1128, and a wall 1130 extending opposite the model support surface 1128. The dental model base 1120 may also include a cavity 1132 defined by the wall 1130 opposite the model support surface 1128, a plurality of pin apertures 1134 defined in the model support surface 1128, and a plurality of pin support protrusions 1136 positioned in the cavity 1132 that extend opposite the model support surface 1128 and in alignment with the pin apertures 1134. A plurality of small and large indexing members 1138, 1140 may be positioned on the model support surface 1138 in association with the pin apertures 1134.

The dental model base 1112 may include latch and socket features 1142, 1144 positioned at front and rear ends 1124, 1126, respectively. A slot 1146 may be defined in a surface at the rear end 1126. Similar to the dental model base 912 described above, the latch and socket 1142, 1144 and slot 1146 may assist in mounting the dental model base 1112 to an articulator or other device such as an attachment plate.

Figure 125:
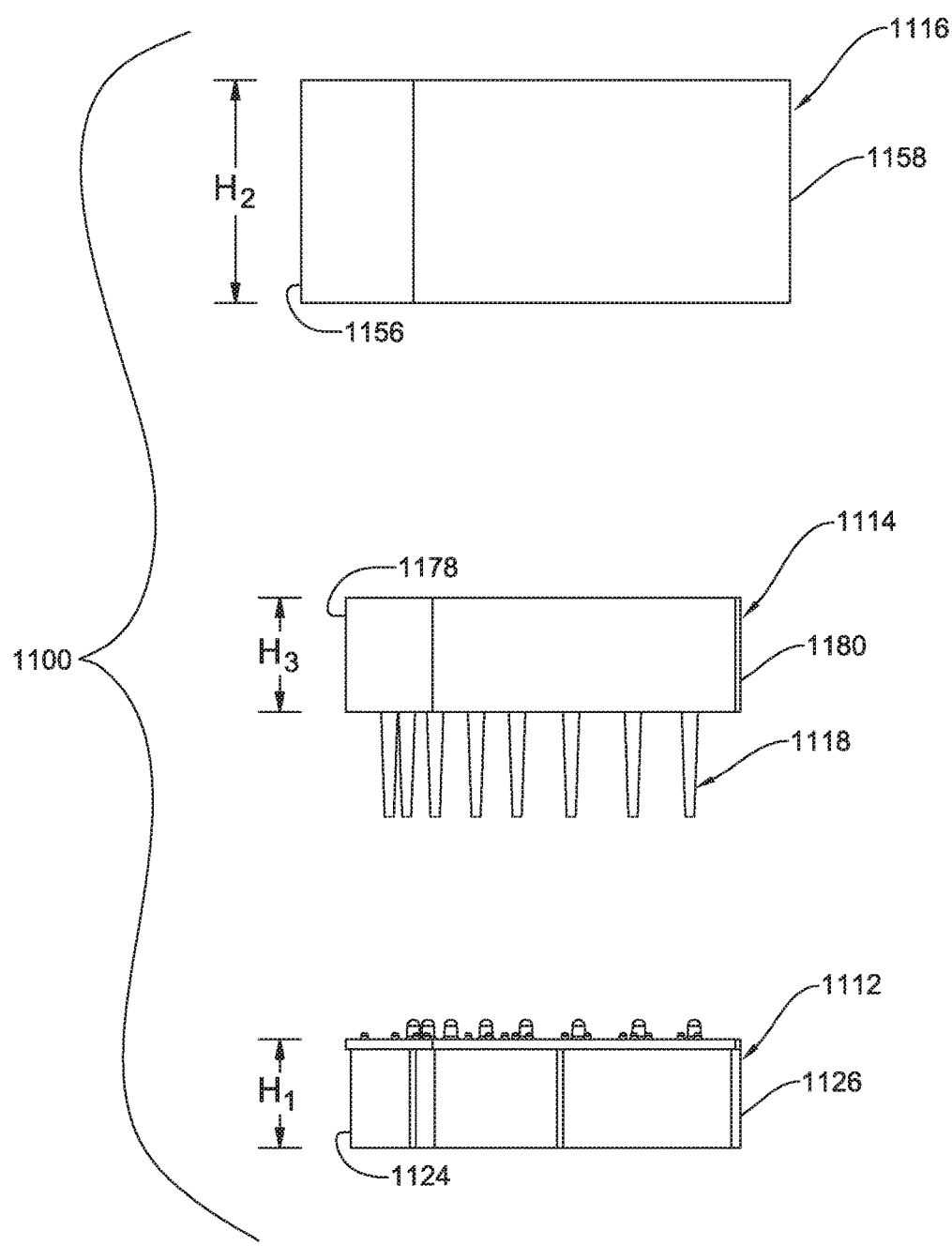
FIG. 125 is an exploded side view of the dental mounting assembly of FIG. 119.
Figure 127:
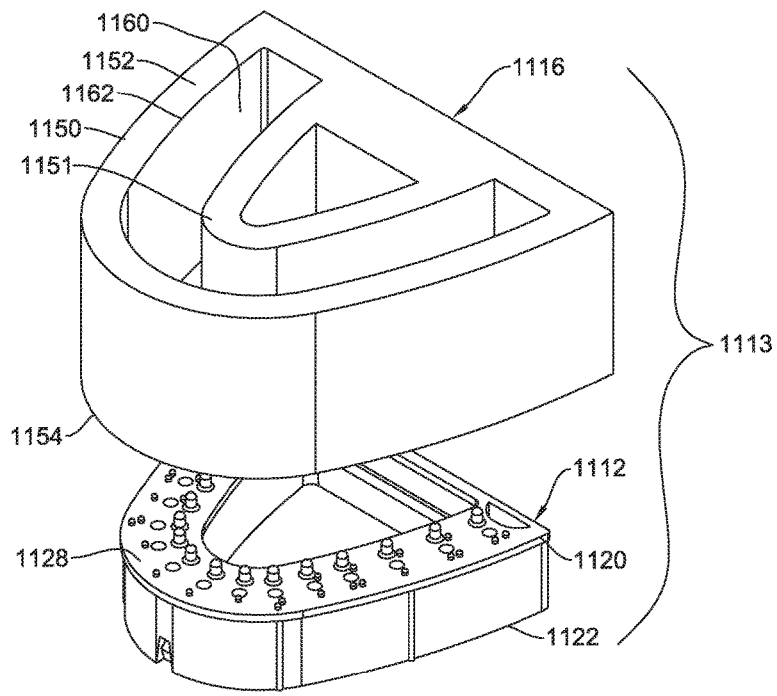
FIG. 127 is an exploded front perspective view of the mold and base assembly of FIG. 126.
Figure 126:
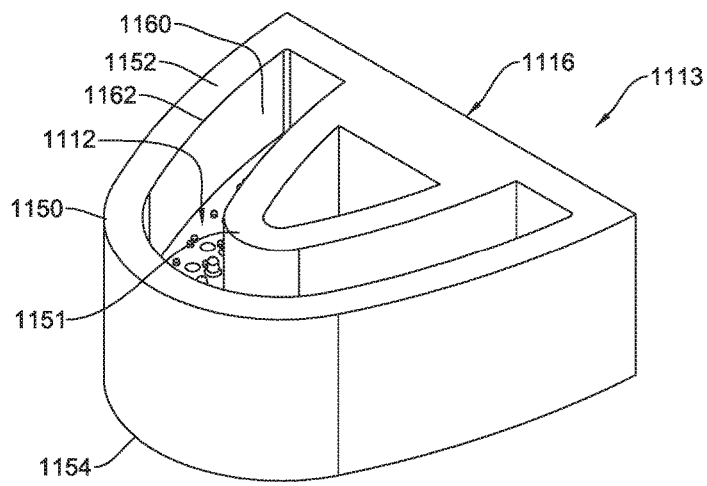
FIG. 126 is a front perspective view of another example mold and base assembly in accordance with the present disclosure.

The dental model base 1112 may have a width $W_1$ (see FIG. 119) and a height $H_1$ (see FIG. 125). The width $W_1$ may be measured between inner and outer edges of the model support surface 1128. The width $W_1$ may remain substantially constant around the full arc of the model support surface 1128.

The pin apertures 1134 may be arranged at predetermined spaced apart locations around the model support surface 1128. The spacing and orientation of the pin apertures 1134 may coincide with the layout of apertures illustrated in FIG. 137. As discussed above, FIG. 63 illustrates upper and lower arcs with pin apertures positioned along each of the arcs (U) and (L). The dental model base 1112 may be either an upper or lower dental model base. Other dental model bases may represent the other of the upper or lower arrangement of holes shown in FIG. 137. The plurality of tapered pins 1118 positioned in the pin apertures 1134 may correspond with average positions of teeth or different mouth sizes (i.e., small, medium and large size mouths) as discussed above. The pins 1118 may be aligned with individual teeth of the teeth model formed from the cured modeling block 1114.

The cured modeling block 1114 may include top and bottom surfaces 1170, 1172, opposing inner and outer side surfaces 1174, 1176, front and rear ends 1178, 1180, and a plurality of indexing apertures 1184 (see FIG. 121). The cured modeling block 1114 may also have a height $H_3$ (see FIG. 125) and a width $W_3$ (see FIG. 119). Width $W_3$ may be substantially similar to the width $W_1$. The height $H_3$ is typically greater than a height of that portion of the dowel pins 1118 that extends above the model support surface 1128 of dental model base 1112.

The shape and size of the cured modeling block 1114 may correspond to a size and shape of at least a portion of the mold cavity of the mold member 1116 as described in detail below. The materials, size, shape, functionality of various aspects of the cured modeling block 1114 may correspond at least in part with the cured modeling block 914 described in further detail above.

The mold member 1116 may include an outer side wall 1150, an inner side wall 1151, top and bottom surfaces 1152, 1154, front and rear ends 1156, 1158, a mold cavity 1160, and top and bottom openings 1162, 1164 into the mold cavity 1160. The mold member 1116 may also include at least one slot feature 1166 sized for insertion of a portion of the dental model base 1112 (see FIG. 121).

The mold cavity 1160 may have a width W2 defined between the outer and inner side walls 1150, 1151 (see FIG. 119). The mold member 1116 may also have a height $H_2$ (see FIG. 51). Typically, the height $H_2$ is greater than the height $H_3$ of the cured modeling block 1114. In at least some examples, the height $H_2$ is greater than the height $H_1$ of the dental model base 1112.

Figure 128:
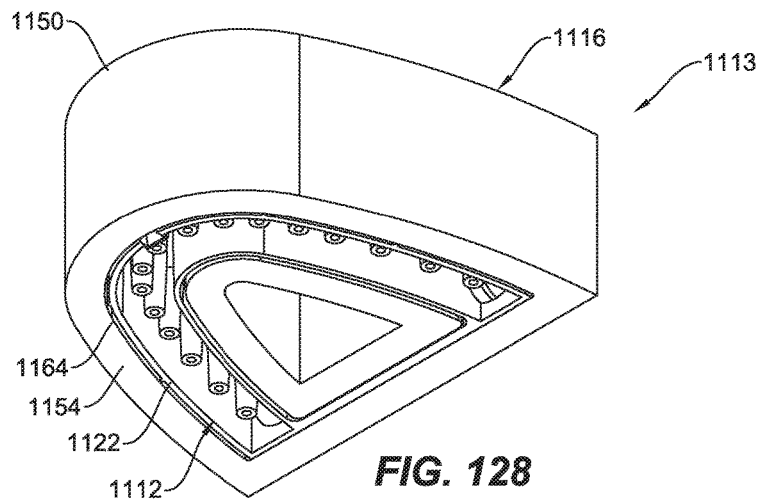
FIG. 128 is another front perspective view of the mold and base assembly of FIG. 126.
Figure 129:
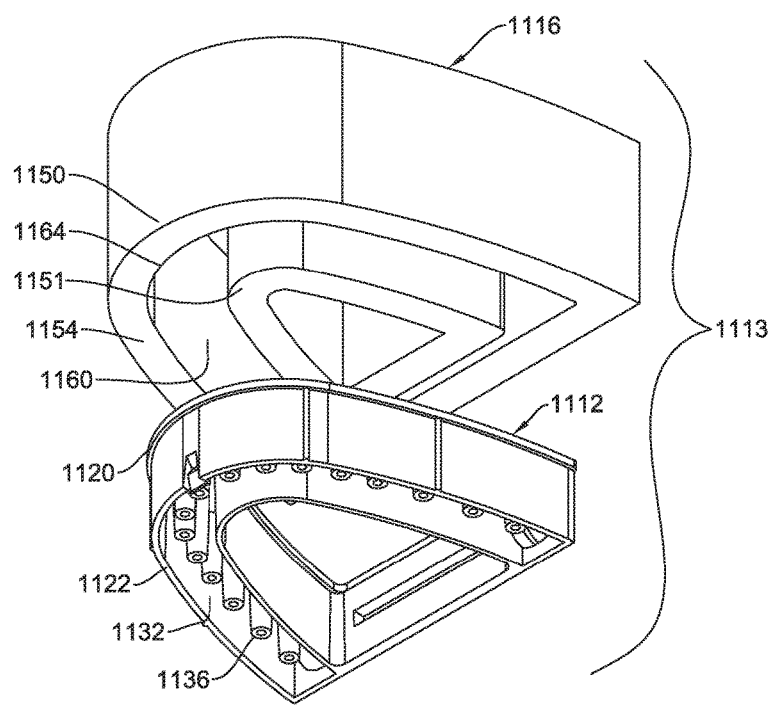
Figure 130:
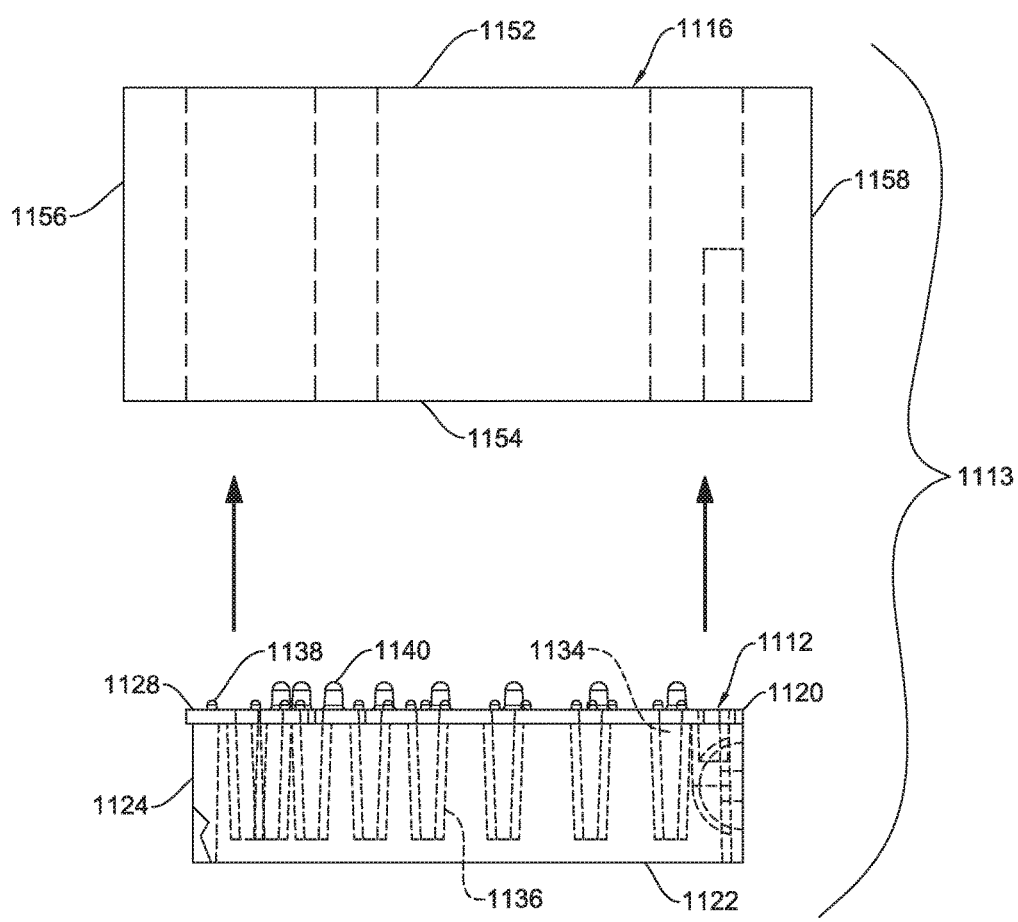
Figure 133:
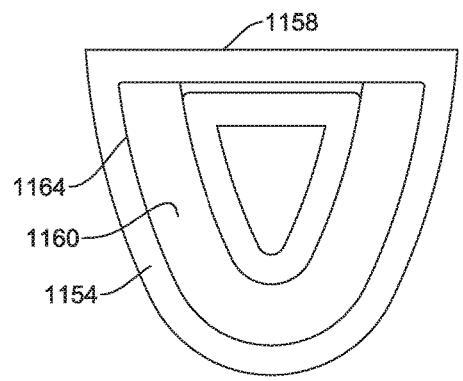
Figure 131:
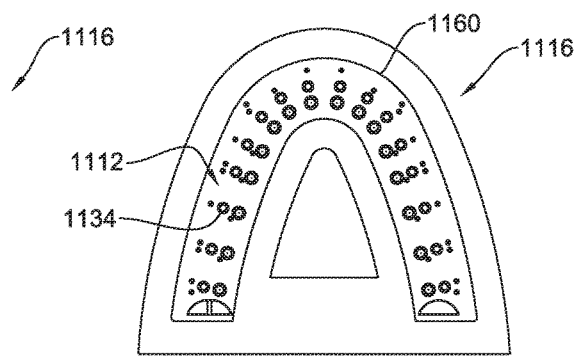
Figure 134:
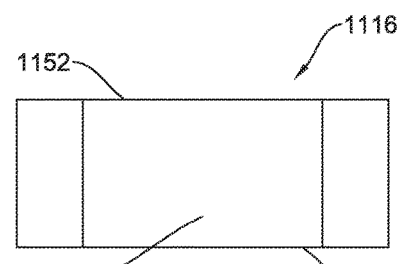
Figure 135:
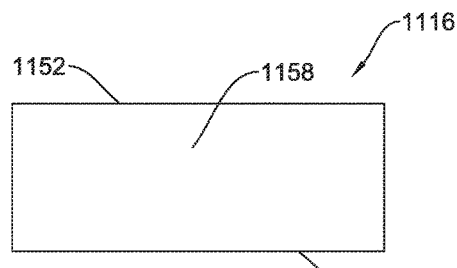
Figure 132:
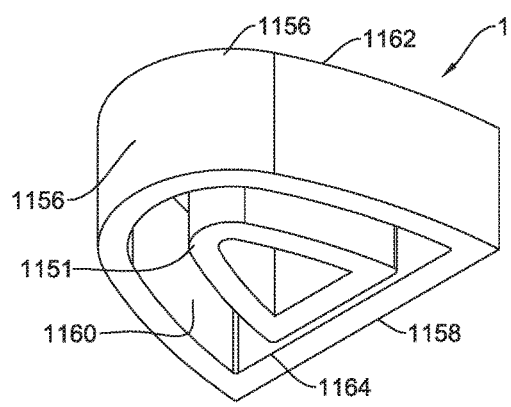

The mold cavity 1160 may be sized to receive at least a portion of the dental model base 1112. FIG. 128 illustrates the dental model base 1112 entirely enclosed within the mold cavity 1160. The mold member 1116 may be mounted to the dental model base 1112 in other ways such as those ways discussed above related to dental model base 1112 and mold member 1116. In at least some arrangements, the mold member 1116 (as with the mold member 1116 described above) may comprise an elastic material that permits easier mounting and dismounting of the mold member 1116 to the dental model base 1112. Various aspects related to the shape, size, material composition of the mold member 1116 may be similar to mold member 1116.

Figure 136:
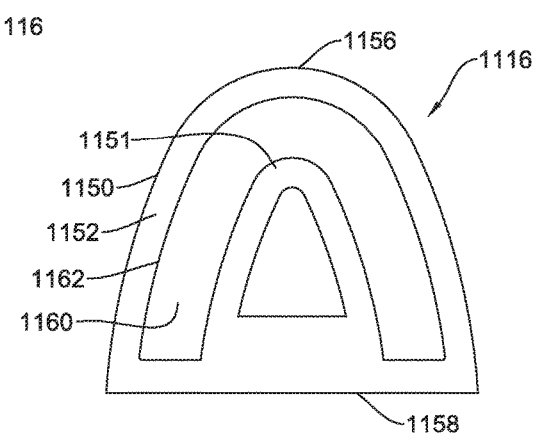

The dental model bases 912, 1012, 1112 illustrated in FIGS. 75-136 and described above may be used in other dental modeling methods and systems. In one example, the dental model bases 912, 1012, 1112 have a dental model formed thereon by the process of rapid prototyping wherein layers of modeling material are deposited on the model support surface of the dental model base until the full dental model is completed. Many different types of rapid prototyping and rapid manufacturing methods and techniques are possible for the creation of a dental model by building up of material on the dental model base. An advantage of using the dental model bases disclosed herein with such rapid prototyping or rapid manufacturing processes is the inclusion of pre-positioned removable pins with the dental model base, wherein the removable pins are aligned with individual teeth of the dental model. This use of pre-positioned dowel pins may eliminate time-consuming and sometimes complicated methods of mounting a pin to a completed dental model in association with a tooth of the dental model and then mounting the teeth model to a base in separate steps.

In one example method, a plurality of removable dowel pins are mounted to one of the dental model bases 912, 1012, 1112. The model engagement portion of at least some of the removable dowel pins is covered with an epoxy or other bonding agent to promote adhesion between the dental model and the dowel pins. In some arrangements, epoxy or other bonding agent is also applied to at least some of the indexing members (i.e., indexing members 38, 40), which may be particularly useful for connection between the dental model base and that portion of the dental model to be formed that is not to removed from the dental model base. In a following step, the dental model is formed by depositing layers of model material on the model support surface using a rapid prototyping or other rapid manufacturing process until the dental model is completely formed. The dental model may be completely formed after completion of formation of a particular tooth or teeth of interest and is not inclusive of all teeth of, for example, a person's upper or lower set of teeth.

The use of epoxy or other bonding material on the model engagement portion of the dowel pins may help in locating or identifying portions of the dowel pins by the rapid prototyping device or when later identifying the particular teeth of interest to be removed from the dental model base.

Other examples of dental model bases, attachment plates, and other dental devices that may be useful with the inventive principles disclosed herein or shown and described in, for example, U.S. Pat. Nos. D429,815, D430,672, D433,136, D433,754, D444,559, D443,363, D456,904, D457,964, D457,963, D456,903, D457,636, D457,243, D456,902, D457,637, D464,432, D465,027, D464,431, D464,732, D468,432, D468,018, D481,797, D469,537, 5,788,490, 5,800,166, 5,868,569, 5,934,901, 6,471,513, 6,884,068, 7,044,734 and 7,210,931, which are incorporated herein by reference in their entirety. This family of patents and patent applications relate to, but is not limited to, attachment plates, dental model bases, opposing bases and other devices for full and quadrant dental applications. These devices may include removable or fixed pins. At least some of these devices are capable of attachment to an articulator or attachment plate with a ball and socket and latch connection. At least some of the devices are also configured for attachment to pouring jigs and other articulator and mounting devices.

It is noted that not all of the features characterized herein need to be incorporated within a given arrangement, for the arrangement to include improvements according to the present disclosure. Furthermore, since many arrangements of the present disclosure can be made without departing from the spirit and scope of the invention, the invention resides in the claims hereinafter appended.

What is claimed is:

1. A method of forming a dental model, comprising:
providing a dental model base, a mounting plate, at least one removable pin, and a digital image of at least one tooth, the dental model base including a plate mounting surface with a plurality of pin apertures formed therein, the at least one removable pin permanently mounted to the mounting plate and insertable into the plurality of pin apertures to removable mount the mounting plate to the dental model base, the mounting plate defining a model mounting surface;
delivering data representing the digital image to a rapid prototyping device;
forming a dental model directly onto the model mounting surface of the mounting plate with the rapid prototyping device based on the delivered data.

2. The method of claim 1, wherein the mounting plate includes a plurality of removable pins arranged at spaced apart locations that represent average spacing of teeth.

3. The method of claim 1, wherein forming the dental model includes depositing a plurality of layers of model material with the rapid prototyping device.

4. The method of claim 1, wherein the at least one pin is aligned with an individual tooth of the dental model.

5. The method of claim 1, further comprising covering model mounting surface with a bonding agent before forming the dental model on the model mounting surface.

6. The method of claim 1, further comprising assembling the mounting plate and dental model base before forming the dental model on the model mounting surface.

7. The method of claim 1, wherein the plate mounting surface is planar and the mounting plate is arranged in its entirety above the plate mounting surface.

8. A method of forming a dental model, comprising:
providing a dental model base, a mounting plate, and a digital image of at least one tooth, the dental model base including a plate mounting surface having a plurality of pin apertures formed therein, and the mounting plate including a plurality of pins and a model mounting surface;
assembling the dental model base and mounting plate by inserting the plurality of pins into the plurality of pin apertures and supporting the mounting plate on the plate mounting surface;
delivering data representing the digital image to a rapid prototyping device;
forming a dental model directly on the model mounting surface with the rapid prototyping device based on the delivered data, at least one tooth of the dental model being aligned with one of the plurality of pins of the mounting plate.

9. The method of claim 8, wherein the plurality of pins are arranged at spaced apart locations that represent average spacing of teeth.

10. The method of claim 9, wherein each of the plurality of pins is aligned with a separate tooth of the dental model.

11. The method of claim 8, wherein forming the dental model includes depositing a plurality of layers of model material with the rapid prototyping device.

12. The method of claim 8, wherein the plurality of pins are permanently mounted to the mounting plate, and assembling the dental model base and the mounting plate includes removably inserting the plurality of pins into the plurality of pin apertures.

13. The method of claim 8, further comprising applying an adhesive to the model mounting surface before forming the dental model on the model mounting surface.

14. A method of forming a dental model, comprising:
delivering data representing a digital image of at least one tooth to a rapid prototyping device;
forming a dental model with the rapid prototyping device based on the delivered data;
connecting the dental model to a mounting plate, the mounting plate including a plurality of pins arranged at spaced apart locations that represent average spacing of teeth, one end of the plurality of pins being mounted to the mounting plate, and an opposite end of the plurality of pins being insertable into a plurality of spaced apart pin apertures of a dental model base to releasably connect the mounting plate to the dental model base, the mounting plate being supported on a plate mounting surface of the dental model base, and the plurality of pin apertures being formed in the plate mounting surface.

15. The method of claim 14, wherein forming the dental model includes depositing a plurality of layers of model material with the rapid prototyping device.

16. The method of claim 14, wherein the plurality of pins are permanently mounted to the mounting plate, the mounting plate defining a model mounting surface.

17. The method of claim 16, further comprising assembling the dental model base and the mounting plate prior to connecting the dental model to the mounting plate by inserting the plurality of pins into the plurality of pin apertures.

18. The method of claim 14, wherein each of the plurality of pins is aligned with a separate tooth of the dental model.

19. The method of claim 14, wherein connecting the mounting plate to the dental model includes bonding with an adhesive.

\* \* \* \* \*